(12) United States Patent
Schneck et al.

(10) Patent No.: US 10,463,750 B2
(45) Date of Patent: Nov. 5, 2019

(54) ANTIGEN-SPECIFIC T CELL REDIRECTORS

(71) Applicant: The Johns Hopkins University, Baltimore, MD (US)

(72) Inventors: Jonathan Schneck, Baltimore, MD (US); Christian Schuetz, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 59 days.

(21) Appl. No.: 14/767,342

(22) PCT Filed: Feb. 14, 2014

(86) PCT No.: PCT/US2014/016449
§ 371 (c)(1),
(2) Date: Aug. 12, 2015

(87) PCT Pub. No.: WO2014/127220
PCT Pub. Date: Aug. 21, 2014

(65) Prior Publication Data
US 2015/0366991 A1    Dec. 24, 2015

Related U.S. Application Data

(60) Provisional application No. 61/783,852, filed on Mar. 14, 2013, provisional application No. 61/765,263, filed on Feb. 15, 2013.

(51) Int. Cl.
| | |
|---|---|
| *A61K 47/69* | (2017.01) |
| *C07K 16/18* | (2006.01) |
| *C07K 16/28* | (2006.01) |
| *C07K 16/30* | (2006.01) |
| *A61K 47/68* | (2017.01) |
| *B82Y 5/00* | (2011.01) |

(52) U.S. Cl.
CPC ...... *A61K 47/6923* (2017.08); *A61K 47/6891* (2017.08); *C07K 16/18* (2013.01); *C07K 16/2833* (2013.01); *C07K 16/30* (2013.01); *B82Y 5/00* (2013.01); *C07K 2317/21* (2013.01); *C07K 2319/00* (2013.01); *C07K 2319/01* (2013.01); *C07K 2319/33* (2013.01)

(58) Field of Classification Search
CPC .......... A61K 47/6929; A61K 47/6891
See application file for complete search history.

(56) References Cited

U.S. PATENT DOCUMENTS

| | | | |
|---|---|---|---|
| 7,763,243 B2 * | 7/2010 | Lum | A61K 38/193 424/178.1 |
| 2005/0042218 A1 | 2/2005 | Zauderer | |
| 2006/0134125 A1 | 6/2006 | Luxembourg et al. | |
| 2010/0008920 A1 | 1/2010 | Schneck et al. | |
| 2011/0159021 A1 | 6/2011 | Munshi et al. | |
| 2012/0034221 A1 | 2/2012 | Bonvini et al. | |

FOREIGN PATENT DOCUMENTS

| | | |
|---|---|---|
| WO | 199807441 A1 | 2/1998 |
| WO | 2002102299 A2 | 12/2002 |
| WO | 2009094273 A2 | 7/2009 |

OTHER PUBLICATIONS

Oelke and Schneck (Immunology Research, 2010, vol. 47, pp. 248-256).*
Hammer (mAbs, 2012, vol. 4, pp. 571-577).*
Maeda et al, Bioconjugate Chemisty, 1992, vol. 3, pp. 351-362 (Year: 1992).*
Alexis et al (Molecular Pharmaceutics, 2008, vol. 5, pp. 505-515) (Year: 2008).*
Kranz et al., "Conjugates of folate and anti-T-cell-receptor antibodies specifically target folate-receptor-positive tumor cells for lysis," Proc. Natl. Acad. Sci. US 92, 9057-61, 1995.
Oelke & Schneck, "Overview of a HLA-Ig based 'Lego-like system' for T cell monitoring, modulation and expansion," Immunologic Res. 47, 248-56, 2010.
Robert et al., "Antibody-conjugated MHC class I tetramers can target tumor cells for specific lysis by T lymphocytes," Eur. J. Immunol. 30, 3165-70, 2000.
Steenblock et al., "Antigen presentation on artificial acellular substrates: modular systems for flexible, adaptable immunotherapy," Expert Opin. Biol. Therapy 9, 451-64, 2009.
Supplementary European Search Report for EP 14751537.3, 8 pages, dated Sep. 12, 2016.
James et al., "Biophysical Mechanism of T Cell Receptor Triggering in a Reconstituted System", Nature, 2012, vol. 487 (7405), pp. 64-69.

* cited by examiner

*Primary Examiner* — Karen A. Canella
(74) *Attorney, Agent, or Firm* — Morgan, Lewis & Bockius LLP

(57) ABSTRACT

This disclosure describes compositions and methods for selectively recruiting antigen-specific T cells and re-direct them to kill targeted cells, particularly tumor cells. This approach permits selective engagement of specific effector cell populations and, by using nanoparticles, overcomes the geometric limitations associated with previous approaches.

10 Claims, 12 Drawing Sheets

Specification includes a Sequence Listing.

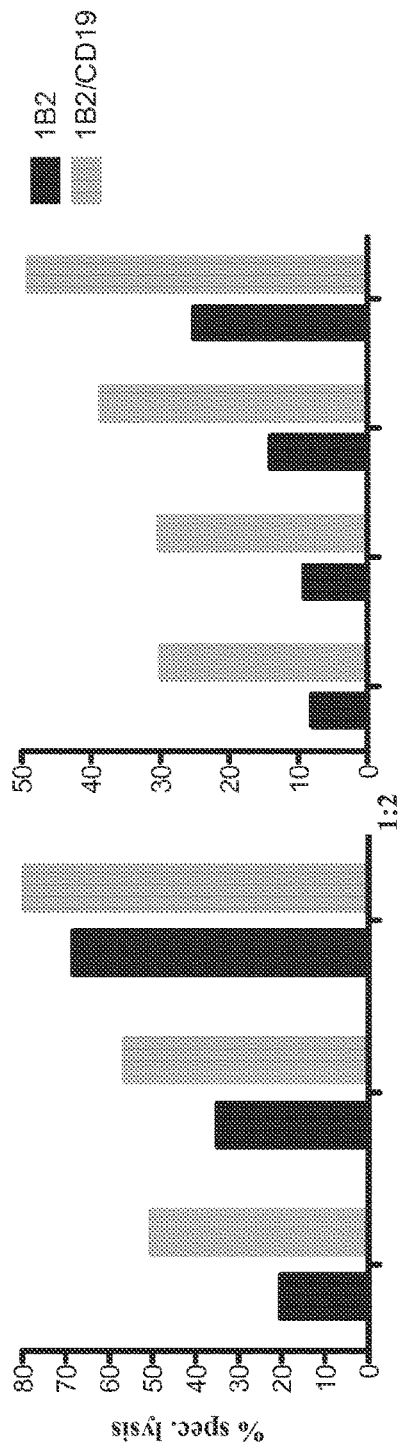
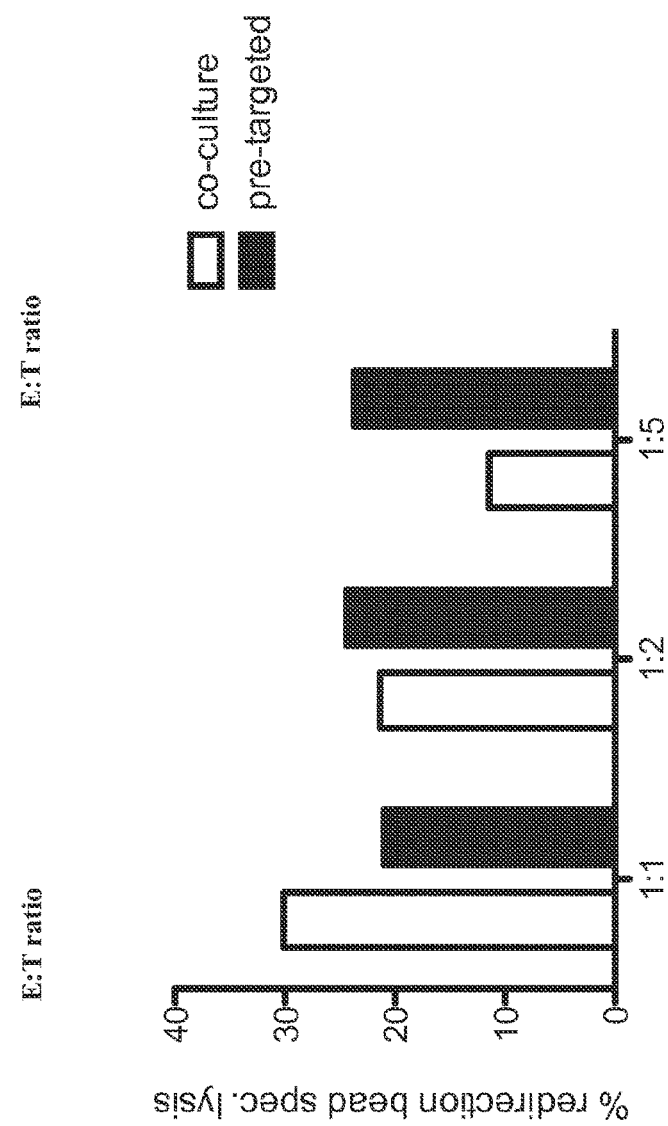
FIG. 4A
FIG. 4B

SEQUENCE LISTING

```
<160> NUMBER OF SEQ ID NOS: 258

<210> SEQ ID NO 1
<211> LENGTH: 8
<212> TYPE: PRT
<213> ORGANISM: Artificial Sequence
<220> FEATURE:
<223> OTHER INFORMATION: artificial peptide

<400> SEQUENCE: 1

Ser Ile Tyr Arg Tyr Tyr Gly Leu
1               5

<210> SEQ ID NO 2
<211> LENGTH: 8
<212> TYPE: PRT
<213> ORGANISM: Artificial Sequence
<220> FEATURE:
<223> OTHER INFORMATION: artificial peptide

<400> SEQUENCE: 2

Ser Ile Ile Asn Phe Glu Lys Leu
1               5

<210> SEQ ID NO 3
<211> LENGTH: 9
<212> TYPE: PRT
<213> ORGANISM: Artificial Sequence
<220> FEATURE:
<223> OTHER INFORMATION: artificial peptide

<400> SEQUENCE: 3

Gln Leu Ser Pro Phe Pro Phe Asp Leu
1               5

<210> SEQ ID NO 4
<211> LENGTH: 9
<212> TYPE: PRT
<213> ORGANISM: Artificial Sequence
<220> FEATURE:
<223> OTHER INFORMATION: artificial peptide

<400> SEQUENCE: 4

Lys Val Pro Arg Asn Gln Asp Trp Leu
```

```
1               5

<210> SEQ ID NO 5
<211> LENGTH: 9
<212> TYPE: PRT
<213> ORGANISM: Epstein Barr Virus

<400> SEQUENCE: 5

Gly Leu Cys Thr Leu Val Ala Met Leu
1               5

<210> SEQ ID NO 6
<211> LENGTH: 9
<212> TYPE: PRT
<213> ORGANISM: Epstein Barr Virus

<400> SEQUENCE: 6

Arg Tyr Ser Ile Phe Phe Asp Tyr Met
1               5

<210> SEQ ID NO 7
<211> LENGTH: 8
<212> TYPE: PRT
<213> ORGANISM: Epstein Barr Virus

<400> SEQUENCE: 7

Leu Leu Trp Thr Leu Val Val Leu
1               5

<210> SEQ ID NO 8
<211> LENGTH: 9
<212> TYPE: PRT
<213> ORGANISM: Epstein Barr Virus

<400> SEQUENCE: 8

Arg Leu Arg Ala Glu Ala Gln Val Lys
1               5

<210> SEQ ID NO 9
<211> LENGTH: 9
<212> TYPE: PRT
<213> ORGANISM: Epstein Barr Virus

<400> SEQUENCE: 9

Ile Val Thr Asp Phe Ser Val Ile Lys
1               5

<210> SEQ ID NO 10
<211> LENGTH: 9
<212> TYPE: PRT
<213> ORGANISM: Epstein Barr Virus

<400> SEQUENCE: 10

Pro Tyr Leu Phe Trp Leu Ala Ala Ile
1               5

<210> SEQ ID NO 11
<211> LENGTH: 9
<212> TYPE: PRT
<213> ORGANISM: Epstein Barr Virus

<400> SEQUENCE: 11

Thr Leu Asp Tyr Lys Pro Leu Ser Val
1               5
```

```
<210> SEQ ID NO 12
<211> LENGTH: 9
<212> TYPE: PRT
<213> ORGANISM: Epstein Barr Virus

<400> SEQUENCE: 12

Thr Tyr Ser Ala Gly Ile Val Gln Ile
1               5

<210> SEQ ID NO 13
<211> LENGTH: 11
<212> TYPE: PRT
<213> ORGANISM: Epstein Barr Virus

<400> SEQUENCE: 13

Tyr Ser Glu His Pro Thr Phe Thr Ser Gln Tyr
1               5                   10

<210> SEQ ID NO 14
<211> LENGTH: 9
<212> TYPE: PRT
<213> ORGANISM: Epstein Barr Virus

<400> SEQUENCE: 14

Arg Val Arg Ala Tyr Thr Tyr Ser Lys
1               5

<210> SEQ ID NO 15
<211> LENGTH: 10
<212> TYPE: PRT
<213> ORGANISM: Epstein Barr Virus

<400> SEQUENCE: 15

Ala Val Phe Asp Arg Lys Ser Asp Ala Lys
1               5                   10

<210> SEQ ID NO 16
<211> LENGTH: 9
<212> TYPE: PRT
<213> ORGANISM: Epstein Barr Virus

<400> SEQUENCE: 16

Cys Leu Gly Gly Leu Leu Thr Met Val
1               5

<210> SEQ ID NO 17
<211> LENGTH: 9
<212> TYPE: PRT
<213> ORGANISM: Epstein Barr Virus

<400> SEQUENCE: 17

Thr Tyr Pro Val Leu Glu Glu Met Phe
1               5

<210> SEQ ID NO 18
<211> LENGTH: 9
<212> TYPE: PRT
<213> ORGANISM: Epstein Barr Virus

<400> SEQUENCE: 18

Thr Val Cys Gly Gly Ile Met Phe Leu
1               5

<210> SEQ ID NO 19
```

```
<211> LENGTH: 11
<212> TYPE: PRT
<213> ORGANISM: Epstein Barr Virus

<400> SEQUENCE: 19

Ser Ser Cys Ser Ser Cys Pro Leu Ser Lys Ile
1               5                   10

<210> SEQ ID NO 20
<211> LENGTH: 9
<212> TYPE: PRT
<213> ORGANISM: Epstein Barr Virus

<400> SEQUENCE: 20

Tyr Val Leu Asp His Leu Ile Val Val
1               5

<210> SEQ ID NO 21
<211> LENGTH: 9
<212> TYPE: PRT
<213> ORGANISM: Epstein Barr Virus

<400> SEQUENCE: 21

Thr Tyr Gly Pro Val Phe Met Cys Leu
1               5

<210> SEQ ID NO 22
<211> LENGTH: 9
<212> TYPE: PRT
<213> ORGANISM: Epstein Barr Virus

<400> SEQUENCE: 22

Ala Thr Ile Gly Thr Ala Met Tyr Lys
1               5

<210> SEQ ID NO 23
<211> LENGTH: 9
<212> TYPE: PRT
<213> ORGANISM: Epstein Barr Virus

<400> SEQUENCE: 23

Leu Leu Trp Thr Leu Val Val Leu Leu
1               5

<210> SEQ ID NO 24
<211> LENGTH: 10
<212> TYPE: PRT
<213> ORGANISM: Epstein Barr Virus

<400> SEQUENCE: 24

Asp Tyr Cys Asn Val Leu Asn Lys Glu Phe
1               5                   10

<210> SEQ ID NO 25
<211> LENGTH: 10
<212> TYPE: PRT
<213> ORGANISM: Epstein Barr Virus

<400> SEQUENCE: 25

Phe Leu Tyr Ala Leu Ala Leu Leu Leu Leu
1               5                   10

<210> SEQ ID NO 26
<211> LENGTH: 10
<212> TYPE: PRT
```

-continued

```
<213> ORGANISM: Epstein Barr Virus

<400> SEQUENCE: 26

Leu Leu Asp Phe Val Arg Phe Met Gly Val
1               5                   10

<210> SEQ ID NO 27
<211> LENGTH: 9
<212> TYPE: PRT
<213> ORGANISM: Epstein Barr Virus

<400> SEQUENCE: 27

Tyr Leu Leu Glu Met Leu Trp Arg Leu
1               5

<210> SEQ ID NO 28
<211> LENGTH: 9
<212> TYPE: PRT
<213> ORGANISM: Epstein Barr Virus

<400> SEQUENCE: 28

Phe Leu Asp Lys Gly Thr Tyr Thr Leu
1               5

<210> SEQ ID NO 29
<211> LENGTH: 9
<212> TYPE: PRT
<213> ORGANISM: Epstein Barr Virus

<400> SEQUENCE: 29

Ile Leu Ile Tyr Asn Gly Trp Tyr Ala
1               5

<210> SEQ ID NO 30
<211> LENGTH: 9
<212> TYPE: PRT
<213> ORGANISM: Epstein Barr Virus

<400> SEQUENCE: 30

Ser Leu Val Ile Val Thr Thr Phe Val
1               5

<210> SEQ ID NO 31
<211> LENGTH: 9
<212> TYPE: PRT
<213> ORGANISM: Epstein Barr Virus

<400> SEQUENCE: 31

Thr Leu Phe Ile Gly Ser His Val Val
1               5

<210> SEQ ID NO 32
<211> LENGTH: 9
<212> TYPE: PRT
<213> ORGANISM: Epstein Barr Virus

<400> SEQUENCE: 32

Leu Met Ile Ile Pro Leu Ile Asn Val
1               5

<210> SEQ ID NO 33
<211> LENGTH: 9
<212> TYPE: PRT
<213> ORGANISM: Epstein Barr Virus
```

```
<400> SEQUENCE: 33

Val Leu Gln Trp Ala Ser Leu Ala Val
1               5

<210> SEQ ID NO 34
<211> LENGTH: 10
<212> TYPE: PRT
<213> ORGANISM: Epstein Barr Virus

<400> SEQUENCE: 34

Asp Thr Pro Leu Ile Pro Leu Thr Ile Phe
1               5                   10

<210> SEQ ID NO 35
<211> LENGTH: 9
<212> TYPE: PRT
<213> ORGANISM: Epstein Barr Virus

<400> SEQUENCE: 35

Ser Val Arg Asp Arg Leu Ala Arg Leu
1               5

<210> SEQ ID NO 36
<211> LENGTH: 9
<212> TYPE: PRT
<213> ORGANISM: Epstein Barr Virus

<400> SEQUENCE: 36

Leu Leu Val Asp Leu Leu Trp Leu Leu
1               5

<210> SEQ ID NO 37
<211> LENGTH: 9
<212> TYPE: PRT
<213> ORGANISM: Epstein Barr Virus

<400> SEQUENCE: 37

Tyr Leu Gln Gln Asn Trp Trp Thr Leu
1               5

<210> SEQ ID NO 38
<211> LENGTH: 9
<212> TYPE: PRT
<213> ORGANISM: Epstein Barr Virus

<400> SEQUENCE: 38

Tyr Phe Leu Glu Ile Leu Trp Arg Leu
1               5

<210> SEQ ID NO 39
<211> LENGTH: 9
<212> TYPE: PRT
<213> ORGANISM: Epstein Barr Virus

<400> SEQUENCE: 39

Leu Leu Ser Ala Trp Ile Leu Thr Ala
1               5

<210> SEQ ID NO 40
<211> LENGTH: 9
<212> TYPE: PRT
<213> ORGANISM: Epstein Barr Virus

<400> SEQUENCE: 40
```

```
Ala Leu Leu Val Leu Tyr Ser Phe Ala
1               5
```

<210> SEQ ID NO 41
<211> LENGTH: 10
<212> TYPE: PRT
<213> ORGANISM: Epstein Barr Virus

<400> SEQUENCE: 41

```
Ala Val Phe Asp Arg Lys Ser Asp Ala Lys
1               5                   10
```

<210> SEQ ID NO 42
<211> LENGTH: 9
<212> TYPE: PRT
<213> ORGANISM: Epstein Barr Virus

<400> SEQUENCE: 42

```
Ile Leu Thr Asp Phe Ser Val Ile Lys
1               5
```

<210> SEQ ID NO 43
<211> LENGTH: 15
<212> TYPE: PRT
<213> ORGANISM: Epstein Barr Virus

<400> SEQUENCE: 43

```
Leu Pro Gly Pro Gln Val Thr Ala Val Leu Leu His Glu Glu Ser
1               5                   10                  15
```

<210> SEQ ID NO 44
<211> LENGTH: 14
<212> TYPE: PRT
<213> ORGANISM: Epstein Barr Virus

<400> SEQUENCE: 44

```
Asp Glu Pro Ala Ser Thr Glu Pro Val His Asp Gln Leu Leu
1               5                   10
```

<210> SEQ ID NO 45
<211> LENGTH: 9
<212> TYPE: PRT
<213> ORGANISM: Epstein Barr Virus

<400> SEQUENCE: 45

```
Ile Val Thr Asp Phe Ser Val Ile Thr
1               5
```

<210> SEQ ID NO 46
<211> LENGTH: 9
<212> TYPE: PRT
<213> ORGANISM: Epstein Barr Virus

<400> SEQUENCE: 46

```
Ile Val Thr Asp Phe Ser Val Ile Arg
1               5
```

<210> SEQ ID NO 47
<211> LENGTH: 10
<212> TYPE: PRT
<213> ORGANISM: Epstein Barr Virus

<400> SEQUENCE: 47

```
Ser Leu Phe Asp Arg Lys Ser Asp Ala Lys
1               5                   10
```

<210> SEQ ID NO 48
<211> LENGTH: 15
<212> TYPE: PRT
<213> ORGANISM: Epstein Barr Virus

<400> SEQUENCE: 48

Asn Pro Thr Gln Ala Pro Val Ile Gln Leu Val His Ala Val Tyr
1               5                   10                  15

<210> SEQ ID NO 49
<211> LENGTH: 9
<212> TYPE: PRT
<213> ORGANISM: Epstein Barr Virus

<400> SEQUENCE: 49

Ile Tyr Val Leu Val Met Leu Val Leu
1               5

<210> SEQ ID NO 50
<211> LENGTH: 8
<212> TYPE: PRT
<213> ORGANISM: Epstein Barr Virus

<400> SEQUENCE: 50

Pro Tyr Leu Phe Trp Leu Ala Ala
1               5

<210> SEQ ID NO 51
<211> LENGTH: 9
<212> TYPE: PRT
<213> ORGANISM: Epstein Barr Virus

<400> SEQUENCE: 51

Pro Tyr Leu Phe Trp Leu Ala Ala Ile
1               5

<210> SEQ ID NO 52
<211> LENGTH: 9
<212> TYPE: PRT
<213> ORGANISM: Epstein Barr Virus

<400> SEQUENCE: 52

Arg Pro Gln Lys Arg Pro Ser Cys Ile
1               5

<210> SEQ ID NO 53
<211> LENGTH: 9
<212> TYPE: PRT
<213> ORGANISM: Epstein Barr Virus

<400> SEQUENCE: 53

His Pro Val Gly Glu Ala Asp Tyr Phe
1               5

<210> SEQ ID NO 54
<211> LENGTH: 11
<212> TYPE: PRT
<213> ORGANISM: Epstein Barr Virus

<400> SEQUENCE: 54

His Pro Val Gly Glu Ala Asp Tyr Phe Glu Tyr
1               5                   10

```
<210> SEQ ID NO 55
<211> LENGTH: 9
<212> TYPE: PRT
<213> ORGANISM: Epstein Barr Virus

<400> SEQUENCE: 55

Ile Pro Gln Cys Arg Leu Thr Pro Leu
1               5

<210> SEQ ID NO 56
<211> LENGTH: 9
<212> TYPE: PRT
<213> ORGANISM: Epstein Barr Virus

<400> SEQUENCE: 56

Val Leu Lys Asp Ala Ile Lys Asp Leu
1               5

<210> SEQ ID NO 57
<211> LENGTH: 10
<212> TYPE: PRT
<213> ORGANISM: Epstein Barr Virus

<400> SEQUENCE: 57

Tyr His Leu Ile Val Asp Thr Asp Ser Leu
1               5                   10

<210> SEQ ID NO 58
<211> LENGTH: 10
<212> TYPE: PRT
<213> ORGANISM: Epstein Barr Virus

<400> SEQUENCE: 58

Asp Thr Pro Leu Ile Pro Leu Thr Ile Phe
1               5                   10

<210> SEQ ID NO 59
<211> LENGTH: 9
<212> TYPE: PRT
<213> ORGANISM: Epstein Barr Virus

<400> SEQUENCE: 59

Arg Pro Thr Glu Leu Gln Pro Thr Pro
1               5

<210> SEQ ID NO 60
<211> LENGTH: 9
<212> TYPE: PRT
<213> ORGANISM: Epstein Barr Virus

<400> SEQUENCE: 60

Gln Ala Lys Trp Arg Leu Gln Thr Leu
1               5

<210> SEQ ID NO 61
<211> LENGTH: 9
<212> TYPE: PRT
<213> ORGANISM: Epstein Barr Virus

<400> SEQUENCE: 61

Ala Tyr Ser Ser Trp Met Tyr Ser Tyr
1               5

<210> SEQ ID NO 62
<211> LENGTH: 8
```

```
<212> TYPE: PRT
<213> ORGANISM: Epstein Barr Virus

<400> SEQUENCE: 62

Arg Tyr Ser Ile Phe Phe Asp Tyr
1               5

<210> SEQ ID NO 63
<211> LENGTH: 9
<212> TYPE: PRT
<213> ORGANISM: Epstein Barr Virus

<400> SEQUENCE: 63

Phe Leu Arg Gly Arg Ala Tyr Gly Leu
1               5

<210> SEQ ID NO 64
<211> LENGTH: 10
<212> TYPE: PRT
<213> ORGANISM: Epstein Barr Virus

<400> SEQUENCE: 64

Lys Arg Pro Pro Ile Phe Ile Arg Arg Leu
1               5                   10

<210> SEQ ID NO 65
<211> LENGTH: 9
<212> TYPE: PRT
<213> ORGANISM: Epstein Barr Virus

<400> SEQUENCE: 65

Arg Pro Pro Ile Phe Ile Arg Arg Leu
1               5

<210> SEQ ID NO 66
<211> LENGTH: 9
<212> TYPE: PRT
<213> ORGANISM: Epstein Barr Virus

<400> SEQUENCE: 66

Leu Glu Lys Ala Arg Gly Ser Thr Tyr
1               5

<210> SEQ ID NO 67
<211> LENGTH: 9
<212> TYPE: PRT
<213> ORGANISM: Epstein Barr Virus

<400> SEQUENCE: 67

His Leu Ala Ala Gln Gly Met Ala Tyr
1               5

<210> SEQ ID NO 68
<211> LENGTH: 9
<212> TYPE: PRT
<213> ORGANISM: Epstein Barr Virus

<400> SEQUENCE: 68

Tyr Pro Leu His Glu Gln His Gly Met
1               5

<210> SEQ ID NO 69
<211> LENGTH: 9
<212> TYPE: PRT
<213> ORGANISM: Epstein Barr Virus
```

```
<400> SEQUENCE: 69

Val Phe Ser Asp Gly Arg Val Ala Cys
1               5

<210> SEQ ID NO 70
<211> LENGTH: 9
<212> TYPE: PRT
<213> ORGANISM: Epstein Barr Virus

<400> SEQUENCE: 70

Val Pro Ala Pro Ala Gly Pro Ile Val
1               5

<210> SEQ ID NO 71
<211> LENGTH: 9
<212> TYPE: PRT
<213> ORGANISM: Epstein Barr Virus

<400> SEQUENCE: 71

Ser Val Arg Asp Arg Leu Ala Arg Leu
1               5

<210> SEQ ID NO 72
<211> LENGTH: 9
<212> TYPE: PRT
<213> ORGANISM: Epstein Barr Virus

<400> SEQUENCE: 72

Arg Leu Arg Ala Glu Ala Gln Val Lys
1               5

<210> SEQ ID NO 73
<211> LENGTH: 10
<212> TYPE: PRT
<213> ORGANISM: Epstein Barr Virus

<400> SEQUENCE: 73

Val Gln Pro Pro Gln Leu Thr Leu Gln Val
1               5                   10

<210> SEQ ID NO 74
<211> LENGTH: 9
<212> TYPE: PRT
<213> ORGANISM: Epstein Barr Virus

<400> SEQUENCE: 74

His Arg Cys Gln Ala Ile Arg Lys Lys
1               5

<210> SEQ ID NO 75
<211> LENGTH: 9
<212> TYPE: PRT
<213> ORGANISM: Epstein Barr Virus

<400> SEQUENCE: 75

Thr Tyr Ser Ala Gly Ile Val Gln Ile
1               5

<210> SEQ ID NO 76
<211> LENGTH: 11
<212> TYPE: PRT
<213> ORGANISM: Epstein Barr Virus

<400> SEQUENCE: 76
```

Arg Arg Ala Arg Ser Leu Ser Ala Glu Arg Tyr
1               5                   10

<210> SEQ ID NO 77
<211> LENGTH: 9
<212> TYPE: PRT
<213> ORGANISM: Epstein Barr Virus

<400> SEQUENCE: 77

Val Ser Phe Ile Glu Phe Val Gly Trp
1               5

<210> SEQ ID NO 78
<211> LENGTH: 10
<212> TYPE: PRT
<213> ORGANISM: Epstein Barr Virus

<400> SEQUENCE: 78

Ala Val Phe Asp Arg Lys Ser Asp Ala Lys
1               5                   10

<210> SEQ ID NO 79
<211> LENGTH: 9
<212> TYPE: PRT
<213> ORGANISM: Epstein Barr Virus

<400> SEQUENCE: 79

Ile Val Thr Asp Phe Ser Val Ile Lys
1               5

<210> SEQ ID NO 80
<211> LENGTH: 9
<212> TYPE: PRT
<213> ORGANISM: Epstein Barr Virus

<400> SEQUENCE: 80

Ala Val Leu Leu His Glu Glu Ser Met
1               5

<210> SEQ ID NO 81
<211> LENGTH: 10
<212> TYPE: PRT
<213> ORGANISM: Epstein Barr Virus

<400> SEQUENCE: 81

Val Glu Ile Thr Pro Tyr Lys Pro Thr Trp
1               5                   10

<210> SEQ ID NO 82
<211> LENGTH: 9
<212> TYPE: PRT
<213> ORGANISM: Epstein Barr Virus

<400> SEQUENCE: 82

Glu Gly Gly Val Gly Trp Arg His Trp
1               5

<210> SEQ ID NO 83
<211> LENGTH: 10
<212> TYPE: PRT
<213> ORGANISM: Epstein Barr Virus

<400> SEQUENCE: 83

Gln Asn Gly Ala Leu Ala Ile Asn Thr Phe

```
1               5                   10
```

<210> SEQ ID NO 84
<211> LENGTH: 10
<212> TYPE: PRT
<213> ORGANISM: Epstein Barr Virus

<400> SEQUENCE: 84

```
Leu Arg Gly Lys Trp Gln Arg Arg Tyr Arg
1               5                   10
```

<210> SEQ ID NO 85
<211> LENGTH: 9
<212> TYPE: PRT
<213> ORGANISM: Epstein Barr Virus

<400> SEQUENCE: 85

```
Arg Arg Ile Tyr Asp Leu Ile Glu Leu
1               5
```

<210> SEQ ID NO 86
<211> LENGTH: 8
<212> TYPE: PRT
<213> ORGANISM: Epstein Barr Virus

<400> SEQUENCE: 86

```
His His Ile Trp Gln Asn Leu Leu
1               5
```

<210> SEQ ID NO 87
<211> LENGTH: 10
<212> TYPE: PRT
<213> ORGANISM: Epstein Barr Virus

<400> SEQUENCE: 87

```
Glu Glu Asn Leu Leu Asp Phe Val Arg Phe
1               5                   10
```

<210> SEQ ID NO 88
<211> LENGTH: 10
<212> TYPE: PRT
<213> ORGANISM: Epstein Barr Virus

<400> SEQUENCE: 88

```
Leu Leu Asp Phe Val Arg Phe Met Gly Val
1               5                   10
```

<210> SEQ ID NO 89
<211> LENGTH: 9
<212> TYPE: PRT
<213> ORGANISM: Epstein Barr Virus

<400> SEQUENCE: 89

```
Leu Asp Phe Val Arg Phe Met Gly Val
1               5
```

<210> SEQ ID NO 90
<211> LENGTH: 9
<212> TYPE: PRT
<213> ORGANISM: Epstein Barr Virus

<400> SEQUENCE: 90

```
Lys Glu His Val Ile Gln Asn Ala Phe
1               5
```

```
<210> SEQ ID NO 91
<211> LENGTH: 9
<212> TYPE: PRT
<213> ORGANISM: Epstein Barr Virus

<400> SEQUENCE: 91

Phe Arg Lys Ala Gln Ile Gln Gly Leu
1               5

<210> SEQ ID NO 92
<211> LENGTH: 9
<212> TYPE: PRT
<213> ORGANISM: Epstein Barr Virus

<400> SEQUENCE: 92

Gln Pro Arg Ala Pro Ile Arg Pro Ile
1               5

<210> SEQ ID NO 93
<211> LENGTH: 9
<212> TYPE: PRT
<213> ORGANISM: Epstein Barr Virus

<400> SEQUENCE: 93

Ser Leu Arg Glu Trp Leu Leu Arg Ile
1               5

<210> SEQ ID NO 94
<211> LENGTH: 9
<212> TYPE: PRT
<213> ORGANISM: Epstein Barr Virus

<400> SEQUENCE: 94

Phe Trp Leu Tyr Ile Val Met Ser Asp
1               5

<210> SEQ ID NO 95
<211> LENGTH: 11
<212> TYPE: PRT
<213> ORGANISM: Epstein Barr Virus

<400> SEQUENCE: 95

Phe Arg Arg Asp Leu Leu Cys Pro Leu Gly Ala
1               5                   10

<210> SEQ ID NO 96
<211> LENGTH: 9
<212> TYPE: PRT
<213> ORGANISM: Epstein Barr Virus

<400> SEQUENCE: 96

Tyr Leu Leu Glu Met Leu Trp Arg Leu
1               5

<210> SEQ ID NO 97
<211> LENGTH: 9
<212> TYPE: PRT
<213> ORGANISM: Epstein Barr Virus

<400> SEQUENCE: 97

Tyr Leu Gln Gln Asn Trp Trp Thr Leu
1               5

<210> SEQ ID NO 98
```

```
<211> LENGTH: 9
<212> TYPE: PRT
<213> ORGANISM: Epstein Barr Virus

<400> SEQUENCE: 98

Thr Leu Leu Val Asp Leu Leu Trp Leu
1               5

<210> SEQ ID NO 99
<211> LENGTH: 12
<212> TYPE: PRT
<213> ORGANISM: Epstein Barr Virus

<400> SEQUENCE: 99

Asp Pro His Gly Pro Val Gln Leu Ser Tyr Tyr Asp
1               5                   10

<210> SEQ ID NO 100
<211> LENGTH: 9
<212> TYPE: PRT
<213> ORGANISM: Epstein Barr Virus

<400> SEQUENCE: 100

Met Gly Ser Leu Glu Met Val Pro Met
1               5

<210> SEQ ID NO 101
<211> LENGTH: 15
<212> TYPE: PRT
<213> ORGANISM: Epstein Barr Virus

<400> SEQUENCE: 101

Glu Asp Pro Tyr Trp Gly Asn Gly Asp Arg His Ser Asp Tyr Gln
1               5                   10                  15

<210> SEQ ID NO 102
<211> LENGTH: 14
<212> TYPE: PRT
<213> ORGANISM: Epstein Barr Virus

<400> SEQUENCE: 102

Asn Pro Val Cys Leu Pro Val Ile Val Ala Pro Tyr Leu Phe
1               5                   10

<210> SEQ ID NO 103
<211> LENGTH: 9
<212> TYPE: PRT
<213> ORGANISM: Epstein Barr Virus

<400> SEQUENCE: 103

Leu Pro Val Ile Val Ala Pro Tyr Leu
1               5

<210> SEQ ID NO 104
<211> LENGTH: 9
<212> TYPE: PRT
<213> ORGANISM: Epstein Barr Virus

<400> SEQUENCE: 104

Pro Tyr Leu Phe Trp Leu Ala Ala Ile
1               5

<210> SEQ ID NO 105
<211> LENGTH: 14
<212> TYPE: PRT
```

<213> ORGANISM: Epstein Barr Virus

<400> SEQUENCE: 105

Ala Ser Cys Phe Thr Ala Ser Val Ser Thr Val Val Thr Ala
1               5                   10

<210> SEQ ID NO 106
<211> LENGTH: 9
<212> TYPE: PRT
<213> ORGANISM: Epstein Barr Virus

<400> SEQUENCE: 106

Phe Thr Ala Ser Val Ser Thr Val Val
1               5

<210> SEQ ID NO 107
<211> LENGTH: 9
<212> TYPE: PRT
<213> ORGANISM: Epstein Barr Virus

<400> SEQUENCE: 107

Ile Glu Asp Pro Pro Phe Asn Ser Leu
1               5

<210> SEQ ID NO 108
<211> LENGTH: 9
<212> TYPE: PRT
<213> ORGANISM: Epstein Barr Virus

<400> SEQUENCE: 108

Arg Arg Arg Trp Arg Arg Leu Thr Val
1               5

<210> SEQ ID NO 109
<211> LENGTH: 9
<212> TYPE: PRT
<213> ORGANISM: Epstein Barr Virus

<400> SEQUENCE: 109

Arg Arg Trp Arg Arg Leu Thr Val Cys
1               5

<210> SEQ ID NO 110
<211> LENGTH: 11
<212> TYPE: PRT
<213> ORGANISM: Epstein Barr Virus

<400> SEQUENCE: 110

Arg Arg Leu Thr Val Cys Gly Gly Ile Met Phe
1               5                   10

<210> SEQ ID NO 111
<211> LENGTH: 9
<212> TYPE: PRT
<213> ORGANISM: Epstein Barr Virus

<400> SEQUENCE: 111

Thr Val Cys Gly Gly Ile Met Phe Leu
1               5

<210> SEQ ID NO 112
<211> LENGTH: 14
<212> TYPE: PRT
<213> ORGANISM: Epstein Barr Virus

```
<400> SEQUENCE: 112

Met Phe Leu Ala Cys Val Leu Val Leu Ile Val Asp Ala Val
1               5                   10

<210> SEQ ID NO 113
<211> LENGTH: 9
<212> TYPE: PRT
<213> ORGANISM: Epstein Barr Virus

<400> SEQUENCE: 113

Leu Ile Val Asp Ala Val Leu Gln Leu
1               5

<210> SEQ ID NO 114
<211> LENGTH: 9
<212> TYPE: PRT
<213> ORGANISM: Epstein Barr Virus

<400> SEQUENCE: 114

Gly Leu Gly Thr Leu Gly Ala Ala Ile
1               5

<210> SEQ ID NO 115
<211> LENGTH: 9
<212> TYPE: PRT
<213> ORGANISM: Epstein Barr Virus

<400> SEQUENCE: 115

Leu Leu Trp Thr Leu Val Val Leu Leu
1               5

<210> SEQ ID NO 116
<211> LENGTH: 11
<212> TYPE: PRT
<213> ORGANISM: Epstein Barr Virus

<400> SEQUENCE: 116

Ser Ser Cys Ser Ser Cys Pro Leu Ser Lys Ile
1               5                   10

<210> SEQ ID NO 117
<211> LENGTH: 9
<212> TYPE: PRT
<213> ORGANISM: Epstein Barr Virus

<400> SEQUENCE: 117

Ile Leu Leu Ala Arg Leu Phe Leu Tyr
1               5

<210> SEQ ID NO 118
<211> LENGTH: 9
<212> TYPE: PRT
<213> ORGANISM: Epstein Barr Virus

<400> SEQUENCE: 118

Phe Leu Tyr Ala Leu Ala Leu Leu Leu
1               5

<210> SEQ ID NO 119
<211> LENGTH: 9
<212> TYPE: PRT
<213> ORGANISM: Epstein Barr Virus

<400> SEQUENCE: 119
```

Thr Tyr Gly Pro Val Phe Met Cys Leu
1               5

<210> SEQ ID NO 120
<211> LENGTH: 9
<212> TYPE: PRT
<213> ORGANISM: Epstein Barr Virus

<400> SEQUENCE: 120

Cys Leu Gly Gly Leu Leu Thr Met Val
1               5

<210> SEQ ID NO 121
<211> LENGTH: 10
<212> TYPE: PRT
<213> ORGANISM: Epstein Barr Virus

<400> SEQUENCE: 121

Val Met Ser Asn Thr Leu Leu Ser Ala Trp
1               5                   10

<210> SEQ ID NO 122
<211> LENGTH: 9
<212> TYPE: PRT
<213> ORGANISM: Epstein Barr Virus

<400> SEQUENCE: 122

Leu Thr Ala Gly Phe Leu Ile Phe Leu
1               5

<210> SEQ ID NO 123
<211> LENGTH: 9
<212> TYPE: PRT
<213> ORGANISM: Epstein Barr Virus

<400> SEQUENCE: 123

Leu Leu Ser Ala Trp Ile Leu Thr Ala
1               5

<210> SEQ ID NO 124
<211> LENGTH: 14
<212> TYPE: PRT
<213> ORGANISM: Epstein Barr Virus

<400> SEQUENCE: 124

Leu Val Ser Asp Tyr Cys Asn Val Leu Asn Lys Glu Phe Thr
1               5                   10

<210> SEQ ID NO 125
<211> LENGTH: 9
<212> TYPE: PRT
<213> ORGANISM: Epstein Barr Virus

<400> SEQUENCE: 125

Leu Val Ser Asp Tyr Cys Asn Val Leu
1               5

<210> SEQ ID NO 126
<211> LENGTH: 10
<212> TYPE: PRT
<213> ORGANISM: Epstein Barr Virus

<400> SEQUENCE: 126

Asp Tyr Cys Asn Val Leu Asn Lys Glu Phe
1               5                   10

-continued

<210> SEQ ID NO 127
<211> LENGTH: 9
<212> TYPE: PRT
<213> ORGANISM: Epstein Barr Virus

<400> SEQUENCE: 127

Ala Glu Asn Ala Gly Asn Asp Ala Cys
1               5

<210> SEQ ID NO 128
<211> LENGTH: 16
<212> TYPE: PRT
<213> ORGANISM: Epstein Barr Virus

<400> SEQUENCE: 128

Ile Ala Cys Pro Ile Val Met Arg Tyr Tyr Val Leu Asp His Leu Ile
1               5                   10                  15

<210> SEQ ID NO 129
<211> LENGTH: 9
<212> TYPE: PRT
<213> ORGANISM: Epstein Barr Virus

<400> SEQUENCE: 129

Tyr Val Leu Asp His Leu Ile Val Val
1               5

<210> SEQ ID NO 130
<211> LENGTH: 15
<212> TYPE: PRT
<213> ORGANISM: Epstein Barr Virus

<400> SEQUENCE: 130

Phe Phe Ile Gln Ala Pro Ser Asn Arg Val Met Ile Pro Ala Thr
1               5                   10                  15

<210> SEQ ID NO 131
<211> LENGTH: 9
<212> TYPE: PRT
<213> ORGANISM: Epstein Barr Virus

<400> SEQUENCE: 131

Ala Thr Ile Gly Thr Ala Met Tyr Lys
1               5

<210> SEQ ID NO 132
<211> LENGTH: 15
<212> TYPE: PRT
<213> ORGANISM: Epstein Barr Virus

<400> SEQUENCE: 132

Lys His Ser Arg Val Arg Ala Tyr Thr Tyr Ser Lys Val Leu Gly
1               5                   10                  15

<210> SEQ ID NO 133
<211> LENGTH: 15
<212> TYPE: PRT
<213> ORGANISM: Epstein Barr Virus

<400> SEQUENCE: 133

Arg Ala Leu Ile Lys Thr Leu Pro Arg Ala Ser Tyr Ser Ser His
1               5                   10                  15

```
<210> SEQ ID NO 134
<211> LENGTH: 15
<212> TYPE: PRT
<213> ORGANISM: Epstein Barr Virus

<400> SEQUENCE: 134

Glu Arg Pro Ile Phe Pro His Pro Ser Lys Pro Thr Phe Leu Pro
1               5                   10                  15

<210> SEQ ID NO 135
<211> LENGTH: 14
<212> TYPE: PRT
<213> ORGANISM: Epstein Barr Virus

<400> SEQUENCE: 135

Gln Lys Glu Glu Ala Ala Ile Cys Gly Gln Met Asp Leu Ser
1               5                   10

<210> SEQ ID NO 136
<211> LENGTH: 15
<212> TYPE: PRT
<213> ORGANISM: Epstein Barr Virus

<400> SEQUENCE: 136

Glu Val Cys Gln Pro Lys Arg Ile Arg Pro Phe His Pro Pro Gly
1               5                   10                  15

<210> SEQ ID NO 137
<211> LENGTH: 13
<212> TYPE: PRT
<213> ORGANISM: Epstein Barr Virus

<400> SEQUENCE: 137

Leu Pro Glu Pro Leu Pro Gln Gly Gln Leu Thr Ala Tyr
1               5                   10

<210> SEQ ID NO 138
<211> LENGTH: 11
<212> TYPE: PRT
<213> ORGANISM: Epstein Barr Virus

<400> SEQUENCE: 138

Glu Pro Leu Pro Gln Gly Gln Leu Thr Ala Tyr
1               5                   10

<210> SEQ ID NO 139
<211> LENGTH: 9
<212> TYPE: PRT
<213> ORGANISM: Epstein Barr Virus

<400> SEQUENCE: 139

Ala Pro Glu Asn Ala Tyr Gln Ala Tyr
1               5

<210> SEQ ID NO 140
<211> LENGTH: 9
<212> TYPE: PRT
<213> ORGANISM: Epstein Barr Virus

<400> SEQUENCE: 140

Leu Gln His Tyr Arg Glu Val Ala Ala
1               5

<210> SEQ ID NO 141
<211> LENGTH: 12
```

<212> TYPE: PRT
<213> ORGANISM: Epstein Barr Virus

<400> SEQUENCE: 141

Asp Ser Glu Leu Glu Ile Lys Arg Tyr Lys Asn Arg
1               5                   10

<210> SEQ ID NO 142
<211> LENGTH: 16
<212> TYPE: PRT
<213> ORGANISM: Epstein Barr Virus

<400> SEQUENCE: 142

Arg Lys Cys Cys Arg Ala Lys Phe Lys Gln Leu Leu Gln His Tyr Arg
1               5                   10                  15

<210> SEQ ID NO 143
<211> LENGTH: 8
<212> TYPE: PRT
<213> ORGANISM: Epstein Barr Virus

<400> SEQUENCE: 143

Arg Ala Lys Phe Lys Gln Leu Leu
1               5

<210> SEQ ID NO 144
<211> LENGTH: 9
<212> TYPE: PRT
<213> ORGANISM: Epstein Barr Virus

<400> SEQUENCE: 144

Ser Glu Asn Asp Arg Leu Arg Leu Leu
1               5

<210> SEQ ID NO 145
<211> LENGTH: 9
<212> TYPE: PRT
<213> ORGANISM: Epstein Barr Virus

<400> SEQUENCE: 145

Lys Asp Thr Trp Leu Asp Ala Arg Met
1               5

<210> SEQ ID NO 146
<211> LENGTH: 9
<212> TYPE: PRT
<213> ORGANISM: Epstein Barr Virus

<400> SEQUENCE: 146

Gly Leu Cys Thr Leu Val Ala Met Leu
1               5

<210> SEQ ID NO 147
<211> LENGTH: 9
<212> TYPE: PRT
<213> ORGANISM: Epstein Barr Virus

<400> SEQUENCE: 147

Asp Glu Val Glu Phe Leu Gly His Tyr
1               5

<210> SEQ ID NO 148
<211> LENGTH: 10
<212> TYPE: PRT
<213> ORGANISM: Epstein Barr Virus

<400> SEQUENCE: 148

Ser Arg Leu Val Arg Ala Ile Leu Ser Pro
1               5                  10

<210> SEQ ID NO 149
<211> LENGTH: 9
<212> TYPE: PRT
<213> ORGANISM: Epstein Barr Virus

<400> SEQUENCE: 149

Cys Tyr Asp His Ala Gln Thr His Leu
1               5

<210> SEQ ID NO 150
<211> LENGTH: 15
<212> TYPE: PRT
<213> ORGANISM: Epstein Barr Virus

<400> SEQUENCE: 150

Phe Arg Asn Leu Ala Tyr Gly Arg Thr Cys Val Leu Gly Lys Glu
1               5                  10                  15

<210> SEQ ID NO 151
<211> LENGTH: 13
<212> TYPE: PRT
<213> ORGANISM: Epstein Barr Virus

<400> SEQUENCE: 151

Arg Pro Gln Gly Gly Ser Arg Pro Glu Phe Val Lys Leu
1               5                  10

<210> SEQ ID NO 152
<211> LENGTH: 9
<212> TYPE: PRT
<213> ORGANISM: Epstein Barr Virus

<400> SEQUENCE: 152

Thr Leu Asp Tyr Lys Pro Leu Ser Val
1               5

<210> SEQ ID NO 153
<211> LENGTH: 9
<212> TYPE: PRT
<213> ORGANISM: Epstein Barr Virus

<400> SEQUENCE: 153

Tyr Arg Ser Gly Ile Ile Ala Val Val
1               5

<210> SEQ ID NO 154
<211> LENGTH: 10
<212> TYPE: PRT
<213> ORGANISM: Epstein Barr Virus

<400> SEQUENCE: 154

Leu Pro Leu Asp Leu Ser Val Ile Leu Phe
1               5                  10

<210> SEQ ID NO 155
<211> LENGTH: 9
<212> TYPE: PRT
<213> ORGANISM: Epstein Barr Virus

<400> SEQUENCE: 155

Leu Leu Trp Ala Ala Arg Pro Arg Leu
1               5

<210> SEQ ID NO 156
<211> LENGTH: 9
<212> TYPE: PRT
<213> ORGANISM: Epstein Barr Virus

<400> SEQUENCE: 156

Arg Arg Leu Val Val Thr Leu Gln Cys
1               5

<210> SEQ ID NO 157
<211> LENGTH: 9
<212> TYPE: PRT
<213> ORGANISM: Epstein Barr Virus

<400> SEQUENCE: 157

Ala Arg Tyr Ala Tyr Tyr Leu Gln Phe
1               5

<210> SEQ ID NO 158
<211> LENGTH: 9
<212> TYPE: PRT
<213> ORGANISM: Epstein Barr Virus

<400> SEQUENCE: 158

Arg Arg Arg Lys Gly Trp Ile Pro Leu
1               5

<210> SEQ ID NO 159
<211> LENGTH: 9
<212> TYPE: PRT
<213> ORGANISM: Epstein Barr Virus

<400> SEQUENCE: 159

Val Leu Gln Trp Ala Ser Leu Ala Val
1               5

<210> SEQ ID NO 160
<211> LENGTH: 9
<212> TYPE: PRT
<213> ORGANISM: Epstein Barr Virus

<400> SEQUENCE: 160

Phe Leu Asp Lys Gly Thr Tyr Thr Leu
1               5

<210> SEQ ID NO 161
<211> LENGTH: 9
<212> TYPE: PRT
<213> ORGANISM: Epstein Barr Virus

<400> SEQUENCE: 161

Ile Leu Ile Tyr Asn Gly Trp Tyr Ala
1               5

<210> SEQ ID NO 162
<211> LENGTH: 9
<212> TYPE: PRT
<213> ORGANISM: Epstein Barr Virus

<400> SEQUENCE: 162

Val Pro Gly Ser Glu Thr Met Cys Tyr

```
<210> SEQ ID NO 163
<211> LENGTH: 9
<212> TYPE: PRT
<213> ORGANISM: Epstein Barr Virus

<400> SEQUENCE: 163

Ala Pro Gly Trp Leu Ile Trp Thr Tyr
1               5

<210> SEQ ID NO 164
<211> LENGTH: 9
<212> TYPE: PRT
<213> ORGANISM: Epstein Barr Virus

<400> SEQUENCE: 164

Thr Leu Phe Ile Gly Ser His Val Val
1               5

<210> SEQ ID NO 165
<211> LENGTH: 9
<212> TYPE: PRT
<213> ORGANISM: Epstein Barr Virus

<400> SEQUENCE: 165

Ser Leu Val Ile Val Thr Thr Phe Val
1               5

<210> SEQ ID NO 166
<211> LENGTH: 9
<212> TYPE: PRT
<213> ORGANISM: Epstein Barr Virus

<400> SEQUENCE: 166

Leu Met Ile Ile Pro Leu Ile Asn Val
1               5

<210> SEQ ID NO 167
<211> LENGTH: 15
<212> TYPE: PRT
<213> ORGANISM: Epstein Barr Virus

<400> SEQUENCE: 167

Arg Arg Pro Gln Lys Arg Pro Ser Cys Ile Gly Cys Lys Gly Thr
1               5                   10                  15

<210> SEQ ID NO 168
<211> LENGTH: 15
<212> TYPE: PRT
<213> ORGANISM: Epstein Barr Virus

<400> SEQUENCE: 168

Arg Pro Phe Phe His Pro Val Gly Glu Ala Asp Tyr Phe Glu Tyr
1               5                   10                  15

<210> SEQ ID NO 169
<211> LENGTH: 20
<212> TYPE: PRT
<213> ORGANISM: Epstein Barr Virus

<400> SEQUENCE: 169

Val Pro Pro Gly Ala Ile Glu Gln Gly Pro Ala Asp Asp Pro Gly Glu
1               5                   10                  15
```

Gly Pro Ser Thr
            20

<210> SEQ ID NO 170
<211> LENGTH: 25
<212> TYPE: PRT
<213> ORGANISM: Epstein Barr Virus

<400> SEQUENCE: 170

Ile Glu Gln Gly Pro Thr Asp Asp Pro Gly Glu Gly Pro Ser Thr Gly
1               5                   10                  15

Pro Arg Gly Gln Gly Asp Gly Gly Arg
            20                  25

<210> SEQ ID NO 171
<211> LENGTH: 15
<212> TYPE: PRT
<213> ORGANISM: Epstein Barr Virus

<400> SEQUENCE: 171

Asp Gly Gly Arg Arg Lys Lys Gly Gly Trp Phe Gly Arg His Arg
1               5                   10                  15

<210> SEQ ID NO 172
<211> LENGTH: 20
<212> TYPE: PRT
<213> ORGANISM: Epstein Barr Virus

<400> SEQUENCE: 172

Ser Asn Pro Lys Phe Glu Asn Ile Ala Glu Gly Leu Arg Val Leu Leu
1               5                   10                  15

Ala Arg Ser His
            20

<210> SEQ ID NO 173
<211> LENGTH: 15
<212> TYPE: PRT
<213> ORGANISM: Epstein Barr Virus

<400> SEQUENCE: 173

Asn Pro Lys Phe Glu Asn Ile Ala Glu Gly Leu Arg Ala Leu Leu
1               5                   10                  15

<210> SEQ ID NO 174
<211> LENGTH: 20
<212> TYPE: PRT
<213> ORGANISM: Epstein Barr Virus

<400> SEQUENCE: 174

Glu Asn Ile Ala Glu Gly Leu Arg Val Leu Leu Ala Arg Ser His Val
1               5                   10                  15

Glu Arg Thr Thr
            20

<210> SEQ ID NO 175
<211> LENGTH: 20
<212> TYPE: PRT
<213> ORGANISM: Epstein Barr Virus

<400> SEQUENCE: 175

Ile Ala Glu Gly Leu Arg Ala Leu Leu Ala Arg Ser His Val Glu Arg
1               5                   10                  15

Thr Thr Asp Glu

```
<210> SEQ ID NO 176
<211> LENGTH: 15
<212> TYPE: PRT
<213> ORGANISM: Epstein Barr Virus

<400> SEQUENCE: 176

Leu Arg Ala Leu Leu Ala Arg Ser His Val Glu Arg Thr Thr Asp
1               5                   10                  15

<210> SEQ ID NO 177
<211> LENGTH: 25
<212> TYPE: PRT
<213> ORGANISM: Epstein Barr Virus

<400> SEQUENCE: 177

Glu Glu Gly Asn Trp Val Ala Gly Val Phe Val Tyr Gly Gly Ser Lys
1               5                   10                  15

Thr Ser Leu Tyr Asn Leu Arg Arg Gly
            20                  25

<210> SEQ ID NO 178
<211> LENGTH: 20
<212> TYPE: PRT
<213> ORGANISM: Epstein Barr Virus

<400> SEQUENCE: 178

Val Tyr Gly Gly Ser Lys Thr Ser Leu Tyr Asn Leu Arg Arg Gly Thr
1               5                   10                  15

Ala Leu Ala Ile
            20

<210> SEQ ID NO 179
<211> LENGTH: 14
<212> TYPE: PRT
<213> ORGANISM: Epstein Barr Virus

<400> SEQUENCE: 179

Thr Ser Leu Tyr Asn Leu Arg Arg Gly Thr Ala Leu Ala Ile
1               5                   10

<210> SEQ ID NO 180
<211> LENGTH: 13
<212> TYPE: PRT
<213> ORGANISM: Epstein Barr Virus

<400> SEQUENCE: 180

Tyr Asn Leu Arg Arg Gly Thr Ala Leu Ala Ile Pro Gln
1               5                   10

<210> SEQ ID NO 181
<211> LENGTH: 16
<212> TYPE: PRT
<213> ORGANISM: Epstein Barr Virus

<400> SEQUENCE: 181

Asn Leu Arg Arg Gly Arg Thr Ala Leu Ala Ile Pro Gln Cys Arg Leu
1               5                   10                  15

<210> SEQ ID NO 182
<211> LENGTH: 25
<212> TYPE: PRT
<213> ORGANISM: Epstein Barr Virus
```

-continued

<400> SEQUENCE: 182

Glu Glu Gly Asn Trp Val Ala Gly Val Phe Val Tyr Gly Gly Ser Lys
1               5                   10                  15

Thr Ser Leu Tyr Asn Leu Arg Arg Gly
            20                  25

<210> SEQ ID NO 183
<211> LENGTH: 15
<212> TYPE: PRT
<213> ORGANISM: Epstein Barr Virus

<400> SEQUENCE: 183

Ala Ile Pro Gln Cys Arg Leu Thr Pro Leu Ser Arg Leu Pro Phe
1               5                   10                  15

<210> SEQ ID NO 184
<211> LENGTH: 15
<212> TYPE: PRT
<213> ORGANISM: Epstein Barr Virus

<400> SEQUENCE: 184

Pro Gln Cys Arg Leu Thr Pro Leu Ser Arg Leu Pro Phe Gly Met
1               5                   10                  15

<210> SEQ ID NO 185
<211> LENGTH: 18
<212> TYPE: PRT
<213> ORGANISM: Epstein Barr Virus

<400> SEQUENCE: 185

Ala Pro Gly Pro Gly Pro Gln Pro Leu Arg Glu Ser Ile Val Cys Tyr
1               5                   10                  15

Phe Met

<210> SEQ ID NO 186
<211> LENGTH: 20
<212> TYPE: PRT
<213> ORGANISM: Epstein Barr Virus

<400> SEQUENCE: 186

Pro Gln Pro Gly Pro Leu Arg Glu Ser Ile Val Cys Tyr Phe Met Val
1               5                   10                  15

Phe Leu Gln Thr
            20

<210> SEQ ID NO 187
<211> LENGTH: 20
<212> TYPE: PRT
<213> ORGANISM: Epstein Barr Virus

<400> SEQUENCE: 187

Pro Gly Pro Leu Arg Glu Ser Ile Val Cys Tyr Phe Met Val Phe Leu
1               5                   10                  15

Gln Thr His Ile
            20

<210> SEQ ID NO 188
<211> LENGTH: 20
<212> TYPE: PRT
<213> ORGANISM: Epstein Barr Virus

<400> SEQUENCE: 188

```
Leu Arg Glu Ser Ile Val Cys Tyr Phe Met Val Phe Leu Gln Thr His
1               5                   10                  15

Ile Phe Ala Glu
            20

<210> SEQ ID NO 189
<211> LENGTH: 25
<212> TYPE: PRT
<213> ORGANISM: Epstein Barr Virus

<400> SEQUENCE: 189

Leu Arg Glu Ser Ile Val Cys Tyr Phe Met Val Phe Leu Gln Thr His
1               5                   10                  15

Ile Phe Ala Glu Val Leu Lys Asp Ala
            20                  25

<210> SEQ ID NO 190
<211> LENGTH: 13
<212> TYPE: PRT
<213> ORGANISM: Epstein Barr Virus

<400> SEQUENCE: 190

Tyr Phe Met Val Phe Leu Gln Thr His Ile Phe Ala Glu
1               5                   10

<210> SEQ ID NO 191
<211> LENGTH: 15
<212> TYPE: PRT
<213> ORGANISM: Epstein Barr Virus

<400> SEQUENCE: 191

Met Val Phe Leu Gln Thr His Ile Phe Ala Glu Val Leu Lys Asp
1               5                   10                  15

<210> SEQ ID NO 192
<211> LENGTH: 19
<212> TYPE: PRT
<213> ORGANISM: Epstein Barr Virus

<400> SEQUENCE: 192

Val Phe Leu Gln Thr His Ile Phe Ala Glu Val Leu Lys Asp Ala Ile
1               5                   10                  15

Lys Asp Leu

<210> SEQ ID NO 193
<211> LENGTH: 20
<212> TYPE: PRT
<213> ORGANISM: Epstein Barr Virus

<400> SEQUENCE: 193

Val Leu Lys Asp Ala Ile Lys Asp Leu Val Met Thr Lys Pro Ala Pro
1               5                   10                  15

Thr Cys Asn Ile
            20

<210> SEQ ID NO 194
<211> LENGTH: 25
<212> TYPE: PRT
<213> ORGANISM: Epstein Barr Virus

<400> SEQUENCE: 194

Pro Thr Cys Asn Ile Lys Val Thr Val Cys Ser Phe Asp Asp Gly Val
```

```
                1               5                  10                  15

Asp Leu Pro Pro Trp Phe Pro Pro Met
            20                  25

<210> SEQ ID NO 195
<211> LENGTH: 20
<212> TYPE: PRT
<213> ORGANISM: Epstein Barr Virus

<400> SEQUENCE: 195

Arg Val Thr Val Cys Ser Phe Asp Asp Gly Val Asp Leu Pro Pro Trp
1               5                   10                  15

Phe Pro Pro Met
            20

<210> SEQ ID NO 196
<211> LENGTH: 13
<212> TYPE: PRT
<213> ORGANISM: Epstein Barr Virus

<400> SEQUENCE: 196

Pro Pro Trp Phe Pro Pro Met Val Glu Gly Ala Ala Ala
1               5                   10

<210> SEQ ID NO 197
<211> LENGTH: 20
<212> TYPE: PRT
<213> ORGANISM: Epstein Barr Virus

<400> SEQUENCE: 197

Gly Gln Thr Tyr His Leu Ile Val Asp Thr Leu Ala Leu His Gly Gly
1               5                   10                  15

Gln Thr Tyr His
            20

<210> SEQ ID NO 198
<211> LENGTH: 20
<212> TYPE: PRT
<213> ORGANISM: Epstein Barr Virus

<400> SEQUENCE: 198

Ile Pro Leu Thr Ile Phe Val Gly Glu Asn Thr Gly Val Pro Pro Pro
1               5                   10                  15

Leu Pro Pro Pro
            20

<210> SEQ ID NO 199
<211> LENGTH: 20
<212> TYPE: PRT
<213> ORGANISM: Epstein Barr Virus

<400> SEQUENCE: 199

Met Arg Met Leu Trp Met Ala Asn Tyr Ile Val Arg Gln Ser Arg Gly
1               5                   10                  15

Asp Arg Gly Leu
            20

<210> SEQ ID NO 200
<211> LENGTH: 19
<212> TYPE: PRT
<213> ORGANISM: Epstein Barr Virus

<400> SEQUENCE: 200
```

```
Leu Pro Pro Ala Thr Leu Val Pro Pro Arg Pro Thr Arg Pro Thr Thr
1               5                   10                  15

Leu Pro Pro

<210> SEQ ID NO 201
<211> LENGTH: 19
<212> TYPE: PRT
<213> ORGANISM: Epstein Barr Virus

<400> SEQUENCE: 201

Pro Arg Ser Thr Val Phe Tyr Asn Ile Pro Pro Met Pro Leu Pro Pro
1               5                   10                  15

Ser Gln Leu

<210> SEQ ID NO 202
<211> LENGTH: 11
<212> TYPE: PRT
<213> ORGANISM: Epstein Barr Virus

<400> SEQUENCE: 202

Thr Val Phe Tyr Asn Ile Pro Pro Met Pro Leu
1               5                   10

<210> SEQ ID NO 203
<211> LENGTH: 20
<212> TYPE: PRT
<213> ORGANISM: Epstein Barr Virus

<400> SEQUENCE: 203

Pro Ala Gln Pro Pro Gly Val Ile Asn Asp Gln Gln Leu His His
1               5                   10                  15

Leu Pro Ser Gly
            20

<210> SEQ ID NO 204
<211> LENGTH: 20
<212> TYPE: PRT
<213> ORGANISM: Epstein Barr Virus

<400> SEQUENCE: 204

Glu Asp Leu Pro Cys Ile Val Ser Arg Gly Gly Pro Lys Val Lys Arg
1               5                   10                  15

Pro Pro Ile Phe
            20

<210> SEQ ID NO 205
<211> LENGTH: 20
<212> TYPE: PRT
<213> ORGANISM: Epstein Barr Virus

<400> SEQUENCE: 205

Gly Pro Trp Val Pro Glu Gln Trp Met Phe Gln Gly Ala Pro Pro Ser
1               5                   10                  15

Gln Gly Thr Pro
            20

<210> SEQ ID NO 206
<211> LENGTH: 19
<212> TYPE: PRT
<213> ORGANISM: Epstein Barr Virus

<400> SEQUENCE: 206
```

Gln Val Ala Asp Val Val Arg Ala Pro Gly Val Pro Ala Met Gln Pro
1               5                   10                  15

Gln Tyr Phe

<210> SEQ ID NO 207
<211> LENGTH: 14
<212> TYPE: PRT
<213> ORGANISM: Epstein Barr Virus

<400> SEQUENCE: 207

Asn Arg Gly Trp Met Gln Arg Ile Arg Arg Arg Arg Arg
1               5                   10

<210> SEQ ID NO 208
<211> LENGTH: 14
<212> TYPE: PRT
<213> ORGANISM: Epstein Barr Virus

<400> SEQUENCE: 208

Asn Arg Gly Trp Met Gln Arg Ile Arg Arg Arg Arg Arg
1               5                   10

<210> SEQ ID NO 209
<211> LENGTH: 21
<212> TYPE: PRT
<213> ORGANISM: Epstein Barr Virus

<400> SEQUENCE: 209

Pro His Asp Ile Thr Tyr Pro Tyr Thr Ala Arg Asn Ile Arg Asp Ala
1               5                   10                  15

Ala Cys Arg Ala Val
            20

<210> SEQ ID NO 210
<211> LENGTH: 15
<212> TYPE: PRT
<213> ORGANISM: Epstein Barr Virus

<400> SEQUENCE: 210

Ile Leu Cys Phe Val Met Ala Ala Arg Gln Arg Leu Gln Asp Ile
1               5                   10                  15

<210> SEQ ID NO 211
<211> LENGTH: 15
<212> TYPE: PRT
<213> ORGANISM: Epstein Barr Virus

<400> SEQUENCE: 211

Ser Asp Asp Glu Leu Pro Tyr Ile Asp Pro Asn Met Glu Pro Val
1               5                   10                  15

<210> SEQ ID NO 212
<211> LENGTH: 15
<212> TYPE: PRT
<213> ORGANISM: Epstein Barr Virus

<400> SEQUENCE: 212

Gln Gln Arg Pro Val Met Phe Val Ser Arg Val Pro Ala Lys Lys
1               5                   10                  15

<210> SEQ ID NO 213
<211> LENGTH: 15
<212> TYPE: PRT

<213> ORGANISM: Epstein Barr Virus

<400> SEQUENCE: 213

Gln Lys Arg Ala Ala Pro Pro Thr Val Ser Pro Ser Asp Thr Gly
1               5                   10                  15

<210> SEQ ID NO 214
<211> LENGTH: 15
<212> TYPE: PRT
<213> ORGANISM: Epstein Barr Virus

<400> SEQUENCE: 214

Pro Pro Ala Ala Gly Pro Pro Ala Ala Gly Pro Arg Ile Leu Ala
1               5                   10                  15

<210> SEQ ID NO 215
<211> LENGTH: 15
<212> TYPE: PRT
<213> ORGANISM: Epstein Barr Virus

<400> SEQUENCE: 215

Pro Pro Val Val Arg Met Phe Met Arg Glu Arg Gln Leu Pro Gln
1               5                   10                  15

<210> SEQ ID NO 216
<211> LENGTH: 15
<212> TYPE: PRT
<213> ORGANISM: Epstein Barr Virus

<400> SEQUENCE: 216

Pro Gln Cys Phe Trp Glu Met Arg Ala Gly Arg Glu Ile Thr Gln
1               5                   10                  15

<210> SEQ ID NO 217
<211> LENGTH: 20
<212> TYPE: PRT
<213> ORGANISM: Epstein Barr Virus

<400> SEQUENCE: 217

Pro Ala Pro Gln Ala Pro Tyr Gln Gly Tyr Gln Glu Pro Pro Ala Pro
1               5                   10                  15

Gln Ala Pro Tyr
            20

<210> SEQ ID NO 218
<211> LENGTH: 15
<212> TYPE: PRT
<213> ORGANISM: Epstein Barr Virus

<400> SEQUENCE: 218

Pro Ser Met Pro Phe Ala Ser Asp Tyr Ser Gln Gly Ala Phe Thr
1               5                   10                  15

<210> SEQ ID NO 219
<211> LENGTH: 16
<212> TYPE: PRT
<213> ORGANISM: Epstein Barr Virus

<400> SEQUENCE: 219

Ala Gln Glu Ile Leu Ser Asp Asn Ser Glu Ile Ser Val Phe Pro Lys
1               5                   10                  15

<210> SEQ ID NO 220
<211> LENGTH: 20

```
<212> TYPE: PRT
<213> ORGANISM: Epstein Barr Virus

<400> SEQUENCE: 220

Gly Pro Pro Arg Pro Pro Leu Gly Pro Pro Leu Ser Ser Ser Ile Gly
1               5                   10                  15

Leu Ala Leu Leu
            20

<210> SEQ ID NO 221
<211> LENGTH: 15
<212> TYPE: PRT
<213> ORGANISM: Epstein Barr Virus

<400> SEQUENCE: 221

Leu Trp Arg Leu Gly Ala Thr Ile Trp Gln Leu Leu Ala Phe Phe
1               5                   10                  15

<210> SEQ ID NO 222
<211> LENGTH: 20
<212> TYPE: PRT
<213> ORGANISM: Epstein Barr Virus

<400> SEQUENCE: 222

Leu Ile Trp Met Tyr Tyr His Gly Pro Arg His Thr Asp Glu His His
1               5                   10                  15

His Asp Asp Ser
            20

<210> SEQ ID NO 223
<211> LENGTH: 20
<212> TYPE: PRT
<213> ORGANISM: Epstein Barr Virus

<400> SEQUENCE: 223

Gln Ala Thr Asp Asp Ser Ser His Glu Ser Asp Ser Asn Ser Asn Glu
1               5                   10                  15

Gly Arg His His
            20

<210> SEQ ID NO 224
<211> LENGTH: 20
<212> TYPE: PRT
<213> ORGANISM: Epstein Barr Virus

<400> SEQUENCE: 224

Ser Ser His Glu Ser Asp Ser Asn Ser Asn Glu Gly Arg His His Leu
1               5                   10                  15

Leu Val Ser Gly
            20

<210> SEQ ID NO 225
<211> LENGTH: 16
<212> TYPE: PRT
<213> ORGANISM: Epstein Barr Virus

<400> SEQUENCE: 225

Ser Gly His Glu Ser Asp Ser Asn Ser Asn Glu Gly Arg His His His
1               5                   10                  15

<210> SEQ ID NO 226
<211> LENGTH: 15
<212> TYPE: PRT
```

<213> ORGANISM: Epstein Barr Virus

<400> SEQUENCE: 226

Thr Asp Gly Gly Gly His Ser His Asp Ser Gly His Gly Gly
1               5                   10                  15

<210> SEQ ID NO 227
<211> LENGTH: 15
<212> TYPE: PRT
<213> ORGANISM: Epstein Barr Virus

<400> SEQUENCE: 227

Asp Tyr Gln Pro Leu Gly Thr Gln Asp Gln Ser Leu Tyr Leu Gly
1               5                   10                  15

<210> SEQ ID NO 228
<211> LENGTH: 15
<212> TYPE: PRT
<213> ORGANISM: Epstein Barr Virus

<400> SEQUENCE: 228

Ser Thr Val Val Thr Ala Thr Gly Leu Ala Leu Ser Leu Leu Leu
1               5                   10                  15

<210> SEQ ID NO 229
<211> LENGTH: 14
<212> TYPE: PRT
<213> ORGANISM: Epstein Barr Virus

<400> SEQUENCE: 229

Ser Ser Tyr Ala Ala Ala Gln Arg Lys Leu Leu Thr Pro Val
1               5                   10

<210> SEQ ID NO 230
<211> LENGTH: 20
<212> TYPE: PRT
<213> ORGANISM: Epstein Barr Virus

<400> SEQUENCE: 230

Val Thr Phe Phe Ala Ile Cys Leu Thr Trp Arg Ile Glu Asp Pro Pro
1               5                   10                  15

Phe Asn Ser Ile
            20

<210> SEQ ID NO 231
<211> LENGTH: 20
<212> TYPE: PRT
<213> ORGANISM: Epstein Barr Virus

<400> SEQUENCE: 231

Ile Cys Leu Thr Trp Arg Ile Glu Asp Pro Pro Phe Asn Ser Ile Leu
1               5                   10                  15

Phe Ala Leu Leu
            20

<210> SEQ ID NO 232
<211> LENGTH: 20
<212> TYPE: PRT
<213> ORGANISM: Epstein Barr Virus

<400> SEQUENCE: 232

Val Leu Val Met Leu Val Leu Leu Ile Leu Ala Tyr Arg Arg Arg Trp
1               5                   10                  15

Arg Arg Leu Thr
            20

<210> SEQ ID NO 233
<211> LENGTH: 14
<212> TYPE: PRT
<213> ORGANISM: Epstein Barr Virus

<400> SEQUENCE: 233

Ser Thr Glu Phe Ile Pro Asn Leu Phe Cys Met Leu Leu Leu
1               5                   10

<210> SEQ ID NO 234
<211> LENGTH: 20
<212> TYPE: PRT
<213> ORGANISM: Epstein Barr Virus

<400> SEQUENCE: 234

Thr Tyr Gly Pro Val Phe Met Ser Leu Gly Gly Leu Leu Thr Met Val
1               5                   10                  15

Ala Gly Ala Val
            20

<210> SEQ ID NO 235
<211> LENGTH: 19
<212> TYPE: PRT
<213> ORGANISM: Epstein Barr Virus

<400> SEQUENCE: 235

Ala Gly Leu Thr Leu Ser Leu Leu Val Ile Cys Ser Tyr Leu Phe Ile
1               5                   10                  15

Ser Arg Gly

<210> SEQ ID NO 236
<211> LENGTH: 12
<212> TYPE: PRT
<213> ORGANISM: Epstein Barr Virus

<400> SEQUENCE: 236

Pro Tyr Tyr Val Val Asp Leu Ser Val Arg Gly Met
1               5                   10

<210> SEQ ID NO 237
<211> LENGTH: 13
<212> TYPE: PRT
<213> ORGANISM: Epstein Barr Virus

<400> SEQUENCE: 237

Thr Val Val Leu Arg Tyr His Val Leu Leu Glu Glu Ile
1               5                   10

<210> SEQ ID NO 238
<211> LENGTH: 15
<212> TYPE: PRT
<213> ORGANISM: Epstein Barr Virus

<400> SEQUENCE: 238

Glu Leu Glu Ile Lys Arg Tyr Lys Asn Arg Val Ala Ser Arg Lys
1               5                   10                  15

<210> SEQ ID NO 239
<211> LENGTH: 15
<212> TYPE: PRT
<213> ORGANISM: Epstein Barr Virus

<400> SEQUENCE: 239

Lys Ser Ser Glu Asn Asp Arg Leu Arg Leu Leu Leu Lys Gln Met
1               5                   10                  15

<210> SEQ ID NO 240
<211> LENGTH: 20
<212> TYPE: PRT
<213> ORGANISM: Epstein Barr Virus

<400> SEQUENCE: 240

Leu Asp Leu Phe Gly Gln Leu Thr Pro His Thr Lys Ala Val Tyr Gln
1               5                   10                  15

Pro Arg Gly Ala
            20

<210> SEQ ID NO 241
<211> LENGTH: 15
<212> TYPE: PRT
<213> ORGANISM: Epstein Barr Virus

<400> SEQUENCE: 241

Phe Gly Gln Leu Thr Pro His Thr Lys Ala Val Tyr Gln Pro Arg
1               5                   10                  15

<210> SEQ ID NO 242
<211> LENGTH: 15
<212> TYPE: PRT
<213> ORGANISM: Epstein Barr Virus

<400> SEQUENCE: 242

Val Tyr Phe Gln Asp Val Phe Gly Thr Met Trp Cys His His Ala
1               5                   10                  15

<210> SEQ ID NO 243
<211> LENGTH: 8
<212> TYPE: PRT
<213> ORGANISM: Epstein Barr Virus

<400> SEQUENCE: 243

Asp Asn Cys Asn Ser Thr Asn Ile
1               5

<210> SEQ ID NO 244
<211> LENGTH: 13
<212> TYPE: PRT
<213> ORGANISM: Epstein Barr Virus

<400> SEQUENCE: 244

Thr Ala Val Val Arg Ala Gln Gly Leu Asp Val Thr Leu
1               5                   10

<210> SEQ ID NO 245
<211> LENGTH: 15
<212> TYPE: PRT
<213> ORGANISM: Epstein Barr Virus

<400> SEQUENCE: 245

Ala Trp Cys Leu Glu Gln Lys Arg Gln Asn Met Val Leu Arg Glu
1               5                   10                  15

<210> SEQ ID NO 246
<211> LENGTH: 15
<212> TYPE: PRT

```
<213> ORGANISM: Epstein Barr Virus

<400> SEQUENCE: 246

Asp Asn Glu Ile Phe Leu Thr Lys Lys Met Thr Glu Val Cys Gln
1               5                   10                  15

<210> SEQ ID NO 247
<211> LENGTH: 9
<212> TYPE: PRT
<213> ORGANISM: Influenza Virus

<400> SEQUENCE: 247

Gly Ile Leu Gly Phe Val Phe Thr Leu
1               5

<210> SEQ ID NO 248
<211> LENGTH: 9
<212> TYPE: PRT
<213> ORGANISM: Influenza Virus

<400> SEQUENCE: 248

Asn Met Leu Ser Thr Val Leu Gly Val
1               5

<210> SEQ ID NO 249
<211> LENGTH: 9
<212> TYPE: PRT
<213> ORGANISM: Influenza Virus

<400> SEQUENCE: 249

Cys Val Asn Gly Ser Cys Phe Thr Val
1               5

<210> SEQ ID NO 250
<211> LENGTH: 9
<212> TYPE: PRT
<213> ORGANISM: Influenza Virus

<400> SEQUENCE: 250

Ser Leu Glu Asn Phe Arg Ala Tyr Val
1               5

<210> SEQ ID NO 251
<211> LENGTH: 10
<212> TYPE: PRT
<213> ORGANISM: Influenza Virus

<400> SEQUENCE: 251

Ile Met Asp Lys Asn Ile Ile Leu Lys Ala
1               5                   10

<210> SEQ ID NO 252
<211> LENGTH: 10
<212> TYPE: PRT
<213> ORGANISM: Influenza Virus

<400> SEQUENCE: 252

Ser Leu Cys Pro Ile Arg Gly Trp Ala Ile
1               5                   10

<210> SEQ ID NO 253
<211> LENGTH: 9
<212> TYPE: PRT
<213> ORGANISM: Influenza Virus
```

```
<400> SEQUENCE: 253

Phe Met Tyr Ser Asp Phe His Phe Ile
1               5

<210> SEQ ID NO 254
<211> LENGTH: 9
<212> TYPE: PRT
<213> ORGANISM: Cytomegalovirus

<400> SEQUENCE: 254

Asn Leu Val Pro Met Val Ala Thr Val
1               5

<210> SEQ ID NO 255
<211> LENGTH: 9
<212> TYPE: PRT
<213> ORGANISM: Measles Virus

<400> SEQUENCE: 255

Leu Met Ile Asp Arg Pro Tyr Val Leu
1               5

<210> SEQ ID NO 256
<211> LENGTH: 9
<212> TYPE: PRT
<213> ORGANISM: Measles Virus

<400> SEQUENCE: 256

Ile Leu Gly Gln Asp Leu Gln Tyr Val
1               5

<210> SEQ ID NO 257
<211> LENGTH: 9
<212> TYPE: PRT
<213> ORGANISM: Measles Virus

<400> SEQUENCE: 257

Lys Leu Trp Cys Arg His Phe Cys Val
1               5

<210> SEQ ID NO 258
<211> LENGTH: 9
<212> TYPE: PRT
<213> ORGANISM: Measles Virus

<400> SEQUENCE: 258

Lys Leu Trp Glu Ser Pro Gln Glu Ile
1               5
```

ANTIGEN-SPECIFIC T CELL REDIRECTORS

This application claims priority to Ser. No. 61/765,263 filed on Feb. 15, 2013 and to Ser. No. 61/783,852 filed on Mar. 14, 2013 and incorporates each of these applications by reference.

This application incorporates by reference the contents of a text file having the size of 40,800 bytes created on Sep. 11, 2019 and named "C12253sequencelisting.txt," which is the sequence listing for this application.

This invention was made with government support under AI072677 and CA108835 by the National Institutes of Health. The government has certain rights in the invention.

TECHNICAL FIELD

This disclosure relates generally to immunotherapy.

BRIEF DESCRIPTION OF THE DRAWINGS

FIG. 2A. Schematic of an experimental set up for a conjugation assay. FIG. 2B. Flow cytometry data from an example of a conjugate formation assay. PKH-labeled cells were co-cultured with indicated beads at 4° C. overnight at a 1:1 E:T ratio. Control beads were beads with immobilized IgG$_1$ mAb isotype control antibodies. FIG. 2C. Summary of 2-12 independent conjugation assays conducted with T2 target cells and 2C effector cells. "K$^b$-SIY" represents beads made with SIY peptide loaded K$^b$-Ig dimer instead of 1B2. (*=p<0.01, **=p<0.001)

FIG. 3A. To test the specificity of pre-targeted 1B2/CD19 redirection bead binding 0.2×10$^6$ CD8$^+$ 2C and Pmel T cells were incubated with 50 µl of beads at 4° C. for the duration displayed. After incubation, cells were washed and counterstained with anti-mouse IgG$_1$ PE. FIG. 3B. To test the stability of a 1B2/CD19 redirection bead pre-targeting, 0.2×10$^6$ CD8$^+$ 2C T cell were stained at 4° C. for 15 minutes (left most line) with 50 µl beads, washed and subsequently transferred at 37° C. After indicated time points cells were counterstained with anti-mouse IgG$_1$ PE to identify unbound beads. FIG. 3C. Impact of 1B2 redirection bead:cell ratio on staining intensity. Either different amounts of cells (left panel) were pre-targeted with 50 µl beads or 0.2×10$^6$ CD8$^+$ 2C cells (right panel) were pre-targeted with different amounts of beads. Pre-targeting was performed at 4° C. for 15 minutes. Cells were washed and counterstained with anti-mouse IgG$_1$ PE.

FIGS. 4A-B. Antibody targeting of a high affinity TCR by antibody-based redirection beads (Example 5). FIG. 4A. 2C CD8$^+$ T cell-redirected specific lysis of T2 cells mediated by 1B2 (control) and 1B2/CD19 (redirection) beads was determined by $^{51}$Cr release assay. A co-culture protocol (left panel) was compared to a pre-target protocol (right panel) at different E:T ratios. Data displayed represents specific lysis, with background (cells only) subtracted. FIG. 4B. Comparison of 1B2/CD19 specific lysis using either a co-culture or a pre-targeted protocol. Data displayed represent the 1B2-subtracted 1B2/CD19-induced specific redirection lysis of T2 target cells at different E:T ratios.

FIG. 5A. Engagement of a high affinity TCR on CD8$^+$ 2C T cells with L$^d$-QL9-Ig based redirection beads. L$^d$-QL9-Ig and CD19 only beads served as redirection control. Data displayed in line (upper panel) and bar (lower panel) graphs represents specific lysis of T2 cells derived from the same experiment, with background (cells only) subtracted. FIG. 5B. Engagement of a low affinity tumor TCR on CD8$^+$ Pmel T cells with D$^b$-gp100-Ig based redirection beads. D$^b$-gp100-Ig only beads served as redirection control. "K$^b$-OVA-Ig" and "K$^b$-OVA-Ig/CD19" beads represent non-cognate controls for D$^b$-gp100-Ig/CD19-mediated redirected lysis. Data displayed in line (upper panel) and bar (lower panel) graphs represents specific lysis of T2 cells derived from the same experiment, with background (cells only) subtracted. Specific lysis was determined by $^{51}$Cr release assay at indicated E:T ratios.

DETAILED DESCRIPTION

Figure 1A:
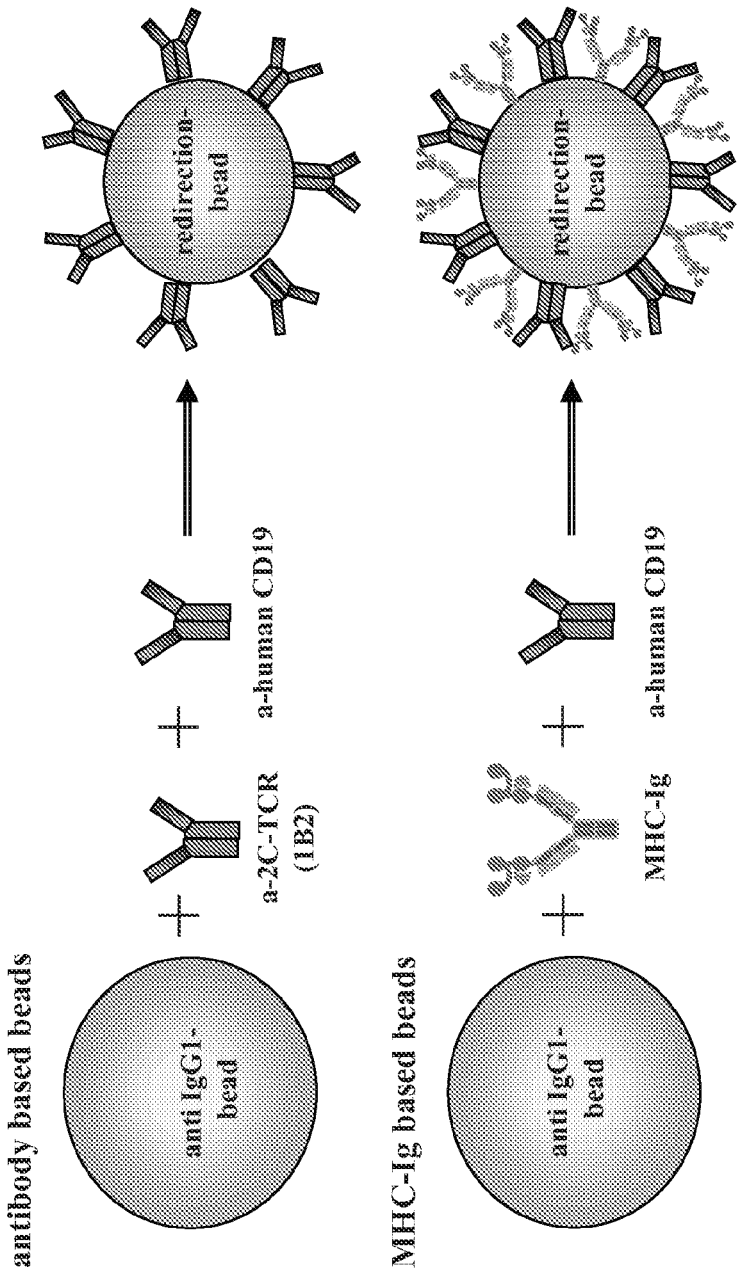
FIG. 1A. Schematics showing preparation of clonotypic antibody-based and MHC-Ig-based redirection beads (Example 1). Anti-mouse-IgG$_1$ microbeads were incubated with anti-human CD19 mAb and with either 2C-TCR clonotypic antibody (1B2) or with peptide loaded MHC-Ig molecules. Control beads were incubated with only one of 1B2, MHC-Ig, or CD19 antibody. Additional control beads were generated using an IgG$_1$ mAb isotype control.

Antibodies and antibody-like molecules have emerged as a major clinically important therapeutic modality for treatment of autoimmunity, inflammation and cancer. There are currently more than 25 approved antibodies and hundreds more in clinical trials.

Monoclonal Antibodies (mAbs) have been the main focus of immunotherapeutic efforts because they target their specific antigen in vivo at high affinities and with superior specificity (Köhler, G. & Milstein, C., Nature 256, 495-497, 1975). Many of these mAbs have been modulated to decrease immunogenicity (Isaacs, J. D.; Lancet 340, 748-752, 1992) and to increase affinity (Maynard, J. & Georgiou, G., Annu. Rev. Biomed. Eng. 2, 339-376, 2000). Based on these advances, mAbs have become an essential part of the therapeutic regimen for several types of hematologic malignancy, breast cancer, and colon cancer (Adams, G. P., Nat. Biotechnol. 2005, 23, 1147-1157; Duebel, S. Handbook of Therapeutic Antibodies; Wiley-VCH Verlag GmbH & Co. KGaA:Weinheim, Germany, 2007; Weiner, L. M.; Lancet 2009, 373, 1033-40). Response rates, however, are sometimes low, and relapse is a serious problem.

While a primary focus of increasing potency has been to increase affinity and specificity of targeting antibodies, a complementary approach has been to endow antibodies with new properties. These approaches include the development of immunotoxins, radio-immunoconjugates, bispecific immunoglobulins, bispecific single-chain Fv antibodies and tandem single chain triplebodies (Kellner, C., J. Immunother. 2008, 31, 871-884; Kugler, M., Br. J. Haematol. 2010, 150, 574-586; Heiss, M. M., Int. J. Cancer 2010, 127, 2209-2221; Topp, M. S., J. Clin. Oncol. 2011, 29, 2493-2498; Sebastian, M., J. Immunother. 32, 195-202, 2009).

The potential to bind two or more targets simultaneously is an attractive concept in cancer therapy. Bispecific compounds can have multiple modes of action including: (1) simultaneous inhibition of two cell surface receptors; (2)

blocking of two ligands; (3) crosslinking of two receptors; (4) delivery of toxins or death inducing agents to kill tumor cells; and (5) T cell recruitment to the proximity of tumor cells to induce antibody-dependent cellular cytotoxicity ("redirected lysis") (Chan A. C., Nat. Rev. Immunology 10, 301-316, May 2010).

A major strategy for endowing antibodies with new activities is the development of bi-specific antibodies for redirecting T cells to kill tumor cells. The most successful format identified to date is known as a "BiTE" (bi-specific T cell engager). Blinatumomab (MT 103; Micromet/Medimmune), a BiTE specific for CD19 and CD3, has been used to treat patients with non-Hodgkin's lymphoma.

To date, all BiTEs and other bi-specific antibodies engage T cells through use of a conserved component of the TCR, such as CD3. Targeting T cells non-specifically through conserved complexes such as CD3 may result in undesired effects which can compromise efficacy or possibly lead to undesired side-effects. Because most T cells are not effector T cells, non-specific targeting is likely to recruit irrelevant T cells to the site of interest compromising efficacy. In addition to recruiting irrelevant T cells, non-specific targeting may even recruit regulatory and suppressor T cells which inhibit the effector T cell populations and therefore limit effective anti-tumor T cell responses. Thus, there is a need for more effective and reproducible therapies with fewer side effects.

Anti-clonotypic antibodies, MHC molecules (e.g., MHC class I monomers or multimers, MHC class I-immunoglobulin complexes, MHC class II monomers or multimers, MHC class II-immunoglobulin complexes) can be used to selectively recruit antigen-specific T cell populations. The present disclosure describes using such moieties to selectively recruit antigen-specific T cells and re-direct them to kill desired target cells, by coordinating these functions using a nanoparticle, and we term this approach Antigen-specific T cell Redirector (ATR). Model systems demonstrating this approach are described in the specific examples, below. These examples include using either an MHC-Ig dimer or an anti-clonotypic anti-TCR-specific mAb (1B2) bound to a nanoparticle which also comprises an anti-human CD19 antibody to target specific effector T cell populations. These nanoparticle complexes (ATR, described below) are able to redirect antigen-specific cytotoxic T cells to kill cancer cells including human B cell lymphomas. This approach permits selective engagement of specific effector T cell populations and, by using nanoparticles, overcomes the limitations associated with previous approaches. In addition, ATRs can be used in conjugation with virus specific immunization to specifically increase the targeted antigen-specific effector populations, and the reductionist ATR system allows for easy exchange of both surface molecules to either engage a different effector T cell population and/or a different target cell type.

Antigen-Specific T Cell Redirectors

"Antigen-specific T cell Redirectors" (ATRs; also referred to herein as "redirection beads") are nanoparticles comprising (A) at least one antibody that specifically binds to an antigen or epitope thereof present on a desired target cell and (B) at least one moiety that specifically binds antigen-specific effector T cells. ATR redirect the specific effector T cell population to the target cells, where the effector T cells mediate lysis of the target cells. As demonstrated below in the specific examples, ATRs show exquisite antigen-specific functionality in in vitro experiments. This is even more striking taking into account that these constructs have a size of 50-100 nm, a size which has been considered too big to generate sufficient cell-cell contact for re-directional killing (James J R, Nature. 2012 Jul. 5; 487(7405):64-9). Components of ATRs are described below. Advantageously, whereas bispecific antibodies of necessity have a 1:1 ratio of their two binding moieties, components (A) and (B) of ATRs need not be present on the nanoparticle in a 1:1 ratio. In addition, as described below, multiple combinations of components (A) and (B) are possible. Both of these features permit great flexibility in designing ATRs to meet a particular need.

An ATR also can include other molecules that have a biological effect on a precursor T cell or on an antigen-specific T cell ("T cell affecting molecules"). Such biological effects include, for example, differentiation of a precursor T cell into a CTL, helper T cell (e.g., Th1, Th2), or regulatory T cell; proliferation of T cells; and induction of T cell apoptosis. Thus, T cell affecting molecules include T cell costimulatory molecules, adhesion molecules. T cell growth factors, regulatory T cell inducer molecules, and apoptosis-inducing molecules. In some embodiments, an ATR comprises at least one such molecule; optionally, an ATR comprises at least two, three, or four such molecules, in any combination.

T cell costimulatory molecules contribute to the activation of antigen-specific T cells. Such molecules include, but are not limited to, molecules that specifically bind to CD28 (including antibodies), CD80 (B7-1), CD86 (B7-2), B7-H3, 4-1BBL, CD27, CD30, CD134 (OX-40L), B7h (B7RP-1), CD40, LIGHT, antibodies that specifically bind to HVEM, antibodies that specifically bind to CD40L, antibodies that specifically bind to OX40, and antibodies that specifically bind to 4-1BB.

Adhesion molecules useful for ATRs can be used to mediate adhesion of the ATR to a T cell or to a T cell precursor. Useful adhesion molecules include, for example, ICAM-1 and LFA-3.

T cell growth factors affect proliferation and/or differentiation of T cells. Examples of T cell growth factors include cytokines (e.g., interleukins, interferons) and superantigens. If desired, cytokines can be present in molecular complexes comprising fusion proteins. In one embodiment, a cytokine molecular complex can comprise at least two fusion proteins: a first fusion protein comprises a first cytokine and an immunoglobulin heavy chain and a second fusion protein comprises a second cytokine and a second immunoglobulin heavy chain. The first and second immunoglobulin heavy chains associate to form the cytokine molecular complex. In another embodiment, a cytokine molecular complex comprises at least four fusion proteins: two first fusion proteins comprise (i) an immunoglobulin heavy chain and (ii) a first cytokine and two second fusion proteins comprise (i) an immunoglobulin light chain and (ii) a second cytokine. The two first and the two second fusion proteins associate to form the cytokine molecular complex. The first and second cytokines in either type of cytokine molecular complex can be the same or different. Particularly useful cytokines include IL-2, IL-4, IL-7, IL-10, IL-12, IL-15, and gamma interferon.

Superantigens are powerful T cell mitogens. Superantigens stimulate T cell mitogenesis by first binding to class II major histocompatibility (MHC) molecules and then as a binary complex bind in a Vβ-specific manner to the T cell antigen receptor (TCR). Superantigens include, but are not limited to, bacterial enterotoxins, such as staphylococcal enterotoxins (e.g., SEA and active portions thereof, disclosed in U.S. Pat. No. 5,859,207; SEB, SEC, SED and SEE retroviral superantigens (disclosed in U.S. Pat. No. 5,519, 114); *Streptococcus pyogenes* exotoxin (SPE), *Staphyloccoc-* cus aureus toxic shock-syndrome toxin (TSST-1), a streptococcal mitogenic exotoxin (SME) and a streptococcal superantigen (SSA) (disclosed in US 2003/0039655); and superantigens disclosed in US 2003/0036644 and US 2003/0009015.

Regulatory T cell inducer molecules are molecules that induce differentiation and/or maintenance of regulatory T cells. Such molecules include, but are not limited to, TGFβ, IL-10, interferon-α, and IL-15. See, e.g., US 2003/0049696, US 2002/0090724, US 2002/0090357, US 2002/0034500, and US 2003/0064067.

Apoptosis-inducing molecules cause cell death. Apoptosis-inducing molecules include toxins (e.g., ricin A chain, mutant *Pseudomonas* exotoxins, diphtheria toxoid, streptonigrin, boamycin, saporin, gelonin, and pokeweed antiviral protein), TNFα, and Fas ligand.

Nanoparticles

Nanoparticles used in ATRs can be made of metals such as iron, nickel, aluminum, copper, zinc, cadmium, titanium, zirconium, tin, lead, chromium, manganese and cobalt; metal oxides and hydrated oxides such as aluminum oxide, chromium oxide, iron oxide, zinc oxide, and cobalt oxide; metal silicates such as of magnesium, aluminum, zinc, lead, chromium, copper, iron, cobalt, and nickel; alloys such as bronze, brass, stainless steel, and so forth. Nanoparticles can also be made of non-metal or organic materials such as cellulose, ceramics, glass, nylon, polystyrene, rubber, plastic, or latex. In some embodiments, nanoparticles are formed from a combination of a metal and a non-metal or organic compound, for example, methacrylate- or styrene-coated metals and silicate-coated metals. The base material can be doped with an agent to alter its physical or chemical properties. For example, rare earth oxides can be included in aluminosilicate glasses to create a paramagnetic glass materials with high density (see White & Day, Key Engineering Materials Vol. 94-95, 181-208, 1994). Alternatively, nanoparticles can be made entirely of biodegradable organic materials, such as cellulose, dextran, and the like.

Suitable commercially available nanoparticles include, for example, nickel nanoparticles (Type 123, VM 63, 18/209A, 10/585A, 347355 and HDNP sold by Novamet Specialty Products, Inc., Wyckoff, N.J.; 08841R sold by Spex, Inc.; 01509BW sold by Aldrich), stainless steel nanoparticles (P316L sold by Ametek), zinc dust (Aldrich), palladium nanoparticles (D13A17, John Matthey Elec.), M-450 Epoxy Beads (Dynal), $TiO_2$, $SiO_2$, and $MnO_2$ nanoparticles (Aldrich); and IgG-coated beads available from Miltenyi Biotec.

The configuration of nanoparticles can vary from being irregular in shape to being spherical and/or from having an uneven or irregular surface to having a smooth surface. Preferred characteristics of nanoparticles can be selected depending on the particular conditions under which an ATR will be prepared and/or used.

Nanoparticles may be of uniform or variable size. Particle size distribution can be conveniently determined, for example, using dynamic light scattering.

In some embodiments, nanoparticles have a mean particle diameter of 2-500 nm.

In some embodiments nm, nanoparticles have a mean particle diameter of 2-3 nm, 2-4 nm, 2-5 nm, 2-6 nm, 2-7 nm, 2-8 nm, 2-9 nm, 2-10 nm, 2-11 nm, 2-12 nm, 2-13 nm, 2-14 nm, 2-15 nm, 2-16 nm, 2-17 nm, 2-18 nm, 2-19 nm, 2-20 nm, 2-21 nm, 2-22 nm, 2-23 nm, 2-24 nm, 2-25 nm, 2-26 nm, 2-27 nm, 2-28 nm, 2-29 nm, 2-30 nm, 3-4 nm, 3-5 nm, 3-6 nm, 3-7 nm, 3-8 nm, 3-9 nm, 3-10 nm, 3-11 nm, 3-12 nm, 3-13 nm, 3-14 nm, 3-15 nm, 3-16 nm, 3-17 nm, 3-18 nm, 3-19 nm, 3-20 nm, 3-21 nm, 3-22 nm, 3-23 nm, 3-24 nm, 3-25 nm, 3-26 nm, 3-27 nm, 3-28 nm, 3-29 nm, 3-30 nm, 4-5 nm, 4-6 nm, 4-7 nm, 4-8 nm, 4-9 nm, 4-10 nm, 4-11 nm, 4-12 nm, 4-13 nm, 4-14 nm, 4-15 nm, 4-16 nm, 4-17 nm, 4-18 nm, 4-19 nm, 4-20 nm, 4-21 nm, 4-22 nm, 4-23 nm, 4-24 nm, 4-25 nm, 4-26 nm, 4-27 nm, 4-28 nm, 4-29 nm, 4-30 nm, 5-6 nm, 5-7 nm, 5-8 nm, 5-9 nm, 5-10 nm, 5-11 nm, 5-12 nm, 5-13 nm, 5-14 nm, 5-15 nm, 5-16 nm, 5-17 nm, 5-18 nm, 5-19 nm, 5-20 nm, 5-21 nm, 5-22 nm, 5-23 nm, 5-24 nm, 5-25 nm, 5-26 nm, 5-27 nm, 5-28 nm, 5-29 nm, 5-30 nm, 6-7 nm, 6-8 nm, 6-9 nm, 6-10 nm, 6-11 nm, 6-12 nm, 6-13 nm, 6-14 nm, 6-15 nm, 6-16 nm, 6-17 nm, 6-18 nm, 6-19 nm, 6-20 nm, 6-21 nm, 6-22 nm, 6-23 nm, 6-24 nm, 6-25 nm, 6-26 nm, 6-27 nm, 6-28 nm, 6-29 nm, 6-30 nm, 7-8 nm, 7-9 nm, 7-10 nm, 7-11 nm, 7-12 nm, 7-13 nm, 7-14 nm, 7-15 nm, 7-16 nm, 7-17 nm, 7-18 nm, 7-19 nm, 7-20 nm, 7-21 nm, 7-22 nm, 7-23 nm, 7-24 nm, 7-25 nm, 7-26 nm, 7-27 nm, 7-28 nm, 7-29 nm, 7-30 nm, 8-9 nm, 8-10 nm, 8-11 nm, 8-12 nm, 8-13 nm, 8-14 nm, 8-15 nm, 8-16 nm, 8-17 nm, 8-18 nm, 8-19 nm, 8-20 nm, 8-21 nm, 8-22 nm, 8-23 nm, 8-24 nm, 8-25 nm, 8-26 nm, 8-27 nm, 8-28 nm, 8-29 nm, 8-30 nm, 9-10 nm, 9-11 nm, 9-12 nm, 9-13 nm, 9-14 nm, 9-15 nm, 9-16 nm, 9-17 nm, 9-18 nm, 9-19 nm, 9-20 nm, 9-21 nm, 9-22 nm, 9-23 nm, 9-24 nm, 9-25 nm, 9-26 nm, 9-27 nm, 9-28 nm, 9-29 nm, 9-30 nm, 10-11 nm, 10-12 nm, 10-13 nm, 10-14 nm, 10-15 nm, 10-16 nm, 10-17 nm, 10-18 nm, 10-19 nm, 10-20 nm, 10-21 nm, 10-22 nm, 10-23 nm, 10-24 nm, 10-25 nm, 10-26 nm, 10-27 nm, 10-28 nm, 10-29 nm, 10-30 nm, 11-12 nm, 11-13 nm, 11-14 nm, 11-15 nm, 11-16 nm, 11-17 nm, 11-18 nm, 11-19 nm, 11-20 nm, 11-21 nm, 11-22 nm, 11-23 nm, 11-24 nm, 11-25 nm, 11-26 nm, 11-27 nm, 11-28 nm, 11-29 nm, 11-30 nm, 12-13 nm, 12-14 nm, 12-15 nm, 12-16 nm, 12-17 nm, 12-18 nm, 12-19 nm, 12-20 nm, 12-21 nm, 12-22 nm, 12-23 nm, 12-24 nm, 12-25 nm, 12-26 nm, 12-27 nm, 12-28 nm, 12-29 nm, 12-30 nm, 13-14 nm, 13-15 nm, 13-16 nm, 13-17 nm, 13-18 nm, 13-19 nm, 13-20 nm, 13-21 nm, 13-22 nm, 13-23 nm, 13-24 nm, 13-25 nm, 13-26 nm, 13-27 nm, 13-28 nm, 13-29 nm, 13-30 nm, 14-15 nm, 14-16 nm, 14-17 nm, 14-18 nm, 14-19 nm, 14-20 nm, 14-21 nm, 14-22 nm, 14-23 nm, 14-24 nm, 14-25 nm, 14-26 nm, 14-27 nm, 14-28 nm, 14-29 nm, 14-30 nm, 15-16 nm, 15-17 nm, 15-18 nm, 15-19 nm, 15-20 nm, 15-21 nm, 15-22 nm, 15-23 nm, 15-24 nm, 15-25 nm, 15-26 nm, 15-27 nm, 15-28 nm, 15-29 nm, 15-30 nm, 16-17 nm, 16-18 nm, 16-19 nm, 16-20 nm, 16-21 nm, 16-22 nm, 16-23 nm, 16-24 nm, 16-25 nm, 16-26 nm, 16-27 nm, 16-28 nm, 16-29 nm, 16-30 nm, 17-18 nm, 17-19 nm, 17-20 nm, 17-21 nm, 17-22 nm, 17-23 nm, 17-24 nm, 17-25 nm, 17-26 nm, 17-27 nm, 17-28 nm, 17-29 nm, 17-30 nm, 18-19 nm, 18-20 nm, 18-21 nm, 18-22 nm, 18-23 nm, 18-24 nm, 18-25 nm, 18-26 nm, 18-27 nm, 18-28 nm, 18-29 nm, 18-30 nm, 19-20 nm, 19-21 nm, 19-22 nm, 19-23 nm, 19-24 nm, 19-25 nm, 19-26 nm, 19-27 nm, 19-28 nm, 19-29 nm, 19-30 nm, 20-21 nm, 20-22 nm, 20-23 nm, 20-24 nm, 20-25 nm, 20-26 nm, 20-27 nm, 20-28 nm, 20-29 nm, 20-30 nm, 21-21 nm, 21-22 nm, 21-23 nm, 21-24 nm, 21-25 nm, 21-26 nm, 21-27 nm, 21-28 nm, 21-29 nm, 21-30 nm, 22-23 nm, 22-24 nm, 22-25 nm, 22-26 nm, 22-27 nm, 22-28 nm, 22-29 nm, 22-30 nm, 23-24 nm, 23-25 nm, 23-26 nm, 23-27 nm, 23-28 nm, 23-29 nm, 23-30 nm, 24-25 nm, 24-26 nm, 24-27 nm, 24-28 nm, 24-29 nm, 24-30 nm, 25-26 nm, 25-27 nm, 25-28 nm, 25-29 nm, 25-30 nm, 26-27 nm, 26-28 nm, 26-29 nm, 26-30 nm, 27-28 nm, 27-29 nm, 27-30 nm, 28-29 nm, 28-30 nm, or 29-30 nm.

In some embodiments, nanoparticles have a mean particle diameter of 25-500 nm+/−5 nm, 25-500 nm+/−10 nm, 25-500 nm+/−15 nm, 25-500 nm+/−20 nm, 25-500 nm+/−25 nm, 25-500 nm+/−30 nm, 25-500 nm+/−35 nm, 25-500 nm+/−40 nm, 25-500 nm+/−45 nm, or 25-500 nm+/−50 nm.

In some embodiments, nanoparticles have a mean particle diameter of 25-30 nm, 25-35 nm, 25-40 nm, 25-45 nm, 25-50 nm, 25-55 nm, 25-60 nm, 25-70 nm, 25-75 nm, 25-80 nm, 25-90 nm, 25-95 nm, 25-100 nm, 25-125 nm, 25-150 nm, 25-200 nm, 25-300 nm, 25-400 nm, 30-35 nm, 35-40 nm, 35-45 nm, 35-50 nm, 35-55 nm, 35-60 nm, 35-70 nm, 35-75 nm, 35-80 nm, 35-90 nm, 35-95 nm, 35-100 nm, 35-125 nm, 35-150 nm, 35-200 nm, 35-300 nm, 35-400, 35-500 nm, 40-45 nm, 35-50 nm, 45-55 nm, 45-60 nm, 45-70 nm, 45-75 nm, 45-80 nm, 45-90 nm, 45-95 nm, 45-100 nm, 45-125 nm, 45-150 nm, 45-200 nm, 45-300 nm, 45-400, 45-500 nm, 50-55 nm, 50-60 nm, 50-70 nm, 50-75 nm, 50-80 nm, 50-90 nm, 50-95 nm, 50-100 nm, 50-125 nm, 50-150 nm, 50-200 nm, 50-300 nm, 50-400 nm, 50-500 nm, 55-60 nm, 55-70 nm, 55-75 nm, 55-80 nm, 55-90 nm, 55-95 nm, 55-100 nm, 55-125 nm, 55-150 nm, 55-200 nm, 55-300 nm, 55-400 nm, 55-500 nm, 60-70 nm, 60-75 nm, 60-80 nm, 60-90 nm, 60-95 nm, 60-100 nm, 60-125 nm, 60-150 nm, 60-200 nm, 60-300 nm, 60-400 nm, 60-500 nm, 65-70 nm, 65-75 nm, 65-80 nm, 65-90 nm, 65-95 nm, 65-100 nm, 65-125 nm, 65-150 nm, 65-200 nm, 65-300 nm, 65-400, 65-500 nm, 70-75 nm, 70-80 nm, 70-90 nm, 70-95 nm, 70-100 nm, 70-125 nm, 70-150 nm, 70-200 nm, 70-300 nm, 70-400, 70-500 nm, 75-80 nm, 75-90 nm, 75-95 nm, 75-100 nm, 75-125 nm, 75-150 nm, 75-200 nm, 75-300 nm, 75-400, 75-500 nm, 80-90 nm, 80-95 nm, 80-100 nm, 80-125 nm, 80-150 nm, 80-200 nm, 80-300 nm, 80-400 nm, 80-500 nm, 85-90 nm, 85-95 nm, 85-100 nm, 85-125 nm, 85-150 nm, 85-200 nm, 85-300 nm, 85-400, 85-500 nm, 90-95 nm, 90-100 nm, 90-125 nm, 90-150 nm, 90-200 nm, 90-300 nm, 90-400, 90-500 nm, 100-125 nm, 100-150 nm, 100-200 nm, 100-300 nm, 100-400, 100-500 nm, 125-150 nm, 125-200 nm, 125-300 nm, 125-400, 125-500 nm, 150-200 nm, 150-300 nm, 150-400, 150-500 nm, 175-200 nm, 175-300 nm, 175-400, 175-500 nm, 200-300 nm, 200-400, 200-500 nm, 300-400, 300-500 nm, or 400-500 nm.

In some embodiments, nanoparticles have a mean particle diameter of 25-30 nm+/−5 nm, 25-35 nm+/−5 nm, 25-40 nm+/−5 nm, 25-45 nm+/−5 nm, 25-50 nm+/−5 nm, 25-55 nm+/−5 nm, 25-60 nm+/−5 nm, 25-70 nm+/−5 nm, 25-75 nm+/−5 nm, 25-80 nm+/−5 nm, 25-90 nm+/−5 nm, 25-95 nm+/−5 nm, 25-100 nm+/−5 nm, 25-125 nm+/−5 nm, 25-150 nm+/−5 nm, 25-200 nm+/−5 nm, 25-300 nm+/−5 nm, 25-400 nm+/−5 nm, 30-35 nm+/−5 nm, 35-40 nm+/−5 nm, 35-45 nm+/−5 nm, 35-50 nm+/−5 nm, 35-55 nm+/−5 nm, 35-60 nm+/−5 nm, 35-70 nm+/−5 nm, 35-75 nm+/−5 nm, 35-80 nm+/−5 nm, 35-90 nm+/−5 nm, 35-95 nm+/−5 nm, 35-100 nm+/−5 nm, 35-125 nm+/−5 nm, 35-150 nm+/−5 nm, 35-200 nm+/−5 nm, 35-300 nm+/−5 nm, 35-400, 35-500 nm+/−5 nm, 40-45 nm+/−5 nm, 35-50 nm+/−5 nm, 45-55 nm+/−5 nm, 45-60 nm+/−5 nm, 45-70 nm+/−5 nm, 45-75 nm+/−5 nm, 45-80 nm+/−5 nm, 45-90 nm+/−5 nm, 45-95 nm+/−5 nm, 45-100 nm+/−5 nm, 45-125 nm+/−5 nm, 45-150 nm+/−5 nm, 45-200 nm+/−5 nm, 45-300 nm+/−5 nm, 45-400, 45-500 nm+/−5 nm, 50-55 nm+/−5 nm, 50-60 nm+/−5 nm, 50-70 nm+/−5 nm, 50-75 nm+/−5 nm, 50-80 nm+/−5 nm, 50-90 nm+/−5 nm, 50-95 nm+/−5 nm, 50-100 nm+/−5 nm, 50-125 nm+/−5 nm, 50-150 nm+/−5 nm, 50-200 nm+/−5 nm, 50-300 nm+/−5 nm, 50-400, 50-500 nm+/−5 nm, 55-60 nm+/−5 nm, 55-70 nm+/−5 nm, 55-75 nm+/−5 nm, 55-80 nm+/−5 nm, 55-90 nm+/−5 nm, 55-95 nm+/−5 nm, 55-100 nm+/−5 nm, 55-125 nm+/−5 nm, 55-150 nm+/−5 nm, 55-200 nm+/−5 nm, 55-300 nm+/−5 nm, 55-400, 55-500 nm+/−5 nm, 60-70 nm+/−5 nm, 60-75 nm+/−5 nm, 60-80 nm+/−5 nm, 60-90 nm+/−5 nm, 60-95 nm+/−5 nm, 60-100 nm+/−5 nm, 60-125 nm+/−5 nm, 60-150 nm+/−5 nm, 60-200 nm+/−5 nm, 60-300 nm+/−5 nm, 60-400, 60-500 nm+/−5 nm, 65-70 nm+/−5 nm, 65-75 nm+/−5 nm, 65-80 nm+/−5 nm, 65-90 nm+/−5 nm, 65-95 nm+/−5 nm, 65-100 nm+/−5 nm, 65-125 nm+/−5 nm, 65-150 nm+/−5 nm, 65-200 nm+/−5 nm, 65-300 nm+/−5 nm, 65-400, 65-500 nm+/−5 nm, 70-75 nm+/−5 nm, 70-80 nm+/−5 nm, 70-90 nm+/−5 nm, 70-95 nm+/−5 nm, 70-100 nm+/−5 nm, 70-125 nm+/−5 nm, 70-150 nm+/−5 nm, 70-200 nm+/−5 nm, 70-300 nm+/−5 nm, 70-400, 70-500 nm+/−5 nm, 75-80 nm+/−5 nm, 75-90 nm+/−5 nm, 75-95 nm+/−5 nm, 75-100 nm+/−5 nm, 75-125 nm+/−5 nm, 75-150 nm+/−5 nm, 75-200 nm+/−5 nm, 75-300 nm+/−5 nm, 75-400, 75-500 nm+/−5 nm, 80-90 nm+/−5 nm, 80-95 nm+/−5 nm, 80-100 nm+/−5 nm, 80-125 nm+/−5 nm, 80-150 nm+/−5 nm, 80-200 nm+/−5 nm, 80-300 nm+/−5 nm, 80-400, 80-500 nm+/−5 nm, 85-90 nm+/−5 nm, 85-95 nm+/−5 nm, 85-100 nm+/−5 nm, 85-125 nm+/−5 nm, 85-150 nm+/−5 nm, 85-200 nm+/−5 nm, 85-300 nm+/−5 nm, 85-400, 85-500 nm+/−5 nm, 90-95 nm+/−5 nm, 90-100 nm+/−5 nm, 90-125 nm+/−5 nm, 90-150 nm+/−5 nm, 90-200 nm+/−5 nm, 90-300 nm+/−5 nm, 90-400, 90-500 nm+/−5 nm, 100-125 nm+/−5 nm, 100-150 nm+/−5 nm, 100-200 nm+/−5 nm, 100-300 nm+/−5 nm, 100-400, 100-500 nm+/−5 nm, 125-150 nm+/−5 nm, 125-200 nm+/−5 nm, 125-300 nm+/−5 nm, 125-400, 125-500 nm+/−5 nm, 150-200 nm+/−5 nm, 150-300 nm+/−5 nm, 150-400, 150-500 nm+/−5 nm, 175-200 nm+/−5 nm, 175-300 nm+/−5 nm, 175-400, 175-500 nm+/−5 nm, 200-300 nm+/−5 nm, 200-400, 200-500 nm+/−5 nm, 300-400, 300-500 nm+/−5 nm, or 400-500 nm+/−5 nm.

In some embodiments, nanoparticles have a mean particle diameter of 25-30 nm+/−10 nm, 25-35 nm+/−10 nm, 25-40 nm+/−10 nm, 25-45 nm+/−10 nm, 25-100 nm+/−10 nm, 25-105 nm+/−10 nm, 25-60 nm+/−10 nm, 25-70 nm+/−10 nm, 25-75 nm+/−10 nm, 25-80 nm+/−10 nm, 25-90 nm+/−10 nm, 25-95 nm+/−10 nm, 25-100 nm+/−10 nm, 25-125 nm+/−10 nm, 25-150 nm+/−10 nm, 25-200 nm+/−10 nm, 25-300 nm+/−10 nm, 25-400 nm+/−10 nm, 30-35 nm+/−10 nm, 35-40 nm+/−10 nm, 35-45 nm+/−10 nm, 35-100 nm+/−10 nm, 35-105 nm+/−10 nm, 35-60 nm+/−10 nm, 35-70 nm+/−10 nm, 35-75 nm+/−10 nm, 35-80 nm+/−10 nm, 35-90 nm+/−10 nm, 35-95 nm+/−10 nm, 35-100 nm+/−10 nm, 35-125 nm+/−10 nm, 35-150 nm+/−10 nm, 35-200 nm+/−10 nm, 35-300 nm+/−10 nm, 35-400, 35-1000 nm+/−10 nm, 40-45 nm+/−10 nm, 35-100 nm+/−10 nm, 45-105 nm+/−10 nm, 45-60 nm+/−10 nm, 45-70 nm+/−10 nm., 45-75 nm+/−10 nm, 45-80 nm+/−10 nm, 45-90 nm+/−10 nm, 45-95 nm+/−10 nm, 45-100 nm+/−10 nm, 45-125 nm+/−10 nm, 45-150 nm+/−10 nm, 45-200 nm+/−10 nm, 45-300 nm+/−10 nm, 45-400, 45-1000 nm+/−10 nm, 50-105 nm+/−10 nm, 50-60 nm+/−10 nm, 50-70 nm+/−10 nm, 50-75 nm+/−10 nm, 50-80 nm+/−10 nm, 50-90 nm+/−10 nm, 50-95 nm+/−10 nm, 50-100 nm+/−10 nm, 50-125 nm+/−10 nm, 50-150 nm+/−10 nm, 50-200 nm+/−10 nm, 50-300 nm+/−10 nm, 50-400, 50-1000 nm+/−10 nm, 55-60 nm+/−10 nm, 55-70 nm+/−10 nm, 55-75 nm+/−10 nm, 55-80 nm+/−10 nm, 55-90 nm+/−10 nm, 55-95 nm+/−10 nm, 55-100 nm+/−10 nm, 55-125 nm+/−10 nm, 55-150 nm+/−10 nm, 55-200 nm+/−10 nm, 55-300 nm+/−10 nm, 55-400, 55-1000 nm+/−10 nm, 60-70 nm+/−10 nm, 60-75 nm+/−10 nm, 60-80 nm+/−10 nm, 60-90 nm+/−10 nm, 60-95 nm+/−10 nm, 60-100 nm+/−10 nm, 60-125 nm+/−10 nm, 60-150 nm+/−10 nm, 60-200 nm+/−10 nm, 60-300 nm+/−10 nm, 60-400, 60-1000 nm+/−10 nm, 65-70 nm+/−10 nm, 65-75 nm+/−10 nm, 65-80 nm+/−10 nm, 65-90 nm+/−10 nm, 65-95 nm+/−10 nm, 65-100 nm+/−10 n, 65-125 nm+/−10 nm, 65-150 nm+/−10 nm, 65-200 nm+/−10 nm, 65-300 nm+/−10 nm, 65-400, 65-1000 nm+/−10 nm, 70-75 nm+/−10 nm, 70-80 nm+/−10 nm, 70-90 nm+/−10 nm, 70-95 nm+/−10 nm, 70-100 nm+/−10 nm, 70-125 nm+/−10 nm, 70-150 nm+/−10 nm, 70-200 nm+/−10 nm, 70-300 nm+/−10 nm, 70-400, 70-1000 nm+/−10 nm, 75-80 nm+/−10 nm, 75-90 nm+/−10 nm, 75-95 nm+/−10 nm, 75-100 nm+/−10 nm, 75-125 nm+/−10 nm, 75-150 nm+/−10 nm, 75-200 nm+/−10 nm, 75-300 nm+/−10 nm, 75-400, 75-1000 nm+/−10 nm, 80-90 nm+/−10 nm, 80-95 nm+/−10 nm, 80-100 nm+/−10 nm, 80-125 nm+/−10 nm, 80-150 nm+/−10 nm, 80-200 nm+/−10 nm, 80-300 nm+/−10 nm, 80-400, 80-1000 nm+/−10 nm, 85-90 nm+/−10 nm, 85-95 nm+/−10 nm, 85-100 nm+/−10 nm, 85-125 nm+/−10 nm, 85-150 nm+/−10 nm, 85-200 nm+/−10 nm, 85-300 nm+/−10 nm, 85-400, 85-1000 nm+/−10 nm, 90-95 nm+/−10 nm, 90-100 nm+/−10 nm, 90-125 nm+/−10 nm, 90-150 nm+/−10 nm, 90-200 nm+/−10 nm, 90-300 nm+/−10 nm, 90-400, 90-1000 nm+/−10 nm, 100-125 nm+/−10 nm, 100-150 nm+/−10 nm, 100-200 nm+/−10 nm, 100-300 nm+/−10 nm, 100-400, 100-1000 nm+/−10 nm, 125-150 nm+/−10 nm, 125-200 nm+/−10 nm, 125-300 nm+/−10 nm, 125-400, 125-1000 nm+/−10 nm, 150-200 nm+/−10 nm, 150-300 nm+/−10 nm. 150-400, 150-1000 nm+/−10 nm, 175-200 nm+/−10 nm, 175-300 nm+/−10 nm, 175-400, 175-1000 nm+/−10 nm, 200-300 nm+/−10 nm, 200-400, 200-1000 nm+/−10 nm, 300-400, 300-1000 nm+/−10 nm, or 400-1000 nm+/−10 nm.

In some embodiments, nanoparticles have a mean particle diameter of 25-30 nm+/−15 nm, 25-35 nm+/−15 nm, 25-40 nm+/−15 nm, 25-45 nm+/−15 nm, 25-150 nm+/−15 nm, 25-155 nm+/−15 nm, 25-60 nm+/−15 nm, 25-70 nm+/−15 nm, 25-75 nm+/−15 nm, 25-80 nm+/−15 nm, 25-90 nm+/−15 nm, 25-95 nm+/−15 nm, 25-100 nm+/−15 nm, 25-125 nm+/−15 nm, 25-150 nm+/−15 nm, 25-200 nm+/−15 nm, 25-300 nm+/−15 nm, 25-400 nm+/−15 nm, 30-35 nm+/−15 nm, 35-40 nm+/−15 nm, 35-45 nm+/−15 nm, 35-150 nm+/−15 nm, 35-155 nm+/−15 nm, 35-60 nm+/−15 nm, 35-70 nm+/−15 nm, 35-75 nm+/−15 nm, 35-80 nm+/−15 nm, 35-90 nm+/−15 nm, 35-95 nm+/−15 nm, 35-100 nm+/−15 nm, 35-125 nm+/−15 nm, 35-150 nm+/−15 nm, 35-200 nm+/−15 nm, 35-300 nm+/−15 nm, 35-400, 35-1500 nm+/−15 nm, 40-45 nm+/−15 nm, 35-150 nm+/−15 nm, 45-155 nm+/−15 nm, 45-60 nm+/−15 nm, 45-70 nm+/−15 nm, 45-75 nm+/−15 nm, 45-80 nm+/−15 nm, 45-90 nm+/−15 nm, 45-95 nm+/−15 nm, 45-100 nm+/−15 nm, 45-125 nm+/−15 nm, 45-150 nm+/−15 nm, 45-200 nm+/−15 nm, 45-300 nm+/−15 nm, 45-400, 45-1500 nm+/−15 nm, 50-155 nm+/−15 nm, 50-60 nm+/−15 nm, 50-70 nm+/−15 nm, 50-75 nm+/−15 nm, 50-80 nm+/−15 nm, 50-90 nm+/−15 nm, 50-95 nm+/−15 nm, 50-100 nm+/−15 nm, 50-125 nm+/−15 nm, 50-150 nm+/−15 nm, 50-200 nm+/−15 nm, 50-300 nm+/−15 nm, 50-400, 50-1500 nm+/−15 nm, 55-60 nm+/−15 nm, 55-70 nm+/−15 nm, 55-75 nm+/−15 nm, 55-80 nm+/−15 nm, 55-90 nm+/−15 nm, 55-95 nm+/−15 nm, 55-100 nm+/−15 nm, 55-125 nm+/−15 nm, 55-150 nm+/−15 nm, 55-200 nm+/−15 nm, 55-300 nm+/−15 nm, 55-400, 55-1500 nm+/−15 nm, 60-70 nm+/−15 nm, 60-75 nm+/−15 nm, 60-80 nm+/−15 nm, 60-90 nm+/−15 nm, 60-95 nm+/−15 nm, 60-100 nm+/−15 nm, 60-125 nm+/−15 nm, 60-150 nm+/−15 nm, 60-200 nm+/−15 nm, 60-300 nm+/−15 nm, 60-400, 60-1500 nm+/−15 nm, 65-70 nm+/−15 nm, 65-75 nm+/−15 nm, 65-80 nm+/−15 nm, 65-90 nm+/−15 nm, 65-95 nm+/−15 nm, 65-100 nm+/−15 nm, 65-125 nm+/−15 nm, 65-150 nm+/−15 nm, 65-200 nm+/−15 nm, 65-300 nm+/−15 nm, 65-400, 65-1500 nm+/−15 nm, 70-75 nm+/−15 nm, 70-80 nm+/−15 nm, 70-90 nm+/−15 nm, 70-95 nm+/−15 nm, 70-100 nm+/−15 nm, 70-125 nm+/−15 nm, 70-150 nm+/−15 nm, 70-200 nm+/−15 nm, 70-300 nm+/−15 nm, 70-400, 70-1500 nm+/−15 nm, 75-80 nm+/−15 nm, 75-90 nm+/−15 nm, 75-95 nm+/−15 nm, 75-100 nm+/−15 nm, 75-125 nm+/−15 nm, 75-150 nm+/−15 nm, 75-200 nm+/−15 nm, 75-300 nm+/−15 nm, 75-400, 75-1500 nm+/−15 nm, 80-90 nm+/−15 nm, 80-95 nm+/−15 nm, 80-100 nm+/−15 nm, 80-125 nm+/−15 nm, 80-150 nm+/−15 nm, 80-200 nm+/−15 nm, 80-300 nm+/−15 nm, 80-400, 80-1500 nm+/−15 nm, 85-90 nm+/−15 nm, 85-95 nm+/−15 nm, 85-100 nm+/−15 nm, 85-125 nm+/−15 nm, 85-150 nm+/−15 nm, 85-200 nm+/−15 nm, 85-300 nm+/−15 nm, 85-400, 85-1500 nm+/−15 nm, 90-95 nm+/−15 nm, 90-100 nm+/−15 nm, 90-125 nm+/−15 nm, 90-150 nm+/−15 nm, 90-200 nm+/−15 nm, 90-300 nm+/−15 nm, 90-400, 90-1500 nm+/−15 nm, 100-125 nm+/−15 nm, 100-150 nm+/−15 nm, 100-200 nm+/−15 nm, 100-300 nm+/−15 nm, 100-400, 100-1500 nm+/−15 nm, 125-150 nm+/−15 nm, 125-200 nm+/−15 nm, 125-300 nm+/−15 nm, 125-400, 125-1500 nm+/−15 nm, 150-200 nm+/−15 nm, 150-300 nm+/−15 nm, 150-400, 150-1500 nm+/−15 nm, 175-200 nm+/−15 nm, 175-300 nm+/−15 nm, 175-400, 175-1500 nm+/−15 nm, 200-300 nm+/−15 nm, 200-400, 200-1500 nm+/−15 nm, 300-400, 300-1500 nm+/−15 nm, or 400-1500 nm+/−15 nm.

In some embodiments, nanoparticles have a mean particle diameter of 25-30 nm+/−20 nm, 25-35 nm+/−20 nm, 25-40 nm+/−20 nm, 25-45 nm+/−20 nm, 25-200 nm+/−20 nm, 25-205 nm+/−20 nm, 25-60 nm+/−20 nm, 25-70 nm+/−20 nm, 25-75 nm+/−20 nm, 25-80 nm+/−20 nm, 25-90 nm+/−20 nm, 25-95 nm+/−20 nm, 25-100 nm+/−20 nm, 25-125 nm+/−20 nm, 25-150 nm+/−20 nm, 25-200 nm+/−20 nm, 25-300 nm+/−20 nm, 25-400 nm+/−20 nm, 30-35 nm+/−20 nm, 35-40 nm+/−20 nm, 35-45 nm+/−20 nm, 35-200 nm+/−20 nm, 35-205 nm+/−20 nm, 35-60 nm+/−20 nm, 35-70 nm+/−20 nm, 35-75 nm+/−20 nm, 35-80 nm+/−20 nm, 35-90 nm+/−20 nm, 35-95 nm+/−20 nm, 35-100 nm+/−20 nm, 35-125 nm+/−20 nm, 35-150 nm+/−20 nm, 35-200 nm+/−20 nm, 35-300 nm+/−20 nm, 35-400, 35-2000 nm+/−20 nm, 40-45 nm+/−20 nm, 35-200 nm+/−20 nm, 45-205 nm+/−20 nm, 45-60 nm+/−20 nm, 45-70 nm+/−20 nm, 45-75 nm+/−20 nm, 45-80 nm+/−20 nm, 45-90 nm+/−20 nm, 45-95 nm+/−20 nm, 45-100 nm+/−20 nm, 45-125 nm+/−20 nm, 45-150 nm+/−20 nm, 45-200 nm+/−20 nm, 45-300 nm+/−20 nm, 45-400, 45-2000 nm+/−20 nm, 50-205 nm+/−20 nm, 50-60 nm+/−20 nm, 50-70 nm+/−20 nm, 50-75 nm+/−20 nm, 50-80 nm+/−20 nm, 50-90 nm+/−20 nm, 50-95 nm+/−20 nm, 50-100 nm+/−20 nm, 50-125 nm+/−20 nm, 50-150 nm+/−20 nm, 50-200 nm+/−20 nm, 50-300 nm+/−20 nm, 50-400, 50-2000 nm+/−20 nm, 55-60 nm+/−20 nm, 55-70 nm+/−20 nm, 55-75 nm+/−20 nm, 55-80 nm+/−20 nm, 55-90 nm+/−20 nm, 55-95 nm+/−20 nm, 55-100 nm+/−20 nm, 55-125 nm+/−20 nm, 55-150 nm+/−20 nm, 55-200 nm+/−20 nm, 55-300 nm+/−20 nm, 55-400, 55-2000 nm+/−20 nm, 60-70 nm+/−20 nm, 60-75 nm+/−20 nm, 60-80 nm+/−20 nm, 60-90 nm+/−20 nm, 60-95 nm+/−20 nm, 60-100 nm+/−20 nm, 60-125 nm+/−20 nm, 60-150 nm+/−20 nm, 60-200 nm+/−20 nm, 60-300 nm+/−20 nm, 60-400, 60-2000 nm+/−20 nm, 65-70 nm+/−20 nm, 65-75 nm+/−20 nm, 65-80 nm+/−20 nm, 65-90 nm+/−20 nm, 65-95 nm+/−20 nm, 65-100 nm+/−20 nm, 65-125 nm+/−20 nm, 65-150 nm+/−20 nm, 65-200 nm+/−20 nm, 65-300 nm+/−20 nm, 65-400, 65-2000 nm+/−20 nm, 70-75 nm+/−20 nm, 70-80 nm+/−20 nm, 70-90 nm+/−20 nm, 70-95 nm+/−20 nm, 70-100 nm+/−20 nm, 70-125 nm+/−20 nm, 70-150 nm+/−20 nm, 70-200 nm+/−20 nm, 70-300 nm+/−20 nm, 70-400, 70-2000 nm+/−20 nm, 75-80 nm+/−20 nm, 75-90 nm+/−20 nm, 75-95 nm+/−20 nm, 75-100 nm+/−20 nm, 75-125 nm+/−20 nm, 75-150 nm+/−20 nm, 75-200 nm+/−20 nm, 75-300 nm+/−20 nm, 75-400, 75-2000 nm+/−20 nm, 80-90 nm+/−20 nm, 80-95 nm+/−20 nm, 80-100 nm+/−20 nm, 80-125 nm+/−20 nm, 80-150 nm+/−20 nm, 80-200 nm+/−20 nm, 80-300 nm+/−20 nm, 80-400, 80-2000 nm+/−20 nm, 85-90 nm+/−20 nm, 85-95 nm+/−20 nm, 85-100 nm+/−20 nm, 85-125 nm+/−20 nm, 85-150 nm+/−20 nm, 85-200 nm+/−20 nm, 85-300 nm+/−20 nm, 85-400, 85-2000 nm+/−20 nm, 90-95 nm+/−20 nm, 90-100 nm+/−20 nm, 90-125 nm+/−20 nm, 90-150 nm+/−20 nm, 90-200 nm+/−20 nm, 90-300 nm+/−20 nm, 90-400, 90-2000 nm+/−20 nm, 100-125 nm+/−20 nm, 100-150 nm+/−20 nm, 100-200 nm+/−20 nm, 100-300 nm+/−20 nm, 100-400, 100-2000 nm+/−20 nm, 125-150 nm+/−20 nm, 125-200 nm+/−20 nm, 125-300 nm+/−20 nm, 125-400, 125-2000 nm+/−20 nm, 150-200 nm+/−20 nm, 150-300 nm+/−20 nm, 150-400, 150-2000 nm+/−20 nm, 175-200 nm+/−20 nm, 175-300 nm+/−20 nm, 175-400, 175-2000 nm+/−20 nm, 200-300 nm+/−20 nm, 200-400, 200-2000 nm+/−20 nm, 300-400, 300-2000 nm+/−20 nm, or 400-2000 nm+/−20 nm.

In some embodiments, nanoparticles have a mean particle diameter of 25-30 nm+/−25 nm, 25-35 nm+/−25 nm, 25-40 nm+/−25 nm, 25-45 nm+/−25 nm, 25-250 nm+/−25 nm, 25-255 nm+/−25 nm, 25-60 nm+/−25 nm, 25-70 nm+/−25 nm, 25-75 nm+/−25 nm, 25-80 nm+/−25 nm, 25-90 nm+/−25 nm, 25-95 nm+/−25 nm, 25-100 nm+/−25 nm, 25-125 nm+/−25 nm, 25-150 nm+/−25 nm, 25-200 nm+/−25 nm, 25-300 nm+/−25 nm, 25-400 nm+/−25 nm, 30-35 nm+/−25 nm, 35-40 nm+/−25 nm, 35-45 nm+/−25 nm, 35-250 nm+/−25 nm, 35-255 nm+/−25 nm, 35-60 nm+/−25 nm, 35-70 nm+/−25 nm, 35-75 nm+/−25 nm, 35-80 nm+/−25 nm, 35-90 nm+/−25 nm, 35-95 nm+/−25 nm, 35-100 nm+/−25 nm, 35-125 nm+/−25 nm, 35-150 nm+/−25 nm, 35-200 nm+/−25 nm, 35-300 nm+/−25 nm, 35-400, 35-2500 nm+/−25 nm, 40-45 nm+/−25 nm, 35-250 nm+/−25 nm, 45-255 nm+/−25 nm, 45-60 nm+/−25 nm, 45-70 nm+/−25 nm, 45-75 nm+/−25 nm, 45-80 nm+/−25 nm, 45-90 nm+/−25 nm, 45-95 nm+/−25 nm, 45-100 nm+/−25 nm, 45-125 nm+/−25 nm, 45-150 nm+/−25 nm, 45-200 nm+/−25 nm, 45-300 nm+/−25 nm, 45-400, 45-2500 nm+/−25 nm, 50-255 nm+/−25 nm, 50-60 nm+/−25 nm, 50-70 nm+/−25 nm, 50-75 nm+/−25 nm, 50-80 nm+/−25 nm, 50-90 nm+/−25 nm, 50-95 nm+/−25 nm, 50-100 nm+/−25 nm, 50-125 nm+/−25 nm, 50-150 nm+/−25 nm, 50-200 nm+/−25 nm, 50-300 nm+/−25 nm, 50-400, 50-2500 nm+/−25 nm, 55-60 nm+/−25 nm, 55-70 nm+/−25 nm, 55-75 nm+/−25 nm, 55-80 nm+/−25 nm, 55-90 nm+/−25 nm, 55-95 nm+/−25 nm, 55-100 nm+/−25 nm, 55-125 nm+/−25 nm, 55-150 nm+/−25 nm, 55-200 nm+/−25 nm, 55-300 nm+/−25 nm, 55-400, 55-2500 nm+/−25 nm, 60-70 nm+/−25 nm, 60-75 nm+/−25 nm, 60-80 nm+/−25 nm, 60-90 nm+/−25 nm, 60-95 nm+/−25 nm, 60-100 nm+/−25 nm, 60-125 nm+/−25 nm, 60-150 nm+/−25 nm, 60-200 nm+/−25 nm, 60-300 nm+/−25 nm, 60-400, 60-2500 nm+/−25 nm, 65-70 nm+/−25 nm, 65-75 nm+/−25 nm, 65-80 nm+/−25 nm, 65-90 nm+/−25 nm, 65-95 nm+/−25 nm, 65-100 nm+/−25 nm, 65-125 nm+/−25 nm, 65-150 nm+/−25 nm, 65-200 nm+/−25 nm, 65-300 nm+/−25 nm, 65-400, 65-2500 nm+/−25 nm, 70-75 nm+/−25 nm, 70-80 nm+/−25 nm, 70-90 nm+/−25 nm, 70-95 nm+/−25 nm, 70-100 nm+/−25 nm, 70-125 nm+/−25 nm, 70-150 nm+/−25 nm, 70-200 nm+/−25 nm, 70-300 nm+/−25 nm, 70-400, 70-2500 nm+/−25 nm, 75-80 nm+/−25 nm, 75-90 nm+/−25 nm, 75-95 nm+/−25 nm, 75-100 nm+/−25 nm, 75-125 nm+/−25 nm, 75-150 nm+/−25 nm, 75-200 nm+/−25 nm, 75-300 nm+/−25 nm, 75-400, 75-2500 nm+/−25 nm, 80-90 nm+/−25 nm, 80-95 nm+/−25 nm, 80-100 nm+/−25 nm, 80-125 nm+/−25 nm, 80-150 nm+/−25 nm, 80-200 nm+/−25 nm, 80-300 nm+/−25 nm, 80-400, 80-2500 nm+/−25 nm, 85-90 nm+/−25 nm, 85-95 nm+/−25 nm, 85-100 nm+/−25 nm, 85-125 nm+/−25 nm, 85-150 nm+/−25 nm, 85-200 nm+/−25 nm, 85-300 nm+/−25 nm, 85-400, 85-2500 nm+/−25 nm, 90-95 nm+/−25 nm, 90-100 nm+/−25 nm, 90-125 nm+/−25 nm, 90-150 nm+/−25 nm, 90-200 nm+/−25 nm, 90-300 nm+/−25 nm, 90-400, 90-2500 nm+/−25 nm, 100-125 nm+/−25 nm, 100-150 nm+/−25 nm, 100-200 nm+/−25 nm, 100-300 nm+/−25 nm, 100-400, 100-2500 nm+/−25 nm, 125-150 nm+/−25 nm, 125-200 nm+/−25 nm, 125-300 nm+/−25 nm, 125-400, 125-2500 nm+/−25 nm, 150-200 nm+/−25 nm, 150-300 nm+/−25 nm, 150-400, 150-2500 nm+/−25 nm, 175-200 nm+/−25 nm, 175-300 nm+/−25 nm, 175-400, 175-2500 nm+/−25 nm, 200-300 nm+/−25 nm, 200-400, 200-2500 nm+/−25 nm, 300-400, 300-2500 nm+/−25 nm, or 400-2500 nm+/−25 nm.

In some embodiments, nanoparticles have a mean particle diameter of 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 125, 150, 175, 200, 224, 250, 275, 300, 325, 350, 375, 400, 425, 450, 475, or 500 nm.

In some embodiments, nanoparticles have a mean particle diameter of 50+/−5 nm, 75+/−5 nm, 100+/−5 nm, 125+/−5 nm, 150+/−5 nm, 175+/−5 nm, 200+/−5 nm, 225+/−5 nm, 250+/−5 nm, 275+/−5 nm, 300+/−5 nm, 325+/−5 nm, 350+/−5 nm, 375+/−5 nm, 400+/−5 nm, 425+/−5 nm, 450+/−5 nm, 475+/−5 nm, or 500+/−5 nm.

In some embodiments, nanoparticles have a mean particle diameter of 50+/−10 nm, 75+/−10 nm, 100+/−10 nm, 125+/−10 nm, 150+/−10 nm, 175+/−10 nm, 200+/−10 nm, 225+/−10 nm, 250+/−10 nm, 275+/−10 nm, 300+/−10 nm, 325+/−10 nm, 350+/−10 nm, 375+/−10 nm, 400+/−10 nm, 425+/−10 nm, 450+/−10 nm, 475+/−10 nm, or 500+/−10 nm.

In some embodiments, nanoparticles have a mean particle diameter of 50+/−15 nm, 75+/−15 nm, 100+/−15 nm, 125+/−15 nm, 150+/−15 nm, 175+/−15 nm, 200+/−15 nm, 225+/−15 nm, 250+/−15 nm, 275+/−15 nm, 300+/−15 nm, 325+/−15 nm, 350+/−15 nm, 375+/−15 nm, 400+/−15 nm, 425+/−15 nm, 450+/−15 nm, 475+/−15 nm, or 500+/−15 nm.

In some embodiments, nanoparticles have a mean particle diameter of 50+/−20 nm, 75+/−20 nm, 100+/−20 nm, 125+/−20 nm, 150+/−20 nm, 175+/−20 nm, 200+/−20 nm, 225+/−20 nm, 250+/−20 nm, 275+/−20 nm, 300+/−20 nm, 325+/−20 nm, 350+/−20 nm, 375+/−20 nm, 400+/−20 nm, 425+/−20 nm, 450+/−20 nm, 475+/−20 nm, or 500+/−20 nm.

In some embodiments, nanoparticles have a mean particle diameter of 50+/−25 nm, 75+/−25 nm, 100+/−25 nm, 125+/−25 nm, 150+/−25 nm, 175+/−25 nm, 200+/−25 nm, 225+/−25 nm, 250+/−25 nm, 275+/−25 nm, 300+/−25 nm, 325+/−25 nm, 350+/−25 nm, 375+/−25 nm, 400+/−25 nm, 425+/−25 nm, 450+/−25 nm, 475+/−25 nm, or 500+/−25 nm.

In some embodiments, nanoparticles have a mean particle diameter of 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, or 125 nm.

Protein molecules can be bound to nanoparticles by various means well-known in the art, including adsorption and covalent coupling. In some embodiments, antibodies are bound to nanoparticles coated with anti-immunoglobulin antibodies (e.g., IgG-coated beads available from Miltenyi Biotec).

Antibodies

Antibodies that specifically bind to antigens or epitopes present on the desired target cells are used to bring antigen-specific T cells in sufficient proximity to the target cells to effect killing of those cells.

Specific binding occurs to the corresponding antigen or epitope even in the presence of a heterogeneous population of proteins and other biologics. "Specific binding" of an antibody means that the binds to its target antigen or epitope with an affinity that is substantially greater than the antibody's binding to an irrelevant antigen or epitope. The relative difference in affinity is often at least 25% greater, more often at least 50% greater, most often at least 100%. The relative difference can be at least 2×, at least 5×, at least 10×, at least 25×, at least 50×, at least 100×, at least 1000×, for example.

"Antibodies" include immunoglobulins (e.g., IgA, IgD, IgE, IgG, IgM) and fragments thereof. Thus, antibodies include human antibodies, chimeric antibodies, and humanized antibodies, and can be polyclonal or monoclonal. Antibody fragments comprise one or more antigen binding or variable regions. Examples of antibody fragments include Fab, Fab', F(ab')$_2$, and Fv fragments; linear antibodies; and single chain antibody molecules.

Depending on the type of antibody employed, an antibody can be isolated, prepared synthetically, or genetically engineered, all using well-known techniques. See, e.g., US 2013/0034566 and US 2013/0028932, both of which are incorporated herein by reference in their entireties.

An ATR can be directed to a variety of target cell types, including tumor cells, cells infected with a pathogen, and cells involved in autoimmune disorders depending on the specificity of the antibody on the ATR.

Tumor-Associated Antigens

In some embodiments, the antibody specifically binds to a tumor-associated antigen or epitope thereof. Tumor-associated antigens include unique tumor antigens expressed exclusively by the tumor from which they are derived, shared tumor antigens expressed in many tumors but not in normal adult tissues (oncofetal antigens), and tissue-specific antigens expressed also by the normal tissue from which the tumor arose. Tumor-associated antigens can be, for example, embryonic antigens, antigens with abnormal post-translational modifications, differentiation antigens, products of mutated oncogenes or tumor suppressors, fusion proteins, or oncoviral proteins.

A variety of tumor-associated antigens are known in the art, and many of these are commercially available. Oncofetal and embryonic antigens include carcinoembryonic antigen and alpha-fetoprotein (usually only highly expressed in developing embryos but frequently highly expressed by tumors of the liver and colon, respectively), MAGE-1 and MAGE-3 (expressed in melanoma, breast cancer, and glioma), placental alkaline phosphatase sialyl-Lewis X (expressed in adenocarcinoma), CA-125 and CA-19 (expressed in gastrointestinal, hepatic, and gynecological tumors), TAG-72 (expressed in colorectal tumors), epithelial glycoprotein 2 (expressed in many carcinomas), pancreatic oncofetal antigen, 5T4 (expressed in gastric carcinoma), alphafetoprotein receptor (expressed in multiple tumor types, particularly mammary tumors), and M2A (expressed in germ cell neoplasia).

Tumor-associated differentiation antigens include tyrosinase (expressed in melanoma) and particular surface immunoglobulins (expressed in lymphomas).

Mutated oncogene or tumor-suppressor gene products include Ras and p53, both of which are expressed in many tumor types, Her-2/neu (expressed in breast and gynecological cancers), EGF-R, estrogen receptor, progesterone receptor, retinoblastoma gene product, myc (associated with lung cancer), ras, p53, nonmutant associated with breast tumors, MAGE-1, and MAGE-3 (associated with melanoma, lung, and other cancers).

Fusion proteins include BCR-ABL, which is expressed in chromic myeloid leukemia.

Oncoviral proteins include HPV type 16, E6, and E7, which are found in cervical carcinoma.

Tissue-specific antigens include melanotransferrin and MUC 1 (expressed in pancreatic and breast cancers); CD10 (previously known as common acute lymphoblastic leukemia antigen, or CALLA) or surface immunoglobulin (expressed in B cell leukemias and lymphomas); the α chain of the IL-2 receptor, T cell receptor, CD45R, CD4$^+$/CD8$^+$ (expressed in T cell leukemias and lymphomas); prostate-specific antigen and prostatic acid-phosphatase (expressed in prostate carcinoma); GP 100, MelanA/Mart-1, tyrosinase, gp75/brown, BAGE, and S-100 (expressed in melanoma); cytokeratins (expressed in various carcinomas); and CD19, CD20, and CD37 (expressed in lymphoma).

Tumor-associated antigens also include altered glycolipid and glycoprotein antigens, such as neuraminic acid-containing glycosphingolipids (e.g., GM$_2$ and GD$_2$, expressed in melanomas and some brain tumors); blood group antigens, particularly T and sialylated Tn antigens, which can be aberrantly expressed in carcinomas; and mucins, such as CA-125 and CA-19-9 (expressed on ovarian carcinomas) or the underglycosylated MUC-1 (expressed on breast and pancreatic carcinomas).

Tissue-specific antigens include epithelial membrane antigen (expressed in multiple epithelial carcinomas), CYFRA 21-1 (expressed in lung cancer), Ep-CAM (expressed in pan-carcinoma), CA125 (expressed in ovarian cancer), intact monoclonal immunoglobulin or light chain fragments (expressed in myeloma), and the beta subunit of human chorionic gonadotropin (HCG, expressed in germ cell tumors).

Antigens of Pathogens

Antigens of pathogens include components of protozoa, bacteria, fungi (both unicellular and multicellular), viruses, prions, intracellular parasites, helminths, and other pathogens that can induce an immune response. Bacterial antigens include antigens of gram-positive cocci, gram positive bacilli, gram-negative bacteria, anaerobic bacteria, such as organisms of the families Actinomvcetaceae, Bacillaceae, Bartonellaceae, Bordetellae, Captophagaceae, Corynebacteriaceae, Enterobacteriaceae, Legionellaceae, Micrococcaceae, Mycobacteriaceae, Nocardiaceae, Pasteurellaceae, Pseudomonadaceae, Spirochaetaceae, Vibrionaceae and organisms of the genera *Acinetobacter, Brucella, Campylobacter, Erysipelothrix, Ewingella, Francisella, Gardnerella, Helicobacter, Levinea, Listeria, Streptobacillus* and *Tropherynma.*

Antigens of protozoan infectious agents include antigens of malarial plasmodia, *Leishmania* species, *Trypanosoma* species and *Schistosoma* species.

Fungal antigens include antigens of *Aspergillus, Blastomyces, Candida, Coccidioides, Cryptococcus, Histoplasma, Paracoccicioides, Sporothrix*, organisms of the order Mucorales, organisms inducing choromycosis and mycetoma and organisms of the genera *Trichophyton, Microsporum, Epidermophyton*, and *Malassezia*.

Antigens of prions include the sialoglycoprotein PrP 27-30 of the prions that cause scrapie, bovine spongiform encephalopathies (BSE), feline spongiform encephalopathies, kuru, Creutzfeldt-Jakob Disease (CJD), Gerstmann-Strassler-Scheinker Disease (GSS), and fatal familial insomnia (FFI).

Intracellular parasites from which antigenic peptides can be obtained include, but are not limited to, Chlamydiaceae, Mycoplasmataceae, Acholeplasmataceae, Rickettsiae, and organisms of the genera *Coxiella* and *Ehrlichia*.

Antigenic peptides can be obtained from helminths, such as nematodes, trematodes, or cestodes.

Viral peptide antigens include, but are not limited to, those of adenovirus, herpes simplex virus, papilloma virus, respiratory syncytial virus, poxviruses, HIV, influenza viruses, and CMV. Particularly useful viral peptide antigens include HIV proteins such as HIV gag proteins (including, but not limited to, membrane anchoring (MA) protein, core capsid (CA) protein and nucleocapsid (NC) protein), HIV polymerase, influenza virus matrix (M) protein and influenza virus nucleocapsid (NP) protein, hepatitis B surface antigen (HBsAg), hepatitis B core protein (HBcAg), hepatitis e protein (HBeAg), hepatitis B DNA polymerase, hepatitis C antigens, and the like.

Autoantigens

An "autoantigen" is an organism's own self antigen to which the organism produces an immune response. Autoantigens are involved in autoimmune diseases such as Goodpasture's syndrome, multiple sclerosis, Graves' disease, myasthenia gravis, systemic lupus erythematosus, insulin-dependent diabetes mellitus, rheumatoid arthritis, pemphigus vulgaris, Addison's disease, dermatitis herpetiformis, celiac disease, and Hashimoto's thyroiditis.

Diabetes-related autoantigens include insulin, glutamic acid decarboxylase (GAD) and other islet cell autoantigens, e.g., ICA 512/IA-2 protein tyrosine phosphatase, ICA12, ICA69, preproinsulin or an immunologically active fragment thereof (e.g., insulin B-chain, A chain, C peptide or an immunologically active fragment thereof), HSP60, carboxypeptidase H, peripherin, gangliosides (e.g., GM1-2, GM3) or immunologically active fragments thereof.

Macular degeneration-associated autoantigens include complement pathway molecules and various autoantigens from RPE, choroid, and retina, vitronectin, β crystallin, calreticulin, serotransferrin, keratin, pyruvate carboxylase, C1, and villin 2.

Other autoantigens include nucleosomes (particles containing histones and DNA); ribonucleoprotein (RNP) particles (containing RNA and proteins that mediate specialized functions in the RNP particle), and double stranded DNA. Still other autoantigens include myelin oligodendrocyte glycoprotein (MOG), myelin associated glycoprotein (MAG), myelin/oligodendrocyte basic protein (MOBP), Oligodendrocyte specific protein (Osp), myelin basic protein (MBP), proteolipid apoprotein (PLP), galactose cerebroside (GalC), glycolipids, sphingolipids, phospholipids, gangliosides and other neuronal antigens.

Moieties that Specifically Bind Antigen-Specific T Cells

ATRs use moieties that specifically bind to antigen-specific T cells to capture the T cells and redirect them to the desired target, using an antibody as described above. The "antigen-specificity" of the T cells refers to the fact that the T cells are subpopulations, e.g., subpopulations of highly effective cytotoxic T cells specific for, e.g., a viral antigen or an antigen from another pathogen, or subpopulations of helper T cells. Several types of moieties can be used for this purpose.

In some embodiments, the moiety is an anti-clonotypic TCR-specific antibody, such as an antibody that specifically binds to a TCR present on a subpopulation of antigen-specific T cells only. These embodiments are advantageous because they do not engage CD8.

In some embodiments, the moiety is an MHC class I-immunoglobulin complex, an MHC class I molecule (e.g., a soluble monomer or multimer), an MHC class II molecule (e.g., a soluble monomer or multimer), or an MHC class II-immunoglobulin complex. Such moieties comprise an antigenic peptide to which the antigen-specific T cell is directed. Useful antigenic peptides include those in the tables, below.

EBV Antigens

| HLA-allele | Peptide 1 | Peptide 2 | Peptide 3 | Peptide 4 | Peptide 5 |
|---|---|---|---|---|---|
| A0201 | GLCTLVAML; SEQ ID NO: 5 | TLDYKPLSV; SEQ ID NO: 11 | CLGGLLTMV; SEQ ID NO: 16 | YVLDHLIVV; SEQ ID NO: 20 | LLWTLVVLL; SEQ ID NO: 23 |
| A2402 | RYSIFFDYM; SEQ ID NO: 6 | TYSAGIVQI; SEQ ID NO: 12 | TYPVLEEMF; SEQ ID NO: 17 | TYGPVFMCL; SEQ ID NO: 21 | DYCNVLNKEF; SEQ ID NO: 24 |
| A0101 | LLWTLVVL; SEQ ID NO: 7 | YSEHPTFTSQY; SEQ ID NO: 13 | TVCGGIMFL; SEQ ID NO: 18 | | |
| A0301 | RLRAEAQVK; SEQ ID NO: 8 | RVRAYTYSK; SEQ ID NO: 14 | | | |
| A1101 | IVTDFSVIK; SEQ ID NO: 9 | AVFDRKSDAK: SEQ ID NO: 15 | SSCSSCPLSKI; SEQ ID NO: 19 | ATIGIAMYK: SEQ ID NO: 22 | FLYALALLLL; SEQ ID NO: 25 |
| A2301 | PYLFWILAAI; SEQ ID NO: 10 | | | | |

| A2 | | A11 | | A24 | |
|---|---|---|---|---|---|
| peptide | SEQ ID NO: | peptide | SEQ ID NO: | peptide | SEQ ID NO: |
| LLDFVRFMGV | 26 | AVFDRKSDAK | 41 | IYVLVMLVL | 49 |
| YLLEMLWRL | 27 | ILTDFSVIK | 42 | PYLFWLAA | 50 |
| FLDKGTYTL | 28 | LPGPQVTAVELHEES | 43 | PYLFWLAAI | 51 |
| ILIYNGWYA | 29 | DEPASTEPVHDQLL | 44 | | |
| SLVIVTTFV | 30 | IVTDFSVIT | 45 | | |
| TLFIGSHVV | 31 | IVTDFSVIR | 46 | | |
| LMIIPLINV | 32 | SLFDRKSDAK | 47 | | |
| VLQWASLAV | 33 | NPTQAPVIQLVHAVY | 48 | | |
| DTPLIPLTIF | 34 | | | | |
| SVRDRLARL | 35 | | | | |
| LLVDLLWLL | 36 | | | | |
| YLQQNWWTL | 37 | | | | |
| YFLEILWRL | 38 | | | | |
| LLSAWILTA | 39 | | | | |
| ALLVLYSFA | 40 | | | | |

CD8+ T Cell Epitopes

Latent Cycle Proteins

| EBV Antigen | Epitope Coordinates | Epitope Sequence | HLA Restriction |
|---|---|---|---|
| EBNA1 | 72-80 | RPQKRPSCI, SEQ ID NO: 52 | B7 |
| | 407-415 | HPVGEADYF, SEQ ID NO: 53 | B53 |
| | 407-417 | HPVGEADYFEY, SEQ ID NO: 54 | B35.01 |
| | 528-536 | IPQCRLTPL, SEQ ID NO: 55 | 137 |
| | 574-582 | VLKDAIKDL, SEQ ID NO: 56 | A2.03 |
| EBNA2 | 14-23 | YHLIVDTDSL, SEQ ID NO: 57 | B38 |
| | 42-51 | DTPLIPLTIF, SEQ ID NO: 58 | A2/B51 |
| | 234-242 | RPTELQPTP, SEQ ID NO: 59 | B55 |
| EBNA3A | 158-166 | QAKWRLQTL, SEQ ID NO: 60 | B8 |
| | 176-184 | AYSSWMYSY, SEQ ID NO: 61 | A30.02 |
| | 246-253 | RYSIFFDY, SEQ ID NO: 62 | A24 |
| | 325-333 | FLRGRAYGL, SEQ ID NO: 63 | B8 |
| | 378-387 | KRPPIFIRRL, SEQ ID NO: 64 | B27 |
| | 379-387 | RPPIFIRRL, SEQ ID NO: 65 | B37 |
| | 406-414 | LEKARGSTY, SEQ ID NO: 66 | B62 |
| | 450-458 | HLAAQGMAY, SEQ ID NO: 67 | |
| | 458-466 | YPLHEQHGM, SEQ ID NO: 68 | B35.01 |
| | 491-499 | VFSDGRVAC, SEQ ID NO: 69 | A29 |
| | 502-510 | VPAPAGPIV, SEQ ID NO: 70 | B7 |
| | 596-604 | SVRDRLARL, SEQ ID NO: 71 | A2 |
| | 603-611 | RLRAEAQVK, SEQ ID NO: 72 | A3 |
| | 617-625 | VQPPQLTLQV, SEQ ID NO: 73 | B46 |
| EBNA3B | 149-157 | HRCQAIRKK, SEQ ID NO: 74 | B27.05 |
| | 217-225 | TYSAGIVQI, SEQ ID NO: 75 | A24.02 |
| | 244-254 | RRARSLSAERY, SEQ ID NO: 76 | B27.02 |
| | 279-287 | VSFIEFVGW, SEQ ID NO: 77 | B58 |
| | 399-408 | AVFDRKSDAK, SEQ ID NO: 78 | A11 |
| | 416-424 | IVTDFSVIK, SEQ ID NO: 79 | A11 |
| | 488-496 | AVLLHEESM, SEQ ID NO: 80 | B35.01 |
| | 657-666 | VEITPYKPTW, SEQ ID NO: 81 | B44 |
| EBNA3C | 163-171 | EGGVGWRHW, SEQ ID NO: 82 | B44.03 |
| | 713-727 | QNGALAINTF, SEQ ID NO: 83 | B62 |
| | 249-258 | LRGKWQRRYR, SEQ ID NO: 84 | B27.05 |
| | 258-266 | RRIYDLIEL, SEQ ID NO: 85 | B27.02/.04/.05 |
| | 271-278 | HHIWQNLL, SEQ ID NO: 86 | B39 |
| | 281-290 | EENLLDFVRF, SEQ ID NO: 87 | B44.02 |
| | 284-293 | LLDFVRFMGV, SEQ ID NO: 88 | A2.01 |
| | 285-293 | LDFVRFMGV, SEQ ID NO: 89 | B37 |
| | 335-343 | KEHVIQNAF, SEQ ID NO: 90 | B44.02 |
| | 343-351 | FRKAQIQGL, SEQ ID NO: 91 | B27.05 |
| | 881-889 | QPRAPIRPI, SEQ ID NO: 92 | B7 |

| EBV Antigen | Epitope Coordinates | Epitope Sequence | HLA Restriction |
|---|---|---|---|
| EBNA-LP | 284-292 | SLREWLLRI, SEQ ID NO: 93 | A2 |
| LMP1 | 38-46 | FWLYIVMSD, SEQ ID NO: 94 | |
| | 72-82 | FRRDLLCPLGA, SEQ ID NO: 95 | B40 |
| | 125-133 | YLLEMLWRL, SEQ ID NO: 96 | A2 |
| | 159-167 | YLQQNWWTL, SEQ ID NO: 97 | A2 |
| | 166-174 | TLLVDLLWL, SEQ ID NO: 98 | A2 |
| | 375-386 | DPHGPVQLSYYD, SEQ ID NO: 99 | B51.1 |
| LMP2 | 1-9 | MGSLEMVPM, SEQ ID NO: 100 | B35.01 |
| | 61-75 | EDPYWGNGDRHSDYQ, SEQ ID NO: 101 | |
| | 121-134 | NPVCLPVIVAPYLF, SEQ ID NO: 102 | |
| | 125-133 | LPVIVAPYL, SEQ ID NO: 103 | B53 |
| | 131-139 | PYLFWLAAI, SEQ ID NO: 104 | A23 |
| | 141-154 | ASCFTASVSTVVTA, SEQ ID NO: 105 | |
| | 144-152 | FTASVSTVV, SEQ ID NO: 106 | A68 |
| | 200-208 | IEDPPFNSL, SEQ ID NO: 107 | B40.01 |
| | 236-244 | RRRWRRLTV, SEQ ID NO: 108 | B27.04 |
| | 237-245 | RRWRRLTVC, SEQ ID NO: 109 | B14.02 |
| | 240-250 | RRLTVCGGIMF, SEQ ID NO: 110 | B27 |
| | 243-251 | TVCGGIMFL, SEQ ID NO: 111 | A1 |
| | 249-262 | MFLACVLVLIVDAV, SEQ ID NO: 112 | |
| | 257-265 | LIVDAVLQL, SEQ ID NO: 113 | A2 |
| | 293-301 | GLGTLGAAI, SEQ ID NO: 114 | A2 |
| | 329-337 | LLWTLVVLL SEQ ID NO: 115 | A2.01 |
| | 340-350 | SSCSSCPLSKI, SEQ ID NO: 116 | A11 |
| | 349-358 | ILLARLFLY, SEQ ID NO: 117 | A29 |
| | 356-364 | FLYALALLL SEQ ID NO: 118 | A2 |
| | 419-427 | TYGPVFMCL, SEQ ID NO: 119 | A24 |
| | 426-434 | CLGGLLTMV, SEQ ID NO: 120 | A2.01 |
| | 442-451 | VMSNTLLSAW, SEQ ID NO: 121 | A25 |
| | 453-461 | LTAGFLIFL, SEQ ID NO: 122 | A2.06 |
| | 447-455 | LLSAWILTA, SEQ ID NO: 123 | A2 |

Lytic Cycle Proteins

| | | | |
|---|---|---|---|
| BRLF1 | 25-39 | LVSDYCNVLNKEFT, SEQ ID NO: 124 | B18 |
| | 25-33 | LVSDYCNVL, SEQ ID NO: 125 | A2.05 |
| | 28-37 | DYCNVLNKEF, SEQ ID NO: 126 | A24 |
| | 91-99 | AENAGNDAC, SEQ ID NO: 127 | B45 |
| | 101-115 | IACPIVMRYYVLDHLI, SEQ ID NO: 128 | A24/C2 |
| | 109-117 | YVLDHLIVV, SEQ ID NO: 129 | A2.01 |
| | 121-135 | FFIQAPSNRVMIPAT, SEQ ID NO: 130 | |
| | 134-142 | ATIGTAMYK, SEQ ID NO: 131 | A11 |
| | 145-159 | KHSRVRAYTYSKVLG, SEQ ID NO: 132 | A3 |
| | 225-239 | RALIKTLPRASYSSH, SEQ ID NO: 133 | A2 |
| | 393-407 | ERPIEFHPSKPTFLP, SEQ ID NO: 134 | Cw4 |
| | 529-543 | QKEEAAICGQMDLS, SEQ ID NO: 135 | B61 |
| | 441-455 | EVCQPKRIRPFHPPG, SEQ ID NO: 136 | |
| BZLF1 | 52-64 | LPEPLPQGQLTAY, SEQ ID NO: 137 | B35.08 |
| | 54-63 | EPLPQGQLTAY, SEQ ID NO: 138 | B35.01 |
| | 81-89 | APENAYQAY, SEQ ID NO: 139 | B35.01 |
| | 101-115 | LQHYREVAA, SEQ ID NO: 140 | C8 |
| | 172-183 | DSELSIKRYKNR, SEQ ID NO: 141 | B18 |
| | 186-201 | RKCCRAKFKQLLQHYR, SEQ ID NO: 142 | C6 |
| | 190-197 | RAKFKQLL, SEQ ID NO: 143 | B8 |
| | 209-217 | SENDRLRLL, SEQ ID NO: 144 | B60 |
| BMLF1 | 265-273 | KDTWLDARM, SEQ ID NO: 145 | |
| | 280-288 | GLCTLVAML, SEQ ID NO: 146 | A2.01 |
| | 397-405 | DEVEFLGHY, SEQ ID NO: 147 | B18 |
| | 435-444 | SRLVRAILSP, SEQ ID NO: 148 | B14 |
| BMRF1 | 20-28 | CYDHAQTHL, SEQ ID NO: 149 | A2 |
| | 86-100 | FRNLAYGRTCVLGKE, SEQ ID NO: 150 | C3/C10 |
| | 116-128 | RPQGGSRPEFVKL, SEQ ID NO: 151 | B7 |
| | 208-216 | TLDYKPLSV, SEQ ID NO: 152 | A2.01 |
| | 268-276 | YRSGIIAVV, SEQ ID NO: 153 | C6 |
| | 268-276 | YRSGIIAVV, SEQ ID NO: 153 | B39 |
| | 286-295 | LPLDLSVILF, SEQ ID NO: 154 | B53 |
| BARF0 | | LLWAARPRL, SEQ ID NO: 155 | A2 |
| BCRF1 | 3-11 | RRLVVTLQC, SEQ ID NO: 156 | B27 |
| BALF2 | 418-426 | ARYAYYLQF, SEQ ID NO: 157 | B27 |
| BILF2 | 240-248 | RRRKGWIPL, SEQ ID NO: 158 | B27 |
| BLLF1 (gp350) | | VLQWASLAV, SEQ ID NO: 159 | A2 |
| BALF4 (gp110) | 276-284 | FLDKGTYTL, SEQ ID NO: 160 | A2 |
| | | ILIYNGWYA, SEQ ID NO: 161 | A2 |
| | | VPGSETMCY, SEQ ID NO: 162 | B35 |
| | | APGWLIWTY, SEQ ID NO: 163 | B35 |
| BXLF2 (gp85) | | TLFIGSHVV, SEQ ID NO: 164 | A2.01 |
| | | SLVIVTTFV, SEQ ID NO: 165 | A2.01 |
| | | LMIIPLINV, SEQ ID NO: 166 | A2.01 |

CD4+ T Cell Epitopes

Latent Cycle Proteins

| EBV Antigen | Epitope Coordinates | Epitope Sequence | HLA Restricted |
|---|---|---|---|
| EBNA1 | 71-85 | RRPQKRPSCIGCKGT, SEQ ID NO: 167 | |
| | 403-417 | RPFFHPVGEADYFEY, SEQ ID NO: 168 | |
| | 429-448 | VPPGAIEQGPADDPGEGPST, SEQ ID NO: 169 | |
| | 434-458 | IEQGPTDDPGEGPSTGPRGQGDGGR, SEQ ID NO: 170 | |
| | 455-469 | DGGRRKKGGWFGRHR, SEQ ID NO: 171 | |
| | 474-493 | SNPKFENIAEGLRVLLARSH, SEQ ID NO: 172 | |
| | 475-489 | NPKFENIAEGLRALL, SEQ ID NO: 173 | |
| | 479-498 | ENIAEGLRVLLARSHVERTT, SEQ ID NO: 174 | DQ7 |
| | 481-500 | IAEGLRALLARSHVERTTDE, SEQ ID NO: 175 | DQ2/3 |
| | 485-499 | LRALLARSHVERTTD, SEQ ID NO: 176 | |
| | 499-523 | EEGNWVAGVFVYGGSKTSLYNLRRG, SEQ ID NO: 177 | DR11 |
| | 509-528 | VYGGSKTSLYNLRRGTALAI, SEQ ID NO: 178 | DR1 |
| | 515-528 | TSLYNLRRGTALAI, SEQ ID NO: 179 | DP3 |
| | 518-530 | YNLRRGTALAIPQ, SEQ ID NO: 180 | |
| | 519-533 | NLRRGRTALAIPQCRL, SEQ ID NO: 181 | |
| | 519-543 | EEGNWVAGVFVYGGSKTSLYNLRRG, SEQ ID NO: 182 | |
| | 527-541 | AIPQCRLTPLSRLPF, SEQ ID NO: 183 | DR-13 |
| | 529-543 | PQCRLTPLSRLPFGM, SEQ ID NO: 184 | DR14 |
| | 544-563 | APGPGPQPLRESIVCYFM, SEQ ID NO: 185 | |
| | 549-568 | PQPGPLRESIVCYFMVFLQT, SEQ ID NO: 186 | |
| | 551-570 | PGPLRESIVCYFMVFLQTHI, SEQ ID NO: 187 | DR1 |
| | 554-573 | LRESIVCYFMVFLQTHIFAE, SEQ ID NO: 188 | |
| | 554-578 | LRESIVCYFMVFLQTHIFAEVLKDA, SEQ ID NO: 189 | |
| | 561-573 | YFMVFLQTHIEAE, SEQ ID NO: 190 | DR11, 12, 13 |
| | 563-577 | MVFLQTHIFAEVLKD, SEQ ID NO: 191 | DR15 |
| | 564-583 | VFLQTHIFAEVLKDAIKDL, SEQ ID NO: 192 | DP5 |
| | 574-593 | VLKDAIKDLVMTKPAPTCNI, SEQ ID NO: 193 | |
| | 589-613 | PTCNIKVTVCSFDDGVDLPPWFPPM, SEQ ID NO: 194 | |
| | 594-613 | RVTVCSFDDGVDLPPWFPPM, SEQ ID NO: 195 | |
| | 607-619 | PPWFPPMVEGAAA, SEQ ID NO: 196 | DQ2 |
| EBNA2 | 11-30 | GQTYHLIVDTLALHGGQTYH, SEQ ID NO: 197 | DR4 |
| | 46-65 | IPLTIFVGENTGVPPPLPPP, SEQ ID NO: 198 | |
| | 131-150 | MRMLWMANYIVRQSRGDRGL, SEQ ID NO: 199 | |
| | 206-225 | LPPATLVPPRPTRPTTLPP, SEQ ID NO: 200 | |
| | 276-295 | PRSTVFYNIPPMPLPPSQL, SEQ ID NO: 201 | DR7, 52a, 52b, 52c |
| | 280-290 | TVFYNIPPMPL, SEQ ID NO: 202 | DQ2/DQ7 |
| | 301-320 | PAQPPPGVINDQQLHHLPSG, SEQ ID NO: 203 | DR17 |
| EBNA3A | 364-383 | EDLPCIVSRGGPKVKRPPIF, SEQ ID NO: 204 | DR15 |
| | 780-799 | GPWVPEQWMFQGAPPSQGTP, SEQ ID NO: 205 | DR1 |
| | 649-668 | QVADVVRAPGVPAMQPQYF, SEQ ID NO: 206 | |
| EBNA3B | | | |
| EBNA3C | 66-80 | NRGWMQRIRRRRRR, SEQ ID NO: 207 | |
| EB-NA3C | 66-80 | NRGWMQRIRRRRRR, SEQ ID NO: 208 | |
| | 100-119 | PHDITYPYTARNIRDAACRAV, SEQ ID NO: 209 | DR13 |
| | 141-155 | ILCFVMAARQRLQDI, SEQ ID NO: 210 | DQ5 |
| | 386-400 | SDDELPYIDPNMEPV, SEQ ID NO: 211 | |
| | 401-415 | QQRPVMFVSRVPAKK, SEQ ID NO: 212 | |
| | 546-560 | QKRAAPPTVSPSDTG, SEQ ID NO: 213 | |
| | 586-600 | PPAAGPPAAGPRILA, SEQ ID NO: 214 | |
| | 626-640 | PPVVRMFMREROLPQ, SEQ ID NO: 215 | |
| | 649-660 | PQCFWEMRAGREITQ, SEQ ID NO: 216 | |
| | 741-760 | PAPQAPYQGYQEPPAPQAPY, SEQ ID NO: 217 | DR1/DR4 |
| | 916-930 | PSMPFASDYSQGAFT, SEQ ID NO: 218 | |
| | 961-986 | AQEILSDNSEISVFPK, SEQ ID NO: 219 | |
| LMP1 | 11-30 | GPPRPPLGPPLSSSIGLALL, SEQ ID NO: 220 | DR7 & DR9 |
| | 130-144 | LWRLGATIWQLLAFF, SEQ ID NO: 221 | |
| | 181-206 | LIWMYYHGPRHTDEHHHDDS, SEQ ID NO: 222 | DR16 |
| | 206-225 | QATDDSSHESDSNSNEGRHH, SEQ ID NO: 223 | DQ2 |
| | 211-236 | SSHESDSNSNEGRHHLLVSG, SEQ ID NO: 224 | DQB1*0601 |
| | 212-226 | SGHESDSNSNEGRHHH, SEQ ID NO: 225 | |
| | 340-354 | TDGGGGHSHDSGHGG, SEQ ID NO: 226 | |

| EBV Antigen | Epitope Coordinates | Epitope Sequence | HLA Restricted |
|---|---|---|---|
| LMP2 | 73-87 | DYQPLGTQDQSLYLG, SEQ ID NO: 227 | DR4 |
| | 149-163 | STVVTATGLALSLLL, SEQ ID NO: 228 | or |
| | 169-182 | SSYAAAQRKLLTPV, SEQ ID NO: 229 | DR16 |
| | 189-208 | VTFFAICLTWRIEDPPFNSI, SEQ ID NO: 230 | |
| | | | DRB1*0901 |
| | 194-713 | ICLTWRIEDPPFNSILFALL, SEQ ID NO: 231 | DRB1*1001 |
| | 224-243 | VLVMLVLLILAYRRRWRRLT, SEQ ID NO: 232 | |
| | 385-398 | STEFIPNLFCMLLL, SEQ ID NO: 233 | |
| | 419-438 | TYGPVFMSLGGLLTMVAGAV, SEQ ID NO: 234 | DQB1*0601 |

Lytic Cycle Proteins

| | | | |
|---|---|---|---|
| BHRF1 | 171-189 | AGLTLSLLVICSYLFISRG, SEQ ID NO: 235 | DR2 |
| | 122-133 | PYYVVDLSVRGM, SEQ ID NO: 236 | DR4 |
| | 45-57 | TVVLRYHVLLEEI, SEQ ID NO: 237 | DR4 |
| BZLF1 | 174-188 | ELEIKRYKNRVASRK, SEQ ID NO: 238 | DR13 |
| | 27-221 | KSSENDRLRLLLKQM, SEQ ID NO: 239 | DQB1*0402 |
| BLLF1 (gp350) | 61-81 | LDLFGQLTPHTKAVYQPRGA, SEQ ID NO: 240 | DRw15 |
| | 65-79 | FGQLTPHTKAVYQPR, SEQ ID NO: 241 | DRB1*1301 |
| | 130-144 | VYFQDVFGTMWCHHA, SEQ ID NO: 242 | DQB1*0402 |
| | 163-183 | DNCNSTNI, SEQ ID NO: 243 TAVVRAQGLDVTL, SEQ ID NO: 244 | DRw11 |
| BALF4 (gp110) | 482-496 | AWCLEQKRQNMVLRE, SEQ ID NO: 245 | DPB1*1301 |
| | 575-589 | DNEIFLTKKIVITEVCQ, SEQ ID NO: 246 | DRB1*0801 |

Influenza Antigens
Immunodominant

M1 $_{58-66}$ GILGFVFTL; SEQ ID NO: 247

Subdominant Peptides

PB1 $_{413-421}$ NMLSTVLGV; SEQ ID NO: 248

NA $_{231-239}$ CVNGSCFTV; SEQ ID NO: 249

PA $_{225-233}$ SLENFRAYV; SEQ ID NO: 250

NS $_{1123-132}$ IMDKNFILKA; SEQ ID NO: 251

NA $_{75-84}$ SLCRIRGWAL SEQ ID NO: 252

PA $_{46-54}$ FMYSDFHFI; SEQ ID NO: 253

Cytomegalovirus (CMV) Antigens

CMVpp65 NLVPMVATV; SEQ ID NO: 254

Measles Antigens

Measles virus H30 LMIDRPYVL; SEQ ID NO: 255

Measles virus H516 ILGQDLQYV; SEQ ID NO: 256

Measles virus H576 KLWCRHFCV; SEQ ID NO: 257

Measles virus C84 KLWESPQEI; SEQ ID NO: 258

In some embodiments, the moiety is an MHC class I-immunoglobulin complex comprising (i) an immunoglobulin molecule comprising two immunoglobulin heavy chains and two immunoglobulin light chains; and (ii) two MHC class I molecules, each comprising an α chain and a $β_2$ microglobulin. Each α chain comprises $α_1$, $α_2$, and $α_3$ domains, and the $α_1$ and $α_2$ domains of each α chain form a peptide binding cleft. The N terminus of each immunoglobulin heavy chain is linked to the N terminus of each $α_3$ domain, and the peptide binding cleft comprises an antigenic peptide recognized by the antigen-specific T cell. Such complexes and their production are described in U.S. Pat. No. 6,268,411, which is incorporated herein by reference in its entirety.

In some embodiments, the moiety is an MHC class I molecule comprising an antigenic peptide recognized by the antigen-specific T cell. In some embodiments, the MHC class I molecule is a soluble monomeric form. In some embodiments, the MHC class I molecule is a soluble multimeric form. See, e.g., U.S. Pat. No. 7,074,905, which is incorporated herein by reference in its entirety.

In some embodiments, the moiety is an MHC class II molecule comprising an antigenic peptide recognized by the antigen-specific T cell. In some embodiments, the MHC class II molecule is a soluble monomeric form. In some embodiments, the MHC class II molecule is a soluble multimeric form. See, e.g., U.S. Pat. No. 7,074,905, which is incorporated herein by reference in its entirety.

In some embodiments, the moiety is an MHC class II-immunoglobulin complex comprising four fusion proteins. Two first fusion proteins comprise (1) an immunoglobulin heavy chain, and (2) an extracellular domain of an MHC class II chain; and two second fusion proteins comprise (1) an immunoglobulin light chain and (2) an extracellular domain of an MHC class II α chain. The fusion proteins associate to form the molecular complex, which comprises two ligand binding sites, each ligand binding site formed by the extracellular domains of the α and β chains. Such complexes and their production are described in U.S. Pat. No. 6,015,884, which is incorporated herein by reference in its entirety.

If desired, an ATR may comprise various combinations of antibodies that specifically bind to antigens or epitopes present on the desired target cells and moieties that specifically bind to antigen-specific T cells, and these components may be present at a variety of ratios. For example, the following embodiments are possible.

1. In some embodiments, an ATR comprises a first antibody that specifically binds to a first antigen or first epitope present on a desired target cell.
2. The some embodiments, the ATR is an ATR of embodiment 1 and comprises a second antibody that specifically binds to a second antigen or second epitope present on a desired target cell, wherein the first antigen or first epitope is different than the second antigen or second epitope.
3. In some embodiments, the ATR is an ATR of embodiment 1 or 2 and comprises a first anti-clonotypic TCR-specific antibody.
4. In some embodiments, the ATR is an ATR of embodiment 1, 2, or 3 and comprises a second anti-clonotypic TCR-specific antibody.
5. In some embodiments, the ATR is an ATR of embodiment 1, 2, 3, or 4 and comprises an a first MHC-Ig complex comprising a first antigenic peptide.
6. In some embodiments, the ATR is an ATR of embodiment 1, 2, 3, 4, or 5 and comprises a second MHC-Ig complex comprising a second antigenic peptide, wherein the second antigenic peptide is different from the first antigenic peptide.
7. In some embodiments, the ATR is an ATR of embodiment 6 and comprises a first monomeric MHC class I molecule comprising a third antigenic peptide.
8. In some embodiments, the ATR is an ATR of embodiment 7 in which the third antigenic peptide is the same as the first antigenic peptide of embodiment 5.
9. In some embodiments, the ATR is an ATR of embodiment 7 in which the third antigenic peptide is different than the first antigenic peptide of embodiment 5.
10. In some embodiments, the ATR is an ATR of embodiment 8 or 9 and comprises a second monomeric MHC class I molecule comprising a fourth antigenic peptide.
11. In some embodiments, the ATR is an ATR of embodiment 10 in which the fourth antigenic peptide is the same as the third antigenic peptide of embodiment 7.
12. In some embodiments, the ATR is an ATR of embodiment 10 in which the fourth antigenic peptide is different than the third antigenic peptide of embodiment 7.
13. In some embodiments, the ATR is an ATR of embodiment 11 or 12 and comprises a first multimeric MHC class I molecule comprising a fifth antigenic peptide.
14. In some embodiments, the ATR is an ATR of embodiment 13 in which the fifth antigenic peptide is the same as the fourth antigenic peptide of embodiment 10.
15. In some embodiments, the ATR is an ATR of embodiment 13 in which the fifth antigenic peptide is different than the fourth antigenic peptide of embodiment 10.
16. In some embodiments, the ATR is an ATR of embodiment 14 or 15 and comprises a second multimeric MHC class I molecule comprising a sixth antigenic peptide.
17. In some embodiments, the ATR is an ATR of embodiment 16 in which the sixth antigenic peptide is the same as the fifth antigenic peptide of embodiment 13.
18. In some embodiments, the ATR is an ATR of embodiment 16 in which the sixth antigenic peptide is different than the fifth antigenic peptide of embodiment 13.
19. In some embodiments, the ATR is an ATR of embodiment 17 or 18 and comprises a first monomeric MHC class II molecule comprising a seventh antigenic peptide.
20. In some embodiments, the ATR is an ATR of embodiment 19 in which the seventh antigenic peptide is the same as the sixth antigenic peptide of embodiment 16.
21. In some embodiments, the ATR is an ATR of embodiment 19 in which the seventh antigenic peptide is different than the sixth antigenic peptide of embodiment 16.
22. In some embodiments, the ATR is an ATR of embodiment 20 or 21 which comprises a second monomeric MHC class II molecule comprising an eighth antigenic peptide.
23. In some embodiments, the ATR is an ATR of embodiment 22 in which the eighth antigenic peptide is the same as the seventh antigenic peptide of embodiment 19.
24. In some embodiments, the ATR is an ATR of embodiment 22 in which the eighth antigenic peptide is different than the seventh antigenic peptide of embodiment 19.
25. In some embodiments, the ATR is an ATR of embodiment 23 or 24 which comprises a first multimeric MHC class II molecule comprising a ninth antigenic peptide.
26. In some embodiments, the ATR is an ATR of embodiment 25 in which the ninth antigenic peptide is the same as the eighth antigenic peptide of embodiment 22.
27. In some embodiments, the ATR is an ATR of embodiment 25 in which the ninth antigenic peptide is different than the eighth antigenic peptide of embodiment 22.
28. In some embodiments, the ATR is an ATR of embodiment 26 or 27 which comprises a first MHC class II immunoglobulin complex comprising a tenth antigenic peptide.
29. In some embodiments, the ATR is an ATR of embodiment 28 in which the tenth antigenic peptide is the same as the ninth antigenic peptide of embodiment 25.
30. In some embodiments, the ATR is an ATR of embodiment 28 in which the tenth antigenic peptide is different than the ninth antigenic peptide of embodiment 25.
31. In some embodiments, the ATR is an ATR of embodiment 29 or 30 which comprises a second MHC class II immunoglobulin complex comprising an eleventh antigenic peptide.
32. In some embodiments, the ATR is an ATR of embodiment 31 in which the eleventh antigenic peptide is the same as the tenth antigenic peptide of embodiment 28.
33. In some embodiments, the ATR is an ATR of embodiment 31 in which the eleventh antigenic peptide is the same as the tenth antigenic peptide of embodiment 28.

Redirecting Fusion Proteins

It is also possible to use fusion proteins comprising (A) an antibody that specifically binds to an antigen or epitope thereof present on a desired target cell and (B) a moiety that specifically binds antigen-specific effector T cells to redirect specific effector T cell population to the target cells ("redirecting fusion proteins"); i.e., these fusion proteins function as ATR but without use of a nanoparticle substrate. Redirecting fusion proteins use the same components described above for (A) and (B) and can be prepared using routine techniques well known in the art, including recombinant production and production via chemical synthesis.

Compositions

Compositions comprising ATRs and/or redirecting fusion proteins typically are liquid compositions, containing, e.g., water, saline, glycerol, or other pharmaceutically acceptable liquid components. Compositions can comprise a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in compositions, for example, mineral salts such as hydrochlorides, hydrobromides, phosphates, or sulfates, as well as salts of organic acids such as acetates, proprionates, malonates, or benzoates. Compositions can also contain, e.g., wetting agents, emulsifying agents, pH buffering agents, and the like.

Methods of Treatment

ATRs and/or redirecting fusion proteins can be used to treat patients with tumors, e.g., cancer, infectious diseases or autoimmune disorders.

Any tumor cell bearing a tumor-specific antigen or epitope thereof can be targeted. Thus, cancers that can be treated include melanoma, carcinomas, e.g., colon, duodenal, prostate, breast, ovarian, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies, e.g., neuroblastoma, gliomas, etc.; hematological malignancies, e.g., chronic myelogenous leukemia, childhood acute leukemia, non-Hodgkin's lymphomas, chronic lymphocytic leukemia, malignant cutaneous T-cells, mycosis fungoides, non-MF cutaneous T-cell lymphoma, lymphomatoid papulosis, T-cell rich cutaneous lymphoid hyperplasia, bullous pemphigoid, and discoid lupus erythematosus.

Infectious diseases that can be treated include those caused by bacteria, viruses, prions, fungi, parasites, helminths, etc. Such diseases include AIDS, hepatitis, CMV infection, and post-transplant lymphoproliferative disorder (PTLD). CMV, for example, is the most common viral pathogen found in organ transplant patients and is a major cause of morbidity and mortality in patients undergoing bone marrow or peripheral blood stem cell transplants (Zaia, *Hematol. Oncol. Clin. North Am.* 4, 603-23, 1990). This is due to the immunocompromised status of these patients, which permits reactivation of latent virus in seropositive patients or opportunistic infection in seronegative individuals. Current treatment focuses on the use of antiviral compounds such as gancyclovir, which have drawbacks, the most significant being the development of drug-resistant CMV. TCRBs provide a useful alternative to these treatments.

Post-transplant lymphoproliferative disease (PTLD) occurs in a significant fraction of transplant patients and results from Epstein-Barr virus (EBV) infection. EBV infection is believed to be present in approximately 90% of the adult population in the United States (Anagnostopoulos & Hummel, *Histopathology* 29, 297-315, 1996). Active viral replication and infection is kept in check by the immune system, but, as in cases of CMV, individuals immunocompromised by transplantation therapies lose the controlling T cell populations, which permits viral reactivation. This represents a serious impediment to transplant protocols. EBV may also be involved in tumor promotion in a variety of hematological and non-hematological cancers. There is also a strong association between EBV and nasopharyngeal carcinomas. Thus, treatment with TCRBs offers an excellent alternative to current therapies.

Autoimmune disorders that can be treated include Goodpasture's syndrome, multiple sclerosis, Graves' disease, myasthenia gravis, systemic lupus erythematosus, insulin-dependent diabetes mellitus, rheumatoid arthritis, pemphigus vulgaris, Addison's disease, dermatitis herpetiformis, celiac disease, and Hashimoto's thyroiditis.

In some embodiments, ATRs and/or redirecting fusion proteins are prepared and administered directly to the patient. In some embodiments, T lymphocytes are removed from a patient and placed in contact with ATRs and/or redirecting fusion proteins to expand an antigen-specific population of cytotoxic T cells. The cytotoxic T cells and ATRs and/or redirecting fusion proteins are then administered to the patient. Optionally, with either approach, the patient can be vaccinated against the antigen to which the T cell redirection bead is directed.

Routes of administration include intravenous, intraperitoneal, and subcutaneous administration.

Doses

A therapeutically effective dose of ATRs and/or redirecting fusion proteins is one that will produce a desired effect in the patient, e.g., alleviation of some symptom associated with the disease being treated, such as tumor shrinkage. The particular dosages of ATRs and/or redirecting fusion proteins employed for a particular method of treatment will vary according to the condition being treated, the binding affinity of the antibody for its target, the extent of disease progression, etc. For example, the actual dose and schedule may vary depending on whether the compositions are administered in combination with other pharmaceutical compositions, or depending on individual differences in pharmacokinetics, drug disposition, and metabolism. One skilled in the art can easily make any necessary adjustments in accordance with the necessities of the particular situation.

In some embodiments, ATRs are administered to patients in doses ranging from about 0.5-2.5 mg ATR/kg of body weight (~$1.1 \times 10^{13}$ ATR); e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, or 2.5 ATR/kg. In some embodiments, redirecting fusion proteins are administered to patients in doses ranging from about 1 µg/kg to 100 mg/kg (e.g., from about 0.05 mg/kg to about 10 mg/kg; 0.5 mg/kg, 2.0 mg/kg, 4.0 mg/kg, or 10 mg/kg or any combination thereof).

Animal Models

A number of murine models are available to assess immunotherapy protocols for tumor treatment. Two models are particularly suitable for assessing melanoma treatment. One model uses human/SCID mice bearing a subcutaneous implanted human melanoma line, such as BML. In such models, transfer of ex vivo expanded Mart-1-specific CTL delays the onset and/or growth of the tumor. A second model uses the murine A2-transgenic mice and the murine B16 melanoma that has been transfected with an HLA-A2-like molecule, called AAD. This molecule, which is also the basis of the A2-transgenic, is human HLA-A2 in alpha 1-2 domains fused to the murine alpha3 domain. Using these transgenic mice, the murine B16-AAD melanoma is sensitive to rejection across well-defined A2-restricted melanoma epitopes derived from tyrosinase and gp100.

Kits

ATRs and/or redirecting fusion proteins can be provided in kits. Suitable containers include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

A kit can further comprise a second container comprising a pharmaceutically-acceptable buffer, such as phosphate-buffered saline, Ringer's solution, or dextrose solution. It can also contain other materials useful to an end user, including other buffers, diluents, filters, needles, and syringes. A kit can also comprise a second or third container with another active agent, for example a chemotherapeutic agent or an anti-infective agent.

Kits also can contain reagents for assessing the extent and efficacy of antigen-specific T cell, such as antibodies against specific marker proteins.

A kit can also comprise a package insert containing written instructions for treatment methods described herein. The package insert can be an unapproved draft package insert or can be a package insert approved by the Food and Drug Administration (FDA) or other regulatory body.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

Example 1

Material and Methods i. Mice and Reagents

2C TCR Rag$^{-/-}$ transgenic mice were maintained as heterozygotes by breeding on a C57/BL6 background. Pmel TCR/Thy1$^a$ Rag–/– transgenic mice were a gift from Nicholas Restive (National Institutes of Health (NIH), Bethesda, Md.) and maintained as homozygotes. All mice were maintained according to The Johns Hopkins University's Institutional Review Board. Peptides "SIY" (SIYRYYGL, SEQ ID NO:1), "SIIN" (SIINFEKL, SEQ ID NO:2), "QL9" (QLSPFPFDL, SEQ ID NO:3) and "GP 100" (KVPRNQDWL, SEQ ID NO:4) were purchased from GenScript (Piscataway, N.J.).

ii. Cells

CD8$^+$ cells were isolated from homogenized mouse spleens after depletion of red blood cells by hypotonic lysis using a mouse CD8$^+$ isolation kit (Miltenyi Biotec) according to the manufacturer's instructions. 1×10$^6$ CD8$^+$ cells were plated on a 96 well U-bottom plate and co-cultured for 7 days at a 1:1 ratio with cognate loaded beads in complete RPMI media supplemented with T cell factor (Durai, Cancer Immunol. Immunother., 58, 2009, pp. 209-220). On day 7, cells were harvested, and beads were removed. Density gradient centrifugation was performed to ensure viability of >95%.

Human T2 cells (HLA-A*0201) were obtained from ATCC and cultured in complete RPMI media. Two days before use, cells were split 1:10 to achieve maximal viability. Viability was determined by Trypan blue exclusion.

iii. Preparation of MHC-Ig Dimers

Soluble MHC-Ig dimers, K$^b$-Ig, L$^d$-Ig, and D$^b$-Ig, were loaded with peptide as described previously (Dal Porto, Proc. Natl. Acad. Sci. USA, 90, 1993, pp. 6671-75). Briefly, dimer molecules were loaded with peptide by stripping at alkaline (pH 11.5) or mildly acidic (pH 6.5) conditions, then refolded in the presence of 40-fold excess peptide and twofold molar excess of human β$_2$-microglobulin (Lebowitz, Cell. Immunol., 192, 1999), pp. 175-84). Unless otherwise indicated, "K$^b$-SIY," "K$^b$-SIIN," "L$^d$-QL9," and "D$^b$-gp100" refer to nano-bead bound MHC-Ig dimer reagent loaded with the indicated peptide.

iv. Bead Preparation

100 µl of anti-mouse IgG$_1$ microbeads ("beads;" Miltenyi Biotec) were transferred into a sterile glass vial. Either 5 µg 1B2 (an anti-clonotypic 2C TCR-specific mAb; mouse IgG$_1$ isotype) or 5 µg peptide loaded MHC-Ig (K$^b$-SIY, K$^b$-SIIN, L$^d$-QL9, or D$^b$-gp100) were added. Each redirection bead received an additional 5 µg of an anti-human CD19 mAb (clone HIB19, BD, Mountain View, Calif.). All control beads were made with 5 µg of a single molecule or antibody. To allow binding, beads were incubated at 4° C. for at least 1 hour. Beads were then washed 3 times with 1 ml PBS using a MS-column (Miltenyi Biotec) and eluted in 1 ml PBS into a new glass vial resulting in a 1/10 dilution of the original stock concentration. Binding of MHC-Ig and antibodies to beads was analyzed by flow cytometric staining of target-bearing cells.

v. Bead Staining and Flow Cytometry

Unless otherwise indicated, 0.2×10$^6$ cells were incubated with 50 µl beads at 4° C. for 45 minutes. Cells were then washed with 10 volumes of PBS. To detect specific binding of beads to cells, bead-labeled cells were secondarily stained with a 1:200 α-mouse IgG1 mAb-PE (Invitrogen) at 4° C. for 10 to 15 minutes. All FACS analysis was carried out on a FACSCALIBUR™ (BD Biosciences, Mountain View; CA) and analyzed using FlowJo software (Treestar, Ashland, Oreg.).

vi. Conjugation Assay

T2 target cells and activated CD8+ effector cells were stained as previously published (Schütz C, J. Immunol. Methods. 2009; 344(2):98-108) with 2 µM PKH67 and PKH26 (Sigma, St. Louis, Mo.) respectively. 0.1×10$^6$ target cells were co-cultured at a 1:1 ratio with CD8+ effector cells in 80 µl PBS supplemented with 10% fetal calf serum and plated on a 96 well U-bottom plate. Unless otherwise indicated, 50 µl of bead were added to each sample and incubated overnight (18-24 h) at 4° C. (co-culture protocol). On the next day, samples were analyzed by flow cytometry, without washing and with minimal agitation. The amount of conjugate formation (i.e., beads bound to both effector and target cells) was determined by gating on PKH67 and PKH26 double positive cells.

vii. Pre-Targeted Protocol

Compared to the co-culture protocol, CD8$^+$ effector cells (0.2×10$^6$) were first incubated with beads at 4° C. for 15-45 minutes. Afterwards, cells were washed with 10 volumes of PBS to eliminate all unbound beads and re-suspended into co-culture media. Pre-targeted CD8$^+$ effector cells were used within the next hour, and binding was evaluated by staining prior to each experimental set up, as described above.

viii. In Vitro Redirection Killing Assay

Cytotoxic activity of redirected CD8$^+$ cells was measured by 18-20 hour $^{51}$Cr release assay using triplicate cultures in V-bottom plates. 0.2×10$^6$/plate T2 target cells were pulsed with 200 µCi $^{51}$Cr at 37° C. for 1 hour. E:T ratios were 1:2, 1:1, 2:1, 5:1 and 10:1 on 2000 target cells/well. To allow proper cell contact, plates were spun down (300×g, 5 minutes) just before incubation. The counts from triplicate wells were averaged and percentage specific cytotoxicity was calculated as [(cpm sample–cpm spontaneous release)×100/ (cpm maximum release–cpm spontaneous release)]. For spontaneous release, target cells were plated without CD8$^+$ cells in complete RPMI media. For maximum release, target cells were plated with 0.15% TRITON™ X-100 (Sigma, St. Louis, Mo.). For analysis of bead mediated redirection properties, standard and pre-targeted protocol were run simultaneously.

Example 2

Generation of Functional Nano-Bead Based Redirection Beads

Close cell-cell contact is important for effective and specific killing. We tested 50-100 nm sized beads for the ability to achieve sufficient cell-cell membrane apposition. The beads were coated with different T cell targeting complexes, either an MHC-Ig complex or an anti-clonotypic antibody complex (FIG. 1A). Both sets of beads were made by simultaneously coating with an anti-human-CD19 to target human B cells. Both the clonotypic anti-TCR antibody and MHC-Ig complex engage the 2C TCR cell, which is a model transgenic allospecific CD8+ T cell.

To evaluate the effective binding of the redirection beads to their targets, 2C effector cells (FIG. 1B, upper panel) or T2 target cells (FIG. 1B, lower panel), were incubated with redirection beads, washed extensively and stained an anti-mouse IgG$_1$ PE mAb. The anti-mouse IgG$_1$ PE mAb antibody is specific for the Fc portion of all molecules on the redirection beads and thus were able to visualize redirection beads bound to cells. Data was analyzed by flow cytometry.

Figure 1B:
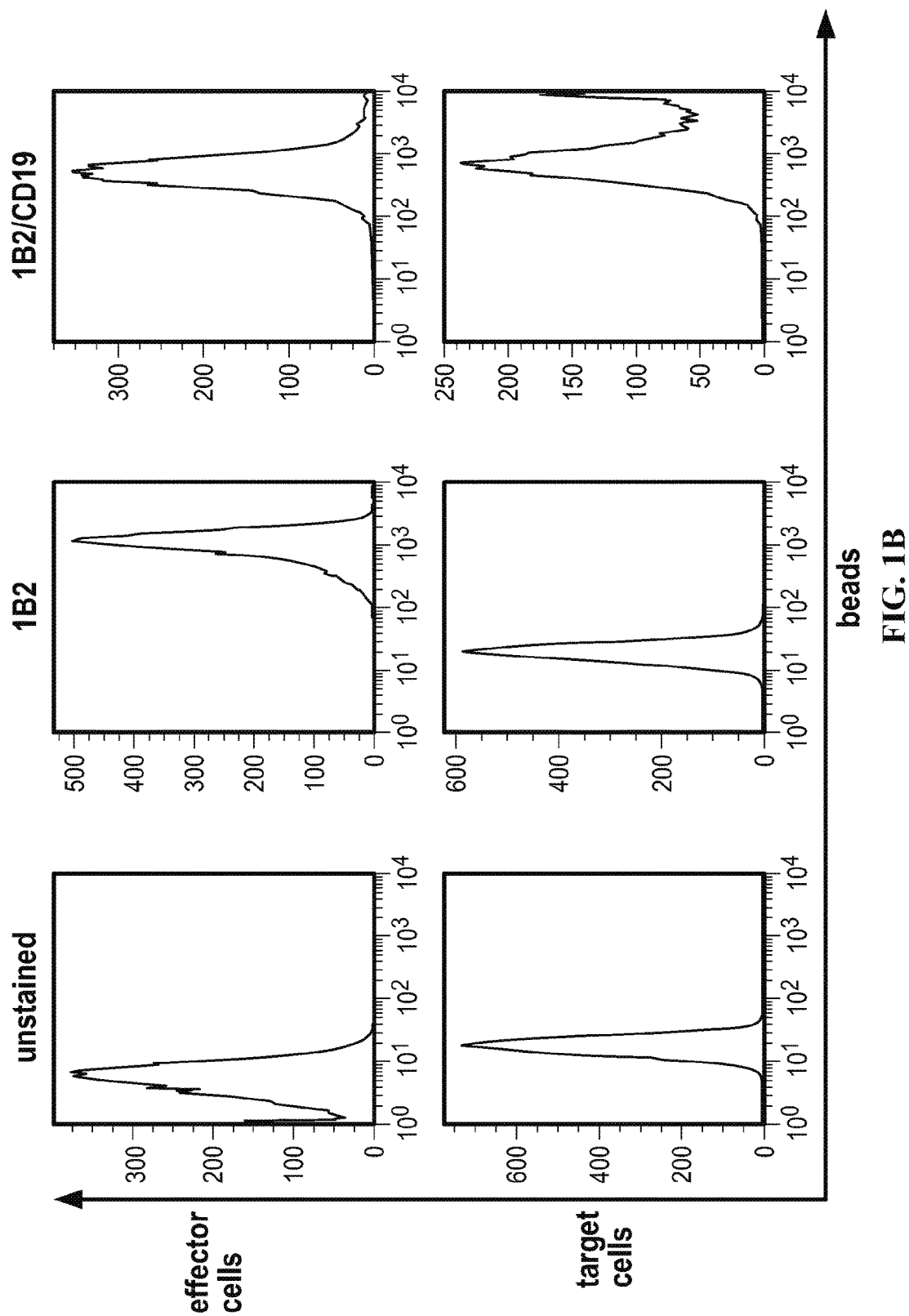
FIG. 1B. Graphs showing results of flow cytometry experiments (Example 2). Effector cells (2C CD8$^+$ T cells) and target cells (T2) were incubated with various types of beads at 4° C. for 15 minutes, washed, and stained with phycoerythrin-conjugated anti-mouse-IgG$_1$ ("anti-mouse IgG$_1$ PE"). "MHC-Ig" represents labeling of 2C or T2 cells with SIY peptide loaded K$^b$-Ig generated redirection beads at 4° C. for 45 min.
Figure 1B:
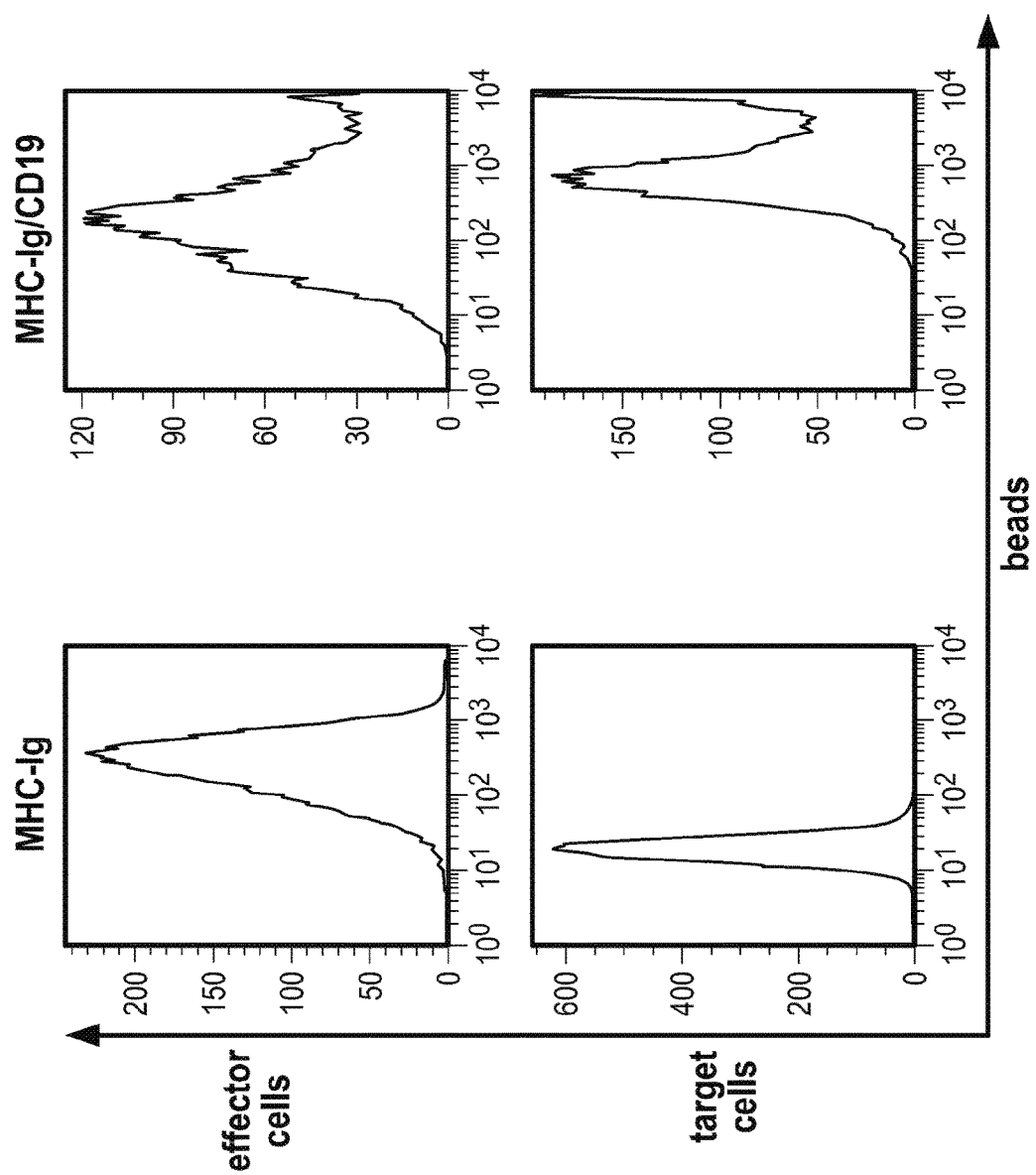

Anti-CD19 specific beads (1B2/CD19 and MHC-Ig/CD19) bound to T2 cells (FIG. 1B lower panel). Beads containing TCR specific ligands (1B2, 1B2/CD19, MHC-Ig, and MHC-Ig/CD19 beads) bound to 2C cells. This data indicates that beads coated with antibody (1B2 mAb) and MHC-Ig (SIY-Kb-Ig) can be generated and are capable of specifically targeting 2C cells and T2 cells simultaneously.

Example 3

Redirection Beads Induce Antigen-Specific Effector/Target Cell Conjugates

Figure 2A:
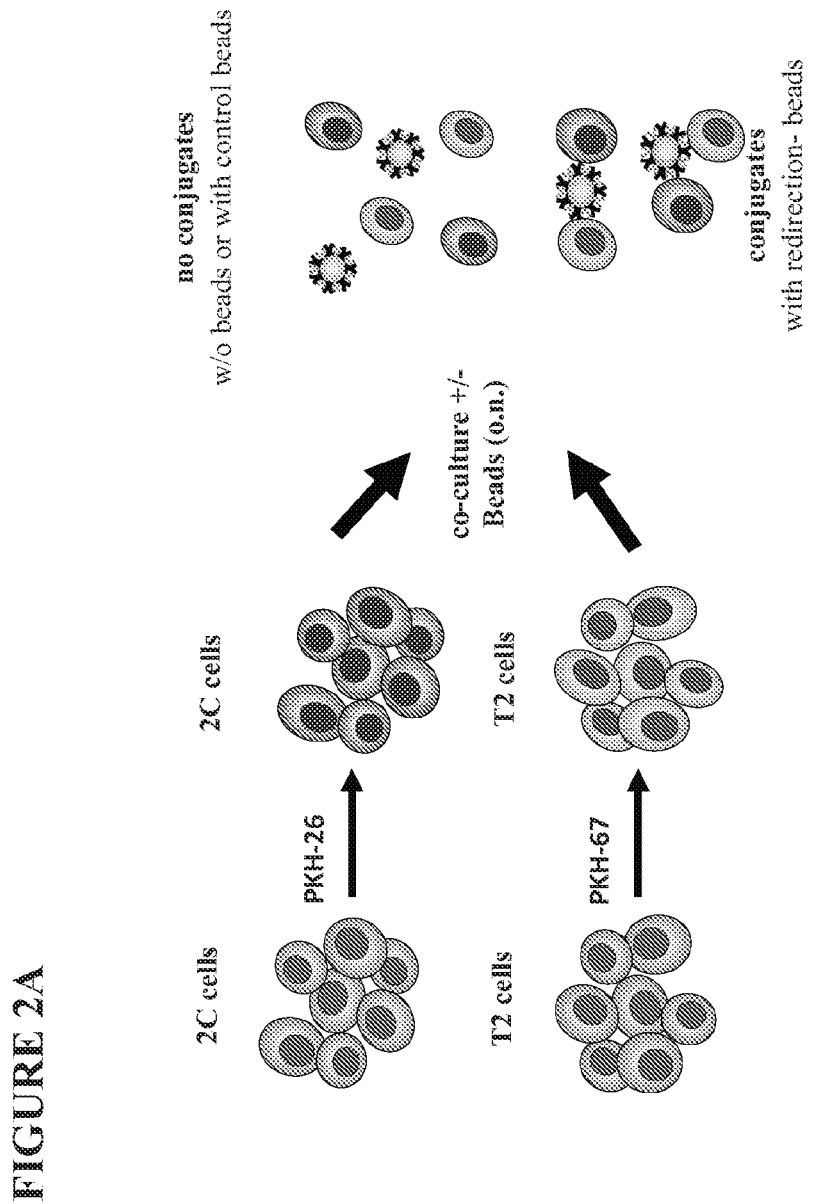
FIGS. 2A-C. Redirection beads induce conjugate formation (Example 3).

A flow cytometry based conjugation assay was used to investigate if redirection beads are able to bring a specific effector cell in close proximity to a target cell (Schütz C, J. Immunol. Methods. 2009; 344(2):98-108). 2C effector cells were stained with a red fluorescent membrane dye (PKH26), and T2 target cells stained with a green fluorescent membrane dye (PKH67). The use of different membrane dyes for two different cell populations allowed for cell type specific discrimination after co-culture with or without control or redirection beads. Co-cultures with redirection beads should show enhanced 2C/T2 conjugate formation, represented by an increased population of PKH26 (red) and PKH67 (green) double positive cells (schematic, FIG. 2A).

Figure 2B:
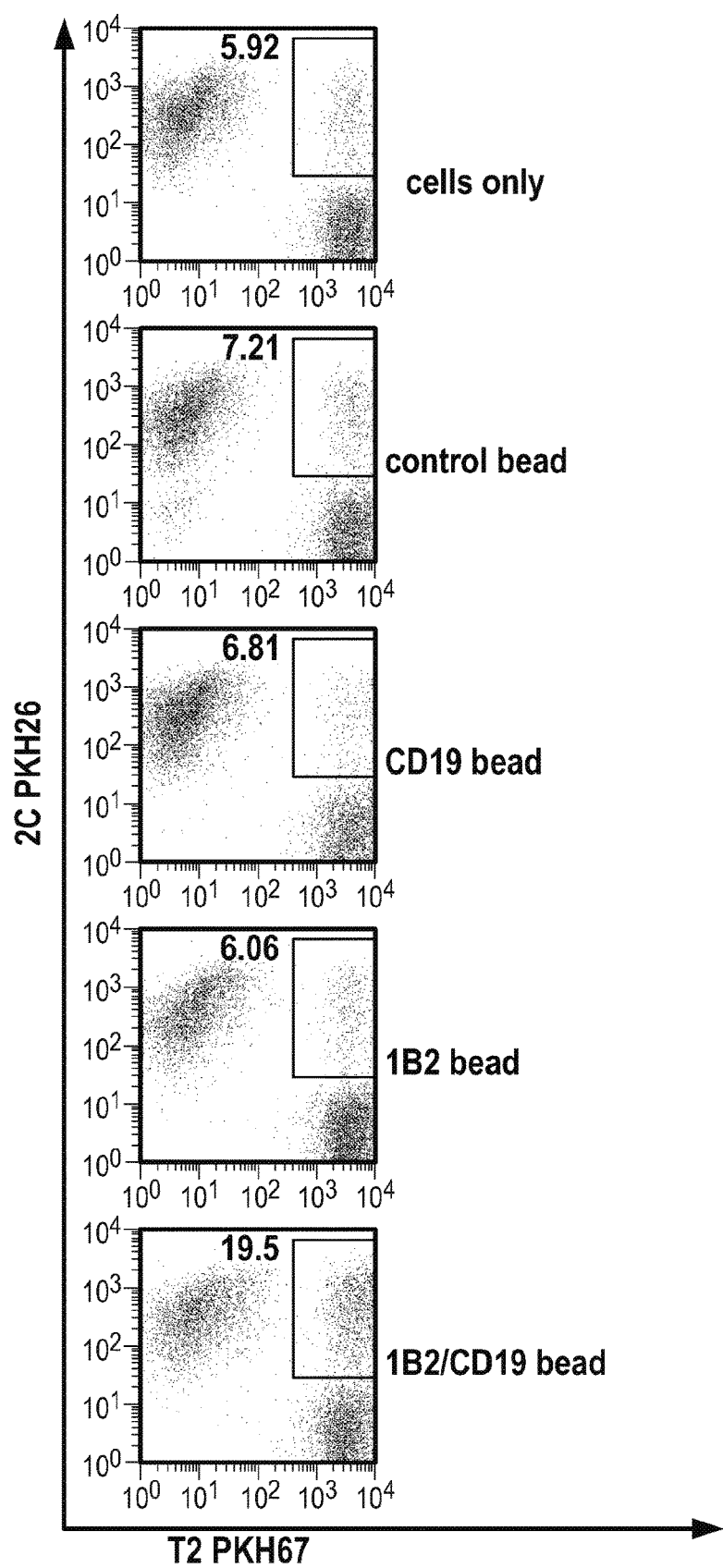
Figure 2C:
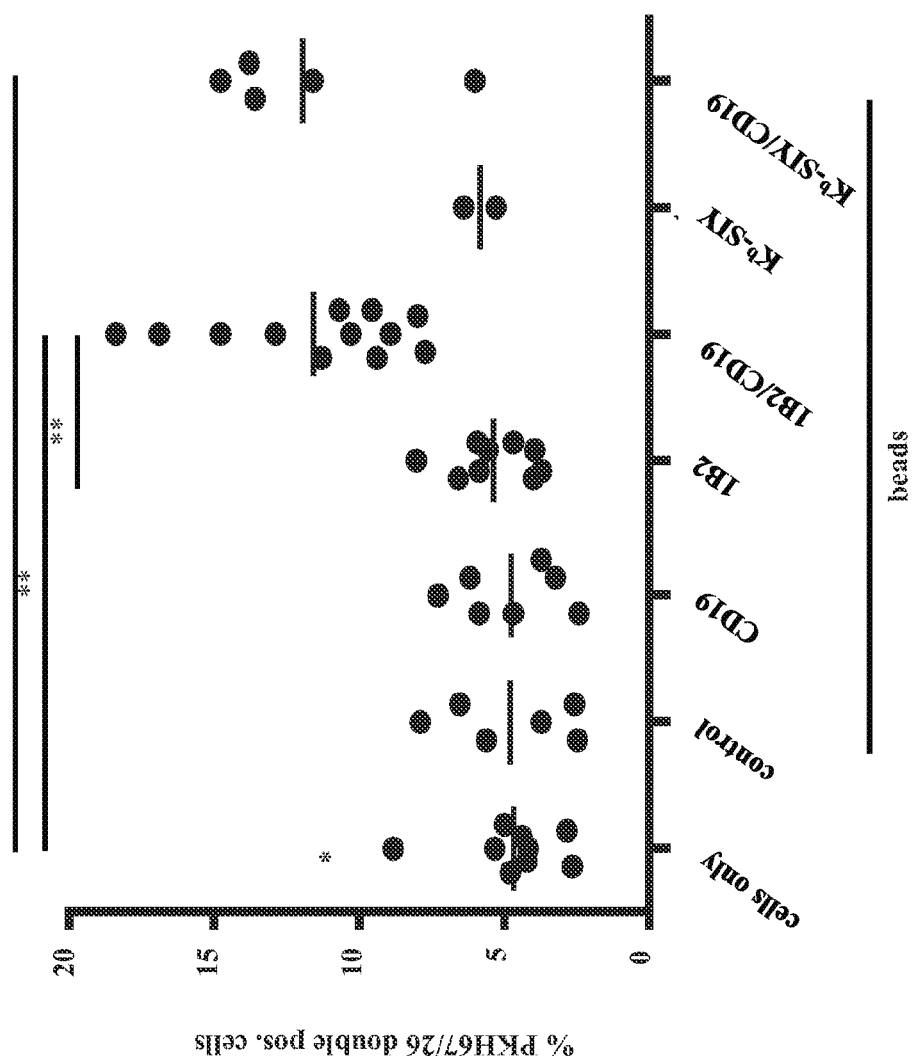

As shown in FIG. 2B, in the presence of redirection bead (1B2/CD19) co-cultures had increased amounts (19.5%, FIG. 2B) of PKH26/67 double positive cell conjugates, whereas all control beads (1B2, CD19, control) showed only background conjugate formation (6.06-7.21%, FIG. 2B), which did not significantly exceed levels of conjugates in samples without beads (5.92% cells only, FIG. 2B). A summary of conjugate formation assay shows that 2C/T2 conjugate (PKH26/67) formation is highly significant ($p<0.001$) in the presence of redirection beads when compared to controls (FIG. 2C). While both antibody (1B2/CD19) and dimer (Kb-SIY-g) based redirection beads induced conjugate formation, redirection beads made with an irrelevant T cells targeting moiety, Kb-SIIN-Ig, did not show an increased PKH26/67 double positive population (data not shown).

Example 4

Specificity, Stability and Ratio Dependence of Bead to Target Cell Binding

Figure 3A:
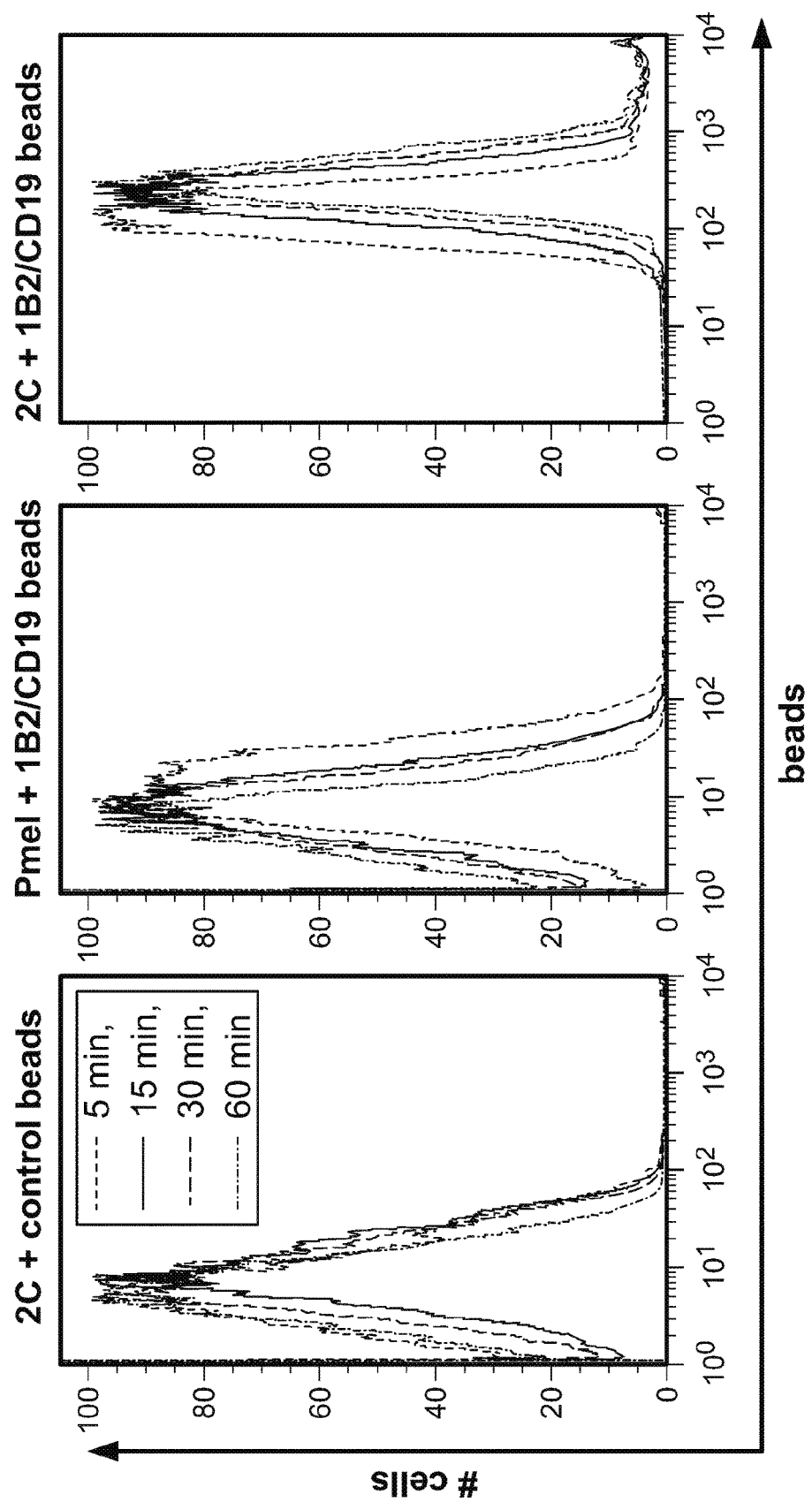
FIGS. 3A-C. Specificity and stability of pre-targeted 1B2/CD19 bead binding (Example 4).

To set up an optimal protocol for a later killing assay, we initially investigated bead to cell binding conditions. First, we verified the specificity of an effector cell bead stain and determined the minimal staining time that resulted in a sufficient coating of effector cells with beads (FIG. 3A). 2C cells were incubated with 50 µl of either control or 1B2/CD19 beads. After different time points (5, 15, 30 and 60 min), cells were secondarily stained with anti-mouse IgG$_1$ to determine the amount of bound beads. While no binding was been detected at any time point when stained with control beads (FIG. 3A, left panel), good binding was detected on 2C cells incubated with 1B2/CD19 beads (FIG. 3A, right panel). Fifteen minutes was an optimal staining interval, and MFI intensity was increased only minimally at later time points. Furthermore, staining of tumor-antigen gp-100 specific, transgenic CD8+ Pmel effector T cells with 1B2/CD19 beads (FIG. 3A, middle panel) did not shown any binding. This finding is in line with the fact that 1B2 detects only the transgenic T cell receptor (TCR) of 2C cells. Experiments using Kb-SIY-Ig and Kb-OVA-Ig redirection beads also showed antigen-specific binding to 2C effector cells (data not shown).

Figure 3B:
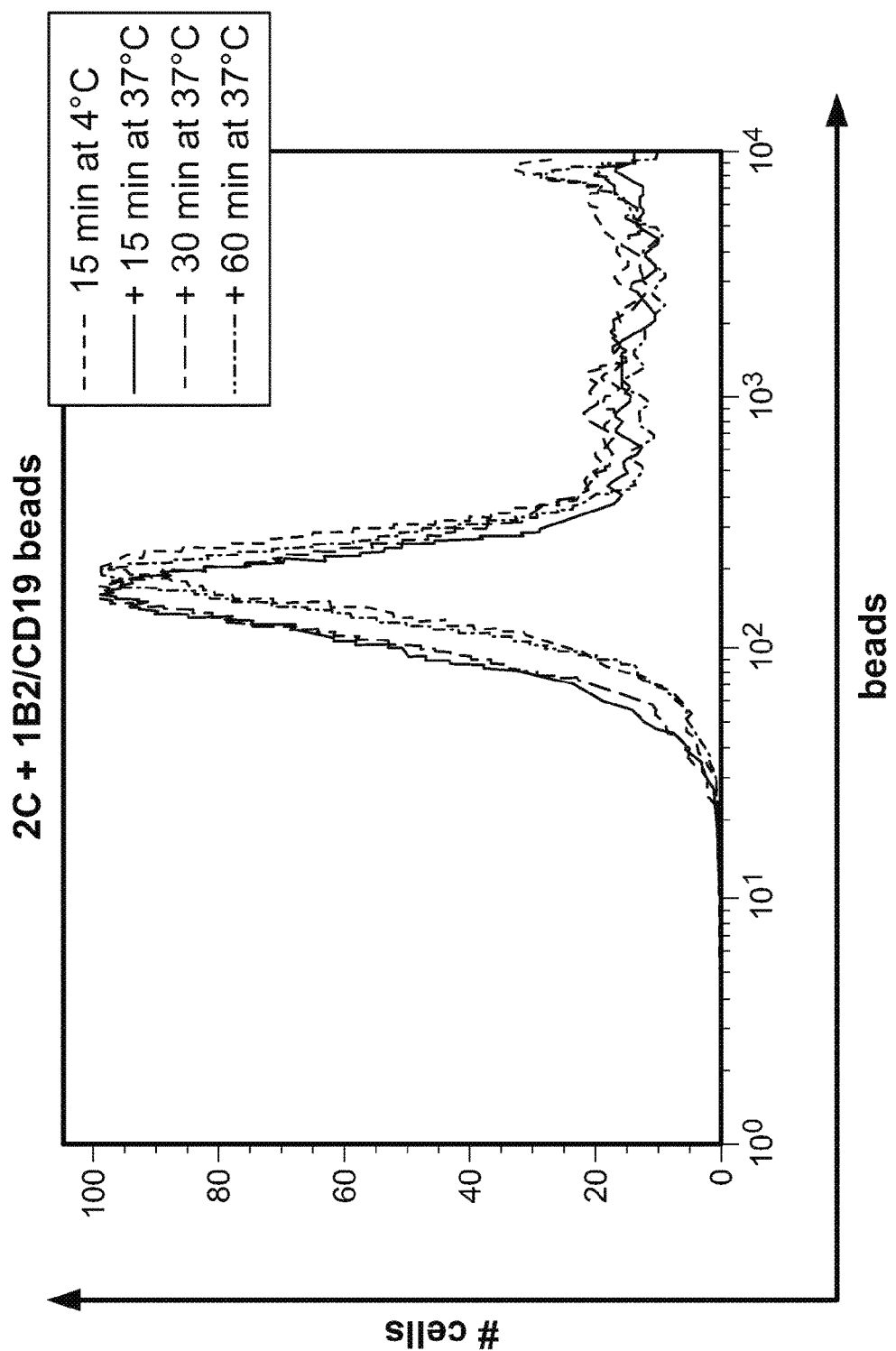

We next investigated the stability of bead to effector cell interaction. 2C effector cells were efficiently stained with 50 µl of 1B2/CD19 redirection beads (FIG. 3B, left most line), and all beads in excess were washed off. Staining was verified by secondary staining with anti-mouse IgG$_1$. Bead coated 2C cells were then transferred on 37° C. to determine if a sufficient targeting of target T2 cells in a later killing assay may occur. After different time points (FIG. 3B), redirection bead coated 2C cells were secondary stained with anti-mouse IgG$_1$ and analyzed for decrease of MFI similar to bead lose on effector 2C cells. Together, these data indicate that redirection bead staining of effector 2C cells is at least stable for 60 minutes when incubated at 37° C. This represents a sufficient time interval to provide effector to target cell interaction in a later killing assay.

Figure 3C:
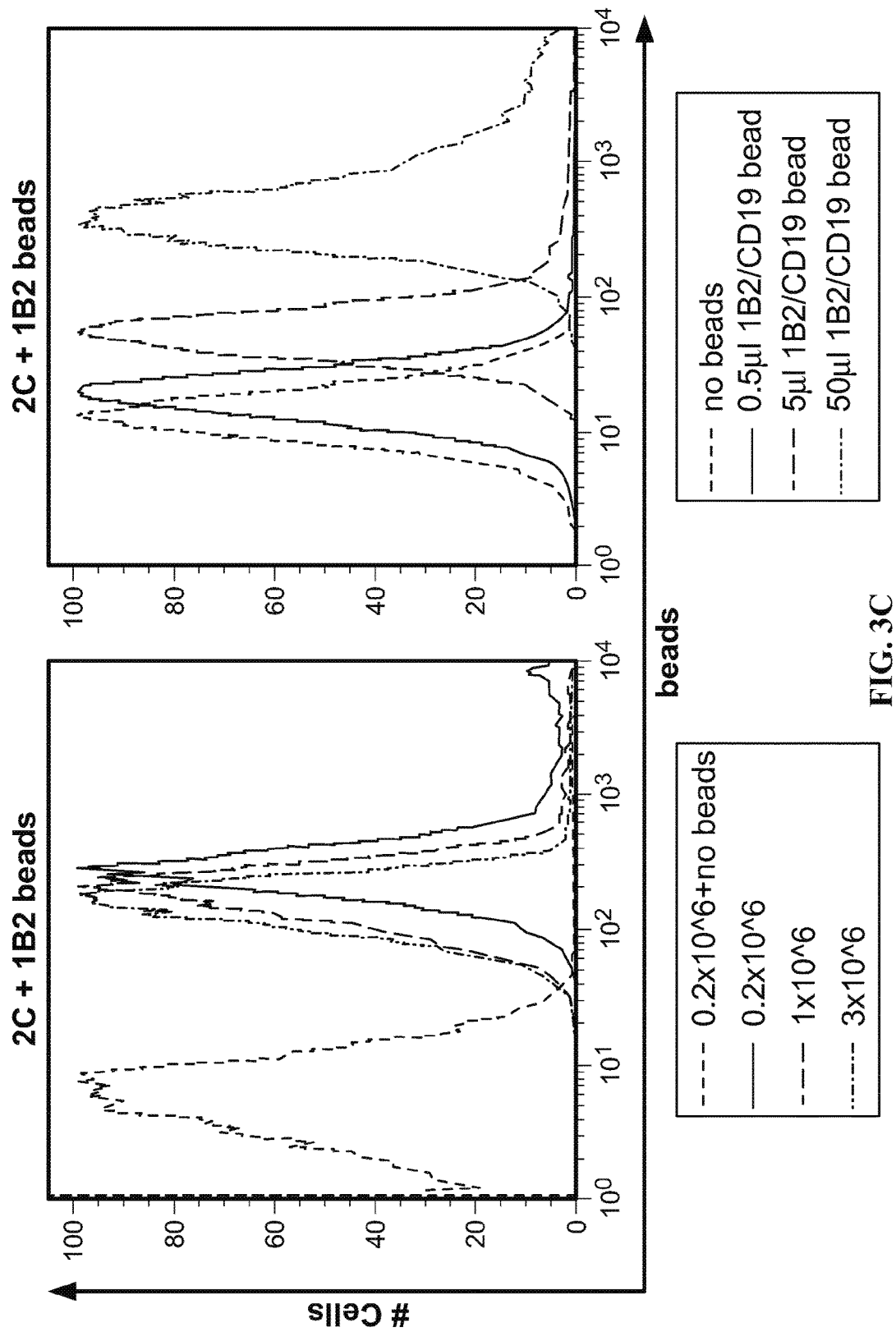

Finally, we examined how varying bead to cell ratio may interfere with an optimal staining outcome. We incubated the indicated amounts of 2C effector cells (FIG. 3C, left panel) with 1B2 beads at 4° C. for 15 minutes, washed them, and secondarily stained them with anti-mouse IgG$_1$. The best staining was achieved using $0.2 \times 10^6$ cells; however, higher amounts of cells were not correlated with a dramatic reduction in staining intensity. Otherwise, when bead amounts were varied as indicated (FIG. 3C, right panel), only $0.2 \times 10^6$ 2C cells stained with 50 µl 1B2 beads displayed a prominent staining efficiency. All other bead amounts (5 and 0.5 µl) significantly reduced the staining intensity.

Example 5

Redirection Beads Facilitate 2C Mediated Lysis of Human T2 Cells

To investigate if redirection beads could facilitate redirected killing of human target cells by mouse effector CTL, we developed two approaches to studying redirected lysis. In the first approach, we incubated redirection beads with target and effector cells during the course of the killing assay; this is referred to as the "co-culture approach." This approach mimics direct intravenous injection of redirection beads.

We also developed a "pre-targeted assay." In this assay, effector cells were initially incubated with redirection beads for varying amounts and time, then washed to remove free beads. Chromium-labeled target cells were added and monitored for lysis. This approach mimics ex vivo generation of effector cells and subsequent adoptive transfer after "redirection."

Redirection beads were able to facilitate lysis of target cells using either the co-culture or pretargeting approaches. In co-culture system, 1B2/CD19 redirection beads facilitated recognition of T2 target cells over the entire range of Effector:Target (E:T) cell ratios tested (FIG. 4A, left panel). In the co-culture assay, increased effector cells were associated with increased background killing. Therefore, the re-directional specific lysis window (the different between the induced killing by 1B2/CD19 and 1B2 beads) of around 30% (1:1), 20% (2:1) and only 10% (5:1) as E:T ratios increased.

Pre-targeted effector cells displayed a lower overall killing, but also a lower 1B2 bead background and a stable 1B2/CD19 specific re-direction lysis of approximately 20-25%. (FIG. 4A, right panel). Overall, this protocol seemed more reliable and stable in terms of efficiency consistently mediated approximately 20% specific lysis (FIG. 4B). One remarkable finding of this bead based approach is the relatively low E:T ratios that already show effective re-directional lysis compared to other reported approaches.

Figure 5A:
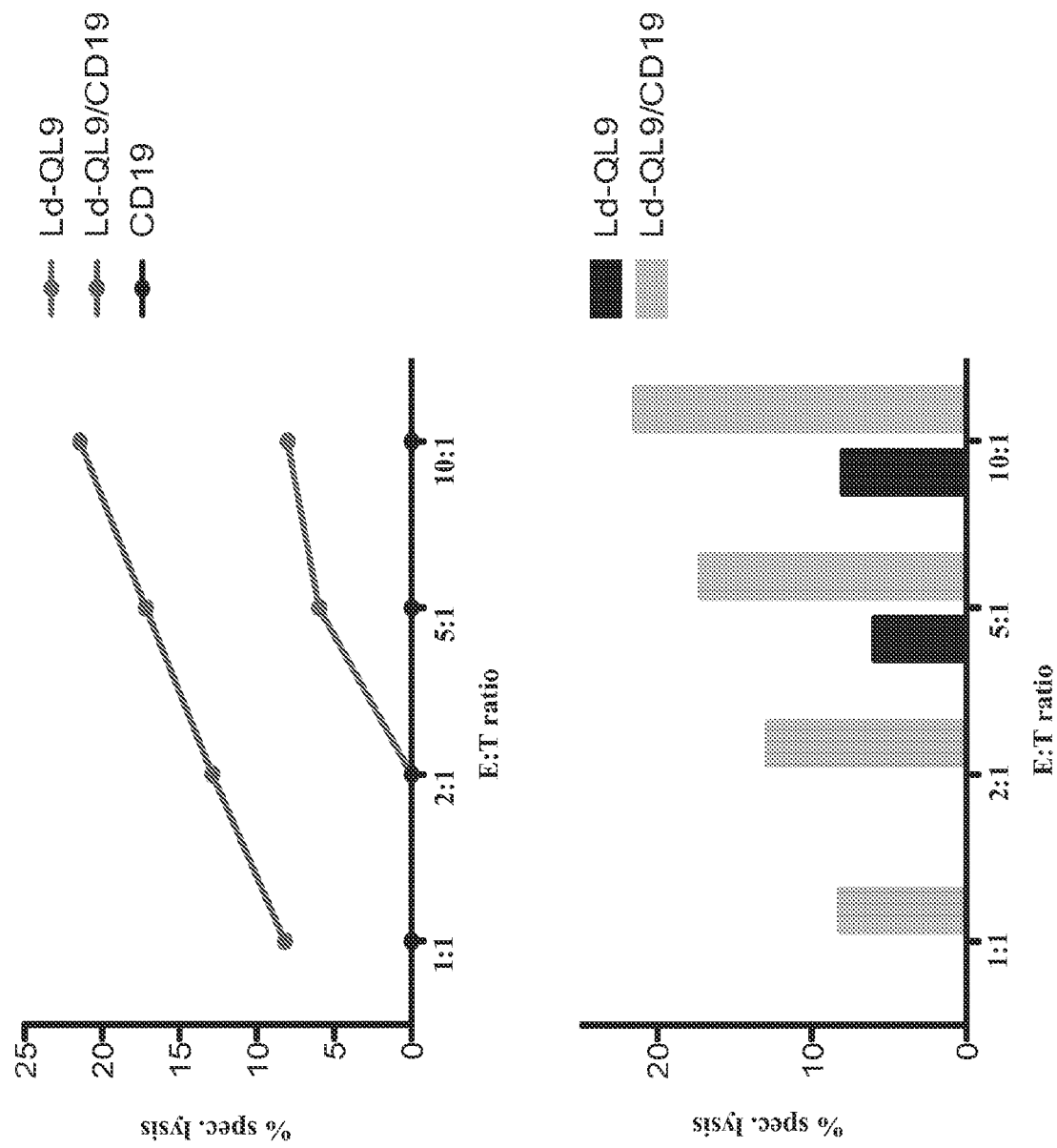
FIGS. 5A-B. Induction of redirected killing in T2 cells by pre-targeted MHC-Ig-based redirection beads (Example 5).
Figure 5B:
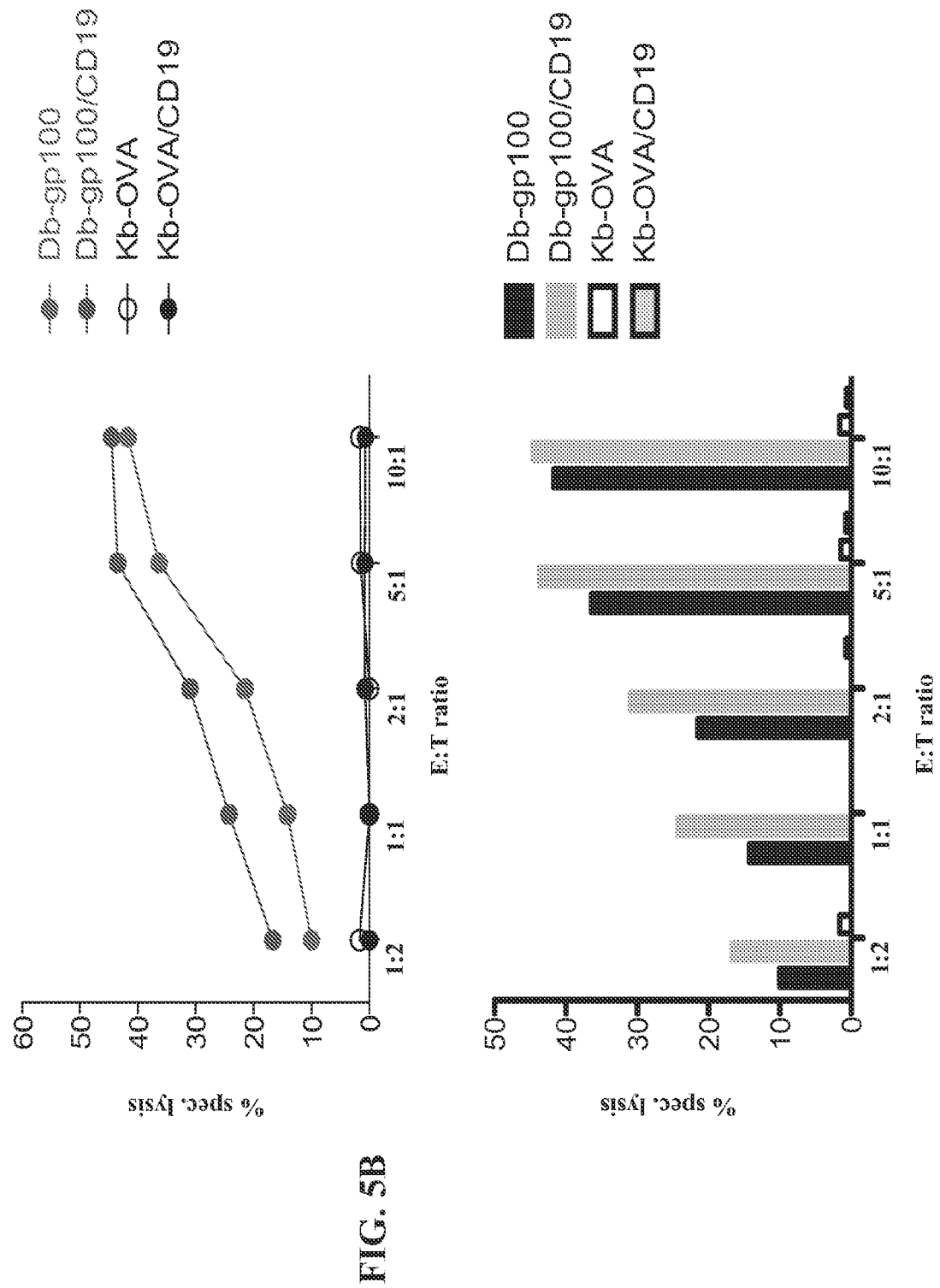

We further investigated killing of target cells using redirection beads made with MHC-Ig. Redirection beads made with Ld-QL9-Ig/CD19, an MHC-Ig complex specific for the CD8+ 2C T cells, induced up to 20% (10:1) lysis in a pretargeted assay. Only background amounts of nonspecific killing were detected in Ld-QL9-Ig bead samples, and no lysis was detected in CD19 bead control samples. This results in a re-directional lysis specific window of up to 15%. Overall, the engagement of a low affinity tumor TCR on CD8+ Pmel cells by Db-gp100-g/CD19 redirection beads displayed a higher lysis of up to 40% (10:1), but the re-directional specific lysis window was significantly reduced (to only 5%) because of a high Db-gp100-Ig control bead specific background lysis (FIG. 5B). Non-cognate loaded Kb-OVA-Ig beads did not show any lysis. Together, these data demonstrate that dimer based redirection beads are able to induce re-directional specific lysis in a human CD19+ B cell lymphoma cell line (T2).

The invention claimed is:

1. A nanoparticle which comprises on its surface:
   (A) an antibody that specifically binds to a target cell antigen or epitope thereof, wherein the target cell antigen is a tumor antigen; and
   (B) a moiety that binds to an antigen-specific T cell, wherein the moiety is
      an MHC class I-immunoglobulin complex presenting a peptide antigen, and
   wherein the nanoparticle does not comprise on its surface a T cell costimulatory molecule,
   wherein the nanoparticle has a mean particle diameter of from 25 nm to 125 nm,
      wherein the nanoparticle is bound to a cytotoxic T cell specific for said peptide antigen through said moiety, the nanoparticle is suspended in a pharmaceutically acceptable carrier, and the nanoparticle is capable of redirecting tumor-specific cytotoxic T cells to tumor cells in vivo.

2. The nanoparticle of claim 1, wherein the moiety is the MHC class I-immunoglobulin complex, and which is an MHC-Ig dimer.

3. The nanoparticle of claim 1, wherein the target cell is a hematological malignancy.

4. The nanoparticle of claim 1, wherein the antibody that specifically binds to a target cell antigen or epitope thereof is anti-CD19.

5. The nanoparticle of claim 1, wherein the nanoparticle has a mean particle diameter of from 50 nm to 100 nm.

6. A method for selectively directing tumor-specific cytotoxic T cells to tumor cells in a patient, comprising:

expanding a tumor-specific population of cytotoxic T cells ex vivo, and administering the tumor-specific cytotoxic T cells to a patient along with a population of nanoparticles comprising on their surface:

(A) an antibody that specifically binds to a target cell antigen or epitope thereof, wherein the target cell antigen is a tumor antigen; and (B) a moiety that binds to an antigen-specific T cell, wherein the moiety is
an MEW class I-immunoglobulin complex presenting a tumor associated antigen, and wherein the nanoparticle does not comprise on its surface a T cell costimulatory molecule, wherein the nanoparticles have a mean particle diameter of from 25 nm to 125 nm, and the nanoparticles are bound to the cytotoxic T cells through said moiety, thereby redirecting tumor-specific cytotoxic T cells to tumor cells in the patient.

7. The method of claim 6, wherein the patient has a hematological malignancy.

8. The method of claim 6, wherein the moiety is the MEW class I-immunoglobulin complex, and which is an MHC-Ig dimer.

9. The method of claim 6, wherein the antibody that specifically binds to a target cell antigen or epitope thereof is anti-CD19.

10. The method of claim 6, wherein the nanoparticle has a mean particle diameter of from 50 nm to 100 nm.

* * * * *

UNITED STATES PATENT AND TRADEMARK OFFICE
CERTIFICATE OF CORRECTION

PATENT NO. : 10,463,750 B2  
APPLICATION NO. : 14/767342  
DATED : November 5, 2019  
INVENTOR(S) : Jonathan Schneck et al.

Page 1 of 1

It is certified that error appears in the above-identified patent and that said Letters Patent is hereby corrected as shown below:

In the Claims

In Claim 6, Column 109, Line 11, change "MEW ;" to --MHC--;

In Claim 8, Column 109, Line 22, change "MEW ;" to --MHC--.

Signed and Sealed this  
Fourteenth Day of April, 2020

Andrei Iancu  
*Director of the United States Patent and Trademark Office*